US005696112A

United States Patent [19]

Albright et al.

[11] Patent Number: 5,696,112

[45] Date of Patent: *Dec. 9, 1997

[54] FUSED HETEROCYCLIC AZEPINES AS VASOPRESSIN ANTAGONISTS

[75] Inventors: Jay D. Albright; Efren G. Delos Santos, both of Nanuet, N.Y.

[73] Assignee: American Cyanamid Company, Madison, N.J.

[ * ] Notice: The term of this patent shall not extend beyond the expiration date of Pat. No. 5,654,297.

[21] Appl. No.: 373,839

[22] Filed: Jan. 17, 1995

[51] Int. Cl.[6] ...................... A61K 31/55; C07D 491/048; C07D 495/04

[52] U.S. Cl. ............................................ 514/215; 540/593

[58] Field of Search .............................. 540/593; 514/215

[56] References Cited

U.S. PATENT DOCUMENTS

| | | | |
|---|---|---|---|
| 4,414,225 | 11/1983 | Sauter et al. | 424/274 |
| 4,766,108 | 8/1988 | Ali | 514/16 |
| 5,055,448 | 10/1991 | Manning et al. | 514/16 |
| 5,070,187 | 12/1991 | Gavras et al. | 531/315 |
| 5,258,510 | 11/1993 | Ogawa et al. | 540/476 |

FOREIGN PATENT DOCUMENTS

| | | |
|---|---|---|
| 0382185 | 2/1990 | European Pat. Off. . |
| 0470514 | 8/1991 | European Pat. Off. . |
| 0514667 | 4/1992 | European Pat. Off. . |
| 0533240 | 9/1992 | European Pat. Off. . |
| 0533242 | 9/1992 | European Pat. Off. . |
| 0533243 | 9/1992 | European Pat. Off. . |
| 0533244 | 9/1992 | European Pat. Off. . |
| 0620216 | 4/1994 | European Pat. Off. . |
| 9105549 | 5/1991 | WIPO . |
| 9404525 | 3/1994 | WIPO . |
| 9414796 | 7/1994 | WIPO . |
| 9412476 | 9/1994 | WIPO . |
| 9420473 | 9/1994 | WIPO . |

OTHER PUBLICATIONS

J. Med. Chem., 1992,35, 3905–3918, Williams et al.
J. Med. Chem., 1992, 35, 3895–3904 – Manning et al.
J. Med. Chem., 1992, 35, 382–388, Manning et al.
From Vasopressin antagonist to Agonist, DN + P 4 (4), May 1991, Ruffolo et al. pp. 217–221.
Br. J. Pharmacol. (1992), 105, 787–791, Yamamura et al.
Science, vol. 252, pp. 572–574, Yamamura et al. (1991).
J. Med. Chem.,1992, 35, 3919–3927, Evans et al.
J. Med. Chem., 1993, 36, 3993–4005, Evans et al.

*Primary Examiner*—Philip I. Datlow
*Attorney, Agent, or Firm*—Steven R. Eck

[57] ABSTRACT

This invention relates to bicyclic non-peptide vasopressin antagonists useful in treating conditions where decreased vasopressin levels are desired, in conditions with excess renal water reabsorption and in conditions with increased vascular resistance and coronary vasoconstriction, the compounds of this invention having the core structure of

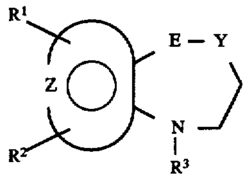

wherein:

E—Y is selected from the moieties —CH=CH—, $—CH_2CH_2—$, and

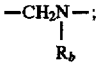

the moiety

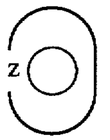

includes an optionally substituted, fused 6-membered heterocyclic aromatic ring containing two nitrogen atoms, a fused 5-membered heterocyclic aromatic ring containing either a) one heteroatom selected from O, S or N; b) two N atoms; or one N atom and one O or S atom;

and $R^1$, $R^2$, $R^3$ and $R_b$, are as defined herein.

31 Claims, No Drawings

FUSED HETEROCYCLIC AZEPINES AS VASOPRESSIN ANTAGONISTS

FIELD OF THE INVENTION

This invention relates to new bicyclic non-peptide vasopressin antagonists which are useful in treating conditions where decreased vasopressin levels are desired, such as in congestive heart failure, in disease conditions with excess renal water reabsorption and in conditions with increased vascular resistance and coronary vasoconstriction.

BACKGROUND OF THE INVENTION

Vasopressin is released from the posterior pituitary either in response to increased plasma osmolarity detected by brain osmoreceptors or decreased blood volume and blood pressure sensed by low-pressure volume receptors and arterial baroreceptors. The hormone exerts its action through two well defined receptor subtypes: vascular $V_1$ and renal epithelial $V_2$ receptors. Vasopressin-induced antidiuresis, mediated by renal epithelial $V_2$ receptors, helps to maintain normal plasma osmolarity, blood volume and blood pressure.

Vasopressin is involved in some cases of congestive heart failure where peripheral resistance is increased. $V_1$ antagonists may decrease systemic vascular resistance, increase cardiac output and prevent vasopressin induced coronary vasoconstriction. Thus, in conditions with vasopressin induce increases in total peripheral resistance and altered local blood flow, $V_1$ antagonists may be therapeutic agents. $V_1$ antagonists may decrease blood pressure, induced hypotensive effects and thus be therapeutically useful in treatment of some types of hypertension.

The blockage of $V_2$ receptors is useful in treating diseases characterized by excess renal reabsorption of free water. Antidiuresis is regulated by the hypothalamic release of vasopressin (antidiuretic hormone) which binds to specific receptors on renal collecting tubule cells. This binding stimulates adenylyl cyclase and promotes the cAMP-mediated incorporation of water pores into the luminal surface of these cells. $V_2$ antagonists may correct the fluid retention in congestive heart failure, liver cirrhosis, nephritic syndrome, central nervous system injuries, lung disease and hyponatremia.

Elevated vasopressin levels occur in congestive heart failure which is more common in older patients with chronic heart failure. In patients with hyponatremic congestive heart failure and elevated vasopressin levels, a $V_2$ antagonist may be beneficial in promoting free water excretion by antagonizing the action of antidiuretic hormone, On the basis of biochemical and pharmacological effects of the hormone, antagonists of vasopressin are expected to be therapeutically useful in the treatment and/or prevention of hypertension, cardiac insufficiency, coronary vasospasm, cardiac ischemia, renal vasospasm, liver cirrhosis, congestive heart failure, nephritic syndrome, brain edema, cerebral ischemia, cerebral hemorrhage-stroke, thrombosis-bleeding and abnormal states of water retention.

The following prior art references describe peptide vasopressin antagonists: M. Manning et al., *J. Med. Chem.*, 35, 382 (1992); M. Manning et al., *J. Med. Chem.*, 35, 3895 (1992); H. Gavras and B. Lammek, U.S. Pat. No. 5,070,187 (1991); M. Manning and W. H. Sawyer, U.S. Pat. No. 5,055,448 (1991) F. E. Ali, U.S. Pat. No. 4,766,108 (1988); R. R. Ruffolo et al., *Drug News and Perspective*, 4(4), 217, (May) (1991). P. D. Williams et al., have reported on potent hexapeptide oxytocin antagonists [*J. Med. Chem.*, 35, 3905 (1992)] which also exhibit weak vasopressin antagonist activity in binding to $V_1$ and $V_2$ receptors. Peptide vasopressin antagonists suffer from a lack of oral activity and many of these peptides are not selective antagonists since they also exhibit partial agonist activity.

Non-peptide vasopressin antagonists have recently been disclosed, Y. Yamamura et al., *Science*, 252, 579(1991); Y. Yamamura et al., *Br. J. Pharmacol*, 105, 787(1992); Ogawa et al., (Otsuka Pharm Co., LTD.) EP 0514667-A1; JP 04154765-A; EPO 382185-A2; WO9105549 and U.S. Pat. No. 5,258,510; WO 9404525 Yamanouchi Pharm. Co., Ltd., WO 9420473; WO 9412476; WO 9414796; Fujisawa Co. Ltd., EP 620216-A1 Ogawa et al, (Otsuka Pharm. Co.) EP 470514A disclose carbostyril derivatives and pharmaceutical compositions containing the same. Non-peptide oxytocin and vasopressin antagonist have been disclosed by Merck and Co.; M. G. Bock and P. D. Williams, EP 0533242A; M. G. Bock et al., EP 0533244A; J. M. Erb, D. F. Verber, P. D. Williams, EP 0533240A; K. Gilbert et al., EP 0533243A.

Premature birth can cause infant health problems and mortality and a key mediator in the mechanism of labor is the peptide hormone oxytocin. On the basis of the pharmacological action of oxytocin, antagonists of this hormone are useful in the prevention of preterm labor, B. E. Evans et al., *J. Med. Chem.* 35, 3919(1992), *J. Med. Chem.*, 36, 3993 (1993) and references therein. The compounds of this invention are antagonists of the peptide hormone oxytocin and are useful in the control of premature birth.

The present invention relates to novel tricyclic derivatives which exhibit antagonist activity at $V_1$ and/or $V_2$ receptors and exhibit in vivo vasopressin antagonist activity. The compounds also exhibit antagonist activity at oxytocin receptors.

SUMMARY OF THE INVENTION

This invention relates to new compounds selected from those of the general Formula I:

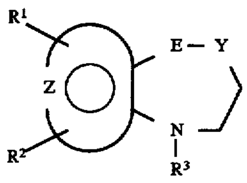

I wherein

E—Y is selected from the moieties —CH=CH—,

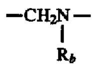

$—CH_2—CH_2—$ and when Y is $—CH_2—$, E is selected from the moieties:

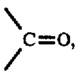

—CHOH,

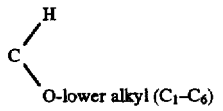

CH—S-lower alkyl ($C_1$–$C_6$), —$CHNH_2$, —CHN-lower alkyl ($C_1$–$C_6$), —C[N-lower alkyl ($C_1$–$C_6$)]$_2$,

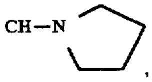, 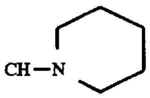, 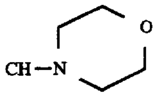

—CHOCO-lower alkyl ($C_1$–$C_6$), —CHNH $(CH_2)_m$ $NH_2$; —CHNH$(CH_2)_m$—NH-lower alkyl ($C_1$–$C_6$), —CHNH$(CH_2)_m$—N[lower alkyl ($C_1$–$C_6$) ]$_2$; —CHNH$(CH_2)_m$—S-lower alkyl ($C_1$–$C_6$) , —CHNH $(CH_2)_m$—O-lower alkyl ($C_1$–$C_6$),

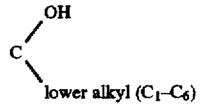

S, O, —NH, —N-lower alkyl ($C_1$–$C_6$), —NCO-lower alkyl ($C_1$–$C_6$), m is an integer of 2 to 6;

and the moiety:

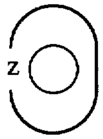

represents: (1) a fused unsaturated 6-membered heterocyclic aromatic ring containing two nitrogen atoms, optionally substituted by one or two substitutents selected from ($C_1$–$C_3$)lower alkyl, halogen, amino, ($C_1$–$C_3$)lower alkoxy or ($C_1$–$C_3$)lower alkylamino; (2) a fused 5-membered aromatic (unsaturated) heterocyclic ring having one heteroatom selected from O, N or S; (3) a 5-membered aromatic (unsaturated) heterocyclic ring having two nitrogen atoms; (4) a 5-membered aromatic (unsaturated) heterocyclic ring having one nitrogen atom together with either one oxygen or one sulfur atom; wherein the 5 or 6-membered heterocyclic rings are optionally substituted by ($C_1$–$C_3$)lower alkyl, halogen, or ($C_1$–$C_3$)lower alkoxy;

$R^3$ is —COAr, wherein Ar is a moiety selected from the group consisting of:

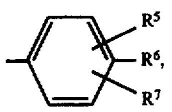, 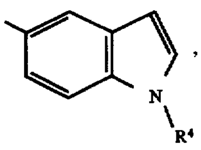,

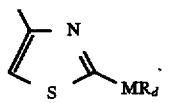, 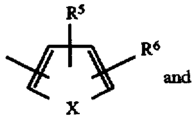 and

-continued

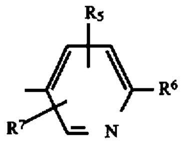

wherein

X is selected from O, S, —NH, —$NCH_3$ and —$NCOCH_3$; $R^4$ is selected from hydrogen, lower alkyl ($C_1$–$C_3$), —CO-lower alkyl ($C_1$–$C_3$),

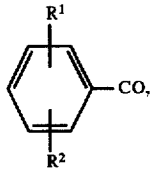 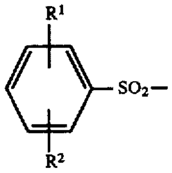

—$SO_2$-lower alkyl ($C_1$–$C_3$); $R^1$ and $R^2$ are selected from hydrogen, ($C_1$–$C_3$)lower alkyl, ($C_1$–$C_3$)lower alkoxy and halogen; $R^5$ is selected from hydrogen, ($C_1$–$C_3$)lower alkyl, ($C_1$–$C_3$)lower alkoxy and halogen; $R^6$ is selected from (a) moieties of the formulae:

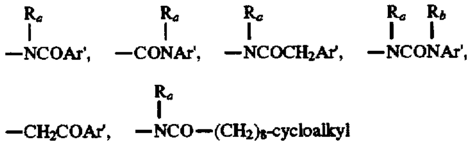

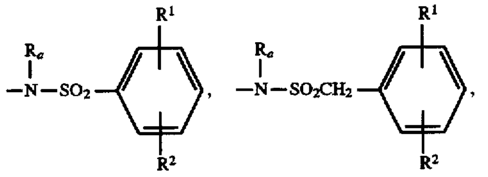

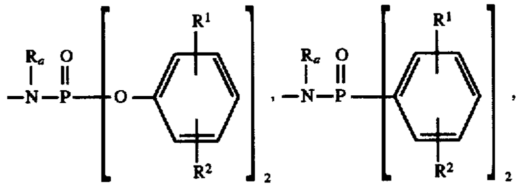

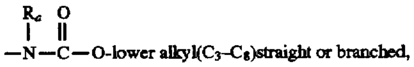

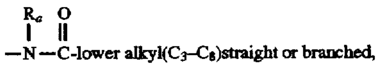

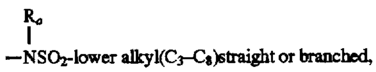

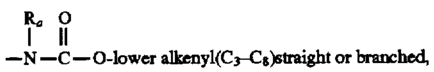

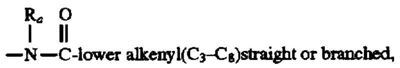

-continued

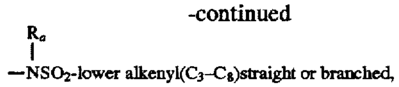

wherein cycloalkyl is defined as ($C_3$–$C_6$)cycloalkyl, cyclohexenyl or cyclopentenyl; and $R_a$ is independently selected from hydrogen, —$CH_3$ or —$C_2H_5$,

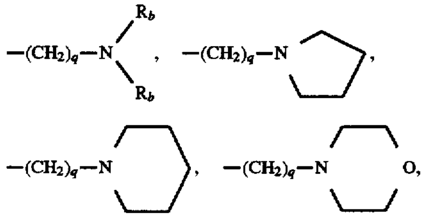

—$(CH_2)_q$—O-lower alkyl ($C_1$–$C_3$), —$CH_2CH_2OH$, q is one, two, or three, $R_b$ is independently selected from hydrogen, —$CH_3$ or —$C_2H_5$, (b) a moiety of the formula:

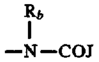

wherein J is $R_a$, lower alkyl ($C_3$–$C_8$) branched or unbranched, lower alkenyl($C_3$–$C_8$) branched or unbranched, O-lower alkyl ($C_3$–$C_8$) branched or unbranched, —O-lower alkenyl($C_3$–$C_8$) branched or unbranched, tetrahydrofuran, tetrahydrothiophene, and the moieties:

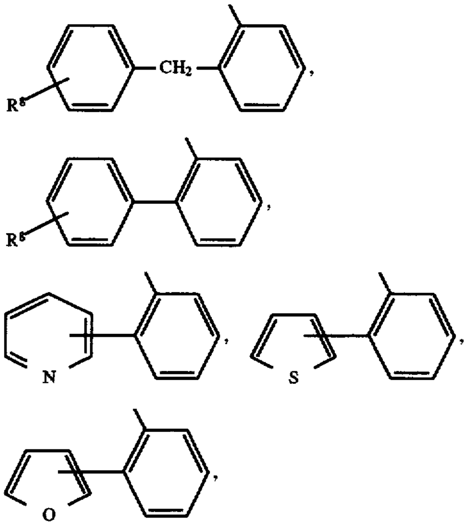

or —$CH_2$—K' wherein K' is ($C_1$–$C_3$)-lower alkoxy, halogen, tetrahydrofuran, tetrahydro-thiophene or the heterocyclic ring moiety:

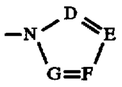

wherein D, E, F and G are selected from carbon or nitrogen and wherein the carbon atoms may be optionally substituted with halogen, ($C_1$–$C_3$)lower alkyl, hydroxy, —CO-lower alkyl ($C_1$–$C_3$), CHO, ($C_1$–$C_3$) lower alkoxy, —$CO_2$-lower alkyl ($C_1$–$C_3$), and $R_a$ and $R_b$ are as hereinbefore defined;

(c) a moiety of the formula:

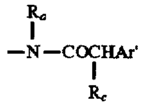

wherein $R_c$ is selected from halogen, ($C_1$–$C_3$) lower alkyl, —O-lower alkyl ($C_1$–$C_3$), OH,

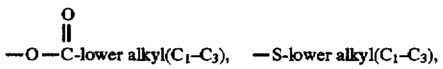

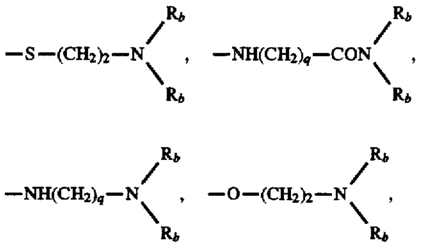

wherein $R_a$ and $R_b$ are as hereinbefore defined;

(d) a moiety of the formula:

—M—$R_d$ wherein $R_d$ is lower alkyl ($C_3$–$C_8$), lower alkenyl ($C_3$–$C_8$), or —$(CH_2)_p$-cycloalkyl($C_3$–$C_6$), when M is O, S, NH, $NCH_3$ and the moiety —M—$R_d$ wherein $R_d$ is selected from the moieties:

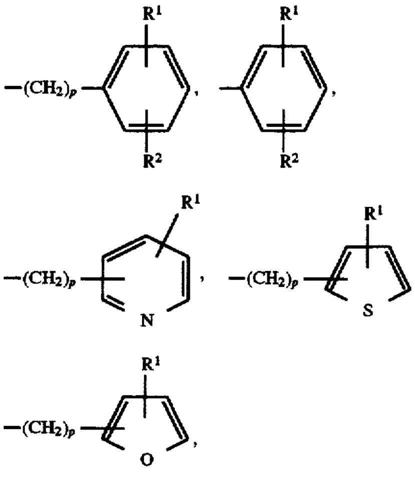

wherein p is zero to four and M is a bind or M is selected from O, S, NH, $NCH_3$; wherein $R^1$, $R^2$ and $R_a$ are as hereinbefore defined;

wherein Ar' is selected from moieties of the formula:

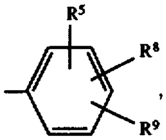
,
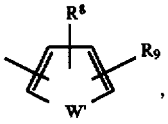
,
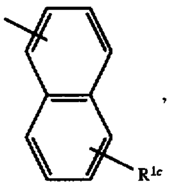
,
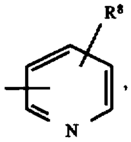
, and
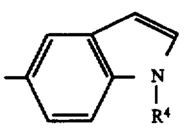

wherein W' is selected from O, S, NH, N-lower alkyl ($C_1$–$C_3$) NHCO-lower alkyl ($C_1$–$C_3$), and $NSO_2$lower alkyl ($C_1$–$C_3$); $R^7$ is selected from hydrogen, lower alkyl ($C_1$–$C_3$), halogen, O-lower alkyl ($C_1$–$C_3$) and $CF_3$; $R^8$ and $R^9$ are independently selected from hydrogen, lower alkyl ($C_1$–$C_3$), —S-lower alkyl ($C_1$–$C_3$), halogen, —NH-lower alkyl ($C_1$–$C_3$), —N-[lower alkyl ($C_1$–$C_3$)]$_2$, —$OCF_3$, —OH, —CN, —S—$CF_3$, —$NO_2$, —$NH_2$, O-lower alkyl ($C_1$–$C_3$), NHCO lower alkyl ($C_1$–$C_3$), O—CO-lower alkyl ($C_1$–$C_3$), —$N(R_b)(CH_2)_q$—$N(R_b)_2$ and $CF_3$ and;

$R^{10}$ is selected from hydrogen, halogen and lower alkyl ($C_1$–$C_3$) and the pharmaceutically acceptable salts thereof.

DETAILED DESCRIPTION OF THE INVENTION

Within the group of the compounds defined by Formula I, certain subgroups of compounds are broadly preferred. Broadly preferred are those compounds wherein $R^3$ is the moiety:

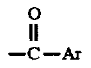

and

Ar is selected from the moiety:

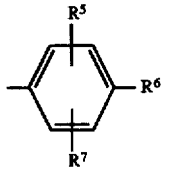

wherein $R_a$, $R_b$, $R^1$, $R^2$, $R^5$, $R^6$ and $R^7$ are as hereinbefore defined.

Especially preferred are compounds wherein $R^3$ is the moiety:

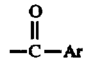
and

Ar is selected from the moiety:

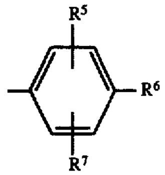

$R^6$ is

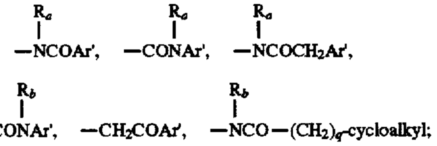

wherein cycloalkyl is defined as $C_3$ to $C_6$ cycloalkyl, cyclohexenyl or cyclopentenyl;

$R_a$, $R_b$, $R^1$, $R^2$, $R^5$, $R^6$, $R^7$ as hereinbefore defined; and Ar' is selected from the moieties:

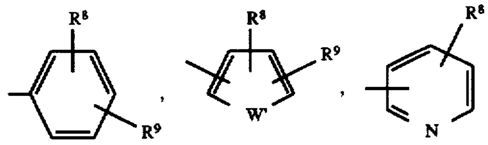

wherein $R^8$, $R^9$ and W' are as hereinbefore defined.

Also especially preferred are compounds wherein Y is $CH_2$ and E in Formula I is —$CH_2$, —CHOH, —$CHNH_2$, —CHNH-lower alkyl ($C_1$–$C_3$), —CHN[lower alkyl ($C_1$–$C_3$)]$_2$ and —CHO-lower alkyl ($C_1$–$C_3$);

and $R_a$, $R_b$, $R^1$, $R^2$, $R^4$, $R^5$, $R^6$, $R^7$, $R^8$ and $R^9$ are as hereinbefore defined.

The most preferred of the compounds of Formula I are those wherein Y is $CH_2$ and E is —$CH_2$, —CHOH, —$CHNH_2$, —CHNH-lower alkyl ($C_1$–$C_3$), —CHN[lower alkyl ($C_1$–$C_3$)]$_2$ and —CHO lower alkyl ($C_1$–$C_3$);

$R^3$ is the moiety

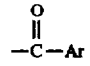

Ar is selected from the moieties:

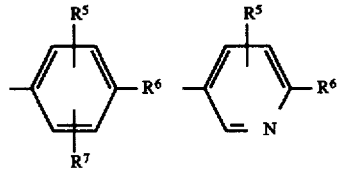

$R^6$ is

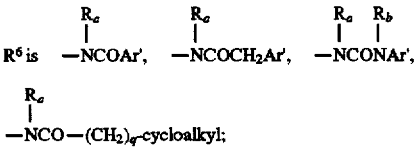

$(CH_2)_n$-cycloalkyl wherein cycloalkyl is defined as ($C_3$–$C_6$) cycloalkyl, cyclohexenyl or cyclopentenyl; $R_a$, $R_b$, $R^1$, $R^2$, $R^5$, $R^7$ are as hereinbefore defined;

and Ar' is a moiety:

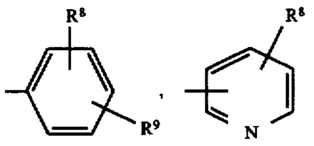

wherein $R^8$ and $R^9$ are as previously defined.

The most highly broadly preferred of the compounds of Formula I are those wherein Y is $CH_2$ and E is —$CH_2$, —CHOH, —$CHNH_2$, —CHNH-lower alkyl ($C_1$–$C_3$), —CHN[lower alkyl ($C_1$–$C_3$)]$_2$ and —CHO lower alkyl ($C_1$–$C_3$), wherein the moiety:

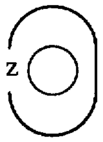

is a fused unsubstituted or substituted thiophene, furan, pyrrole, pyrazole or pyridine ring; $R_a$, $R_b$, $R^1$, $R^2$, $R^4$, $R^5$, $R^7$, $R^8$, and $R^9$ are as previously defined;

$R^3$ is the moiety:

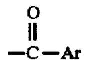

wherein

Ar is:

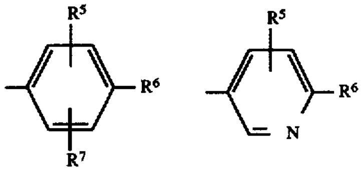

and $R^6$ is selected from the group

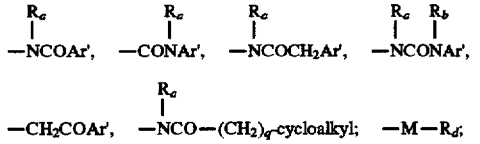

where

Ar' is selected from the group

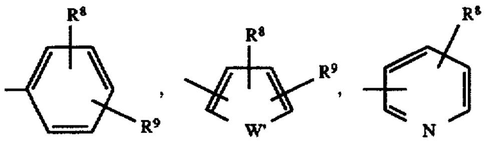

and

W' and cycloalkyl are as previously described.

More particularly preferred are compounds of the formula:

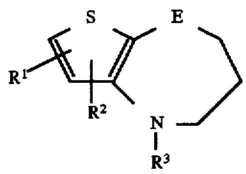

wherein

E is selected from —$CH_2$, —CHOH, —$CHNH_2$, —CHNH-lower alkyl ($C_1$–$C_3$), —CHN[lower alkyl ($C_1$–$C_3$)]$_2$ and —CHO lower alkyl ($C_1$–$C_3$);

$R^3$ is the moiety:

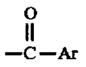

wherein

Ar is selected from the moieties:

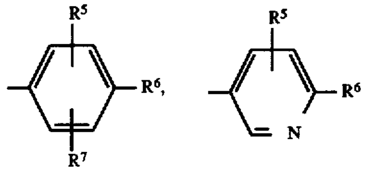

$R^6$ is

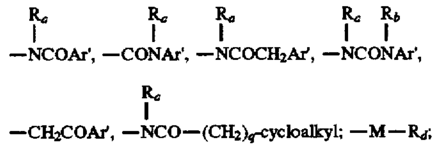

and

Ar' is selected from the moieties:

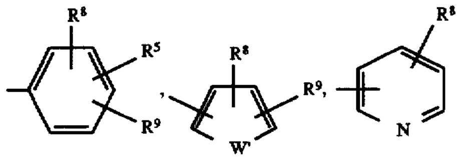

wherein $R_a$, $R_b$, $R^1$, $R^2$, $R^5$, $R^7$, $R^8$, $R^9$, cycloalkyl and W' are as hereinbefore described.

Also particularly preferred are compounds of the formula:

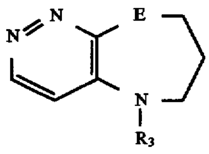

wherein

E is selected from —$CH_2$, —CHOH, —$CHNH_2$, —CHNH-lower alkyl ($C_1$–$C_3$), —CHN[lower alkyl ($C_1$–$C_3$)]$_2$ and —CHO lower alkyl ($C_1$–$C_3$);

$R^3$ is the moiety:

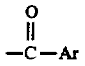

wherein

Ar is selected from the moieties:

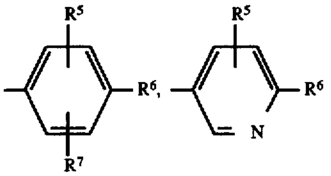

$R^6$ is

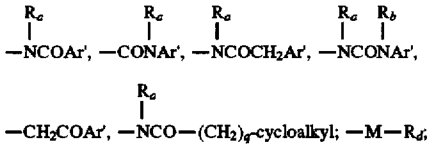

Ar' is selected from the moieties:

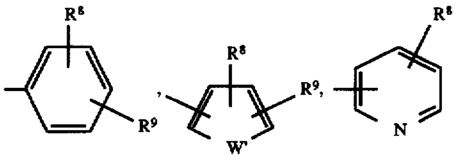

wherein $R_a$, $R_b$, $R^1$, $R^2$, $R^5$, $R^6$, $R^8$, $R^9$, cycloalkyl and W' are as hereinbefore described.

More particularly preferred are compounds of the formulae:

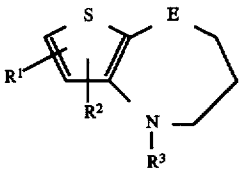

and

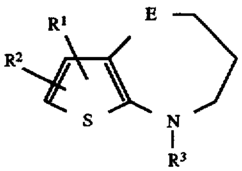

wherein

E is selected from —$CH_2$, —CHOH, —$CHNH_2$, —CHNH-lower alkyl ($C_1$–$C_3$), —CHN[lower alkyl ($C_1$–$C_3$)]$_2$ and —CHO lower alkyl ($C_1$–$C_3$);

$R^3$ is the moiety:

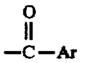

wherein

Ar is the moiety:

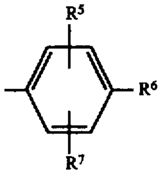

or

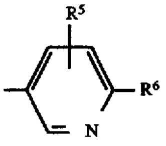

$R^6$ is

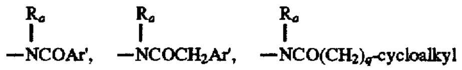

wherein $R_a$ is independently selected from hydrogen or —$CH_3$; Ar' is selected from the moieties:

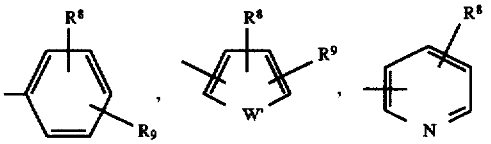

wherein $R^1$, $R^2$, $R^5$, $R^7$, $R^8$, $R^9$, and W' are as hereinbefore described.

Also particularly preferred are compounds of the formulae:

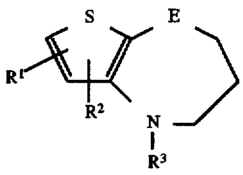

and

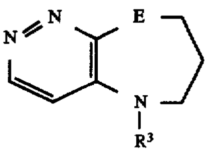

wherein

E is selected from —$CH_2$, —CHOH, —$CHNH_2$, —CHNH-lower alkyl ($C_1$–$C_3$), —CHN[lower alkyl ($C_1$–$C_3$)]$_2$ and —CHO lower alkyl ($C_1$–$C_3$);

$R^3$ is the moiety:

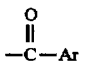

wherein

Ar is selected from the moieties:

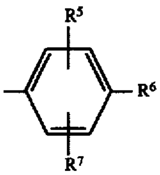

and

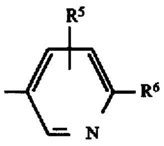

$R^6$ is

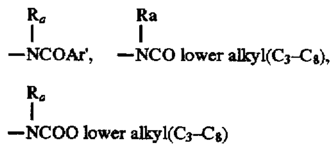

$R_a$ is independently selected from hydrogen, —$CH_3$ or —$C_2H_5$ and Ar' is selected from the moieties:

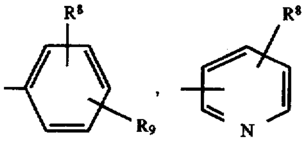

wherein $R^1$, $R^2$, $R^5$, $R^7$, $R^8$, and $R^9$ are as hereinbefore defined.

Compounds of this invention may be prepared as shown in Scheme I by reaction of azepine derivatives of Formula 3 with a substituted or unsubstituted 4-nitrobenzoyl chloride 4a or a substituted or unsubstituted 6-nitronicotinoyl chloride 4b to give the intermediate 5a and 5b. Reduction of the nitro group in intermediate 5 gives the 4-aminobenzoyl derivative 6a and the 6-aminonicotinoyl derivative 6b- The reduction of the nitro group in intermediate 5 may be carried out under catalytic reduction conditions (hydrogen-Pd/C; Pd/C-hydrazineethanol) or under chemical reduction conditions ($SnCl_2$-ethanol; Zn-acetic acid $TiCl_3$) and related reduction conditions known in the art for converting a nitro group to an amino group. The conditions for conversion of the nitro group to the amino group are chosen on the basis of comparability with the preservation of other functional groups in the molecule.

Reaction of compounds of Formula 6 with aroyl chloride or related activated aryl carboxylic acids in solvents such as chloroform, dichloromethane, dioxane, tetrahydrofuran, toluene and the like in the presence of a tertiary base such as triethylamine and diisopropylethylamine or pyridine and the like, affords the compounds 8 vasopressin antagonists.

Scheme 1

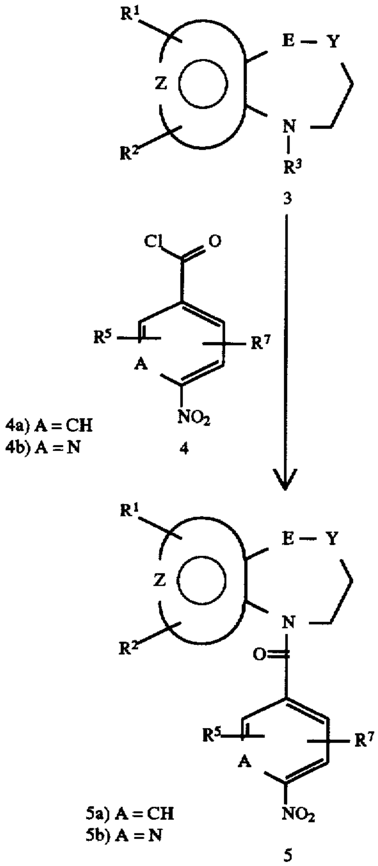

3

4a) A = CH
4b) A = N

4

5a) A = CH
5b) A = N

5

-continued
Scheme 1

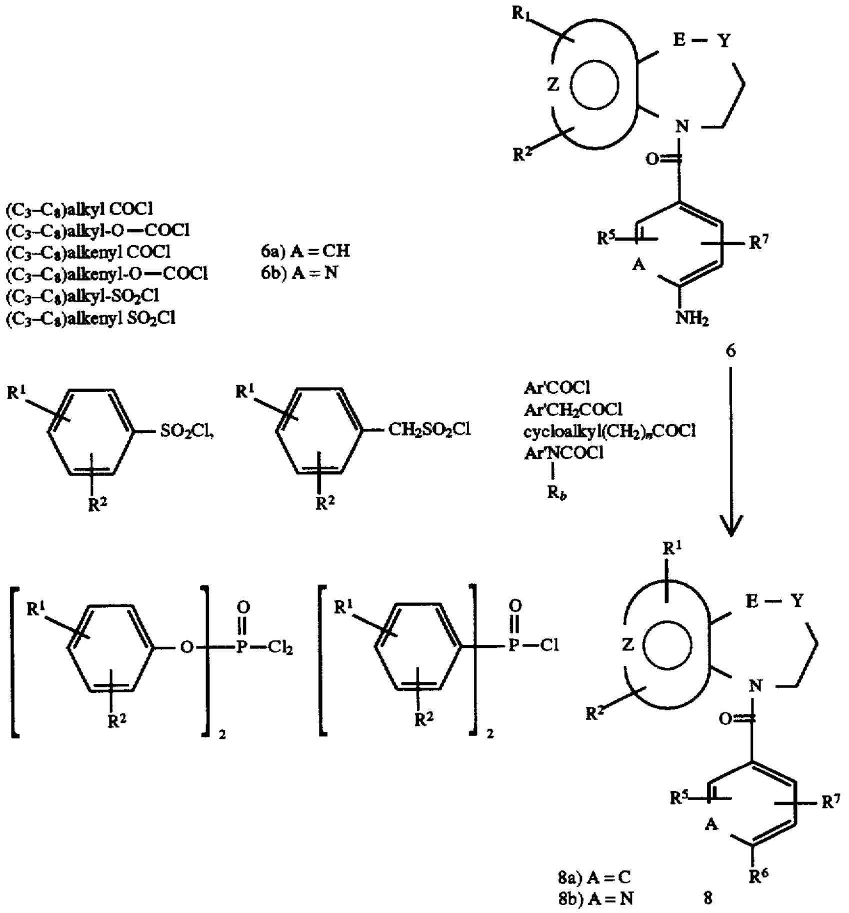

Reaction of bicyclic derivatives of Formula 6 with either a carbamoyl derivative 9 or a isocyanate derivative 10 gives compounds (Scheme 2) of Formula 11 which are vasopressin antagonists of Formula I wherein $R^6$ is

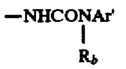

Scheme 2

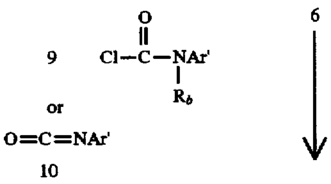

-continued
Scheme 2

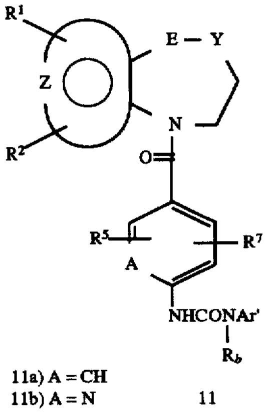

Reaction of bicyclic derivatives of Formula 6 with arylacetic acids, activated as the acid chlorides 12, anhydrides, mixed anhydrides or activated with known activating reagents, gives compounds 13 (Scheme 3).

Scheme 3

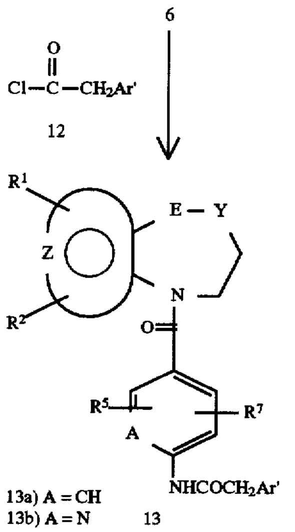

6

12

13a) A = CH
13b) A = N
13

The compounds of Formula I wherein E, Y, $R^1$, $R^2$, $R^3$ and $R^4$ are as defined and the aryl of $R^3$ (—COAr) is

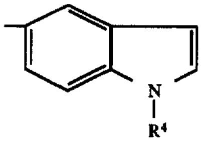

may be prepared, as shown in Scheme 4, by reacting an activated ester of the indole-5-carboxylic acids 14 with bicyclic derivatives 3a and 3b. The indole-5-carboxylic acids 14 may be activated by preparing the anhydride, a mixed anhydride or reacting with diethyl cyanophosphonate, N,N-carbonyldiimidazole or related peptide coupling reagents. As an example, the derivative 15 may be prepared by the reaction of acid 14 and N,N-carbonyldiimidazole in tetrahydrofuran; the solvent is removed and the derivative reacted with 3 at 100° C. to 120° C. without a solvent. Alternatively, t may be reacted with 15 in a solvent such as toluene or xylene at reflux temperatures. The activating reagent for the indole acids 14 is chosen on the basis of its compatibility with the $R^4$ group and its reactivity with the azepine derivative 3 to give the vasopressin antagonist 16.

Scheme 4

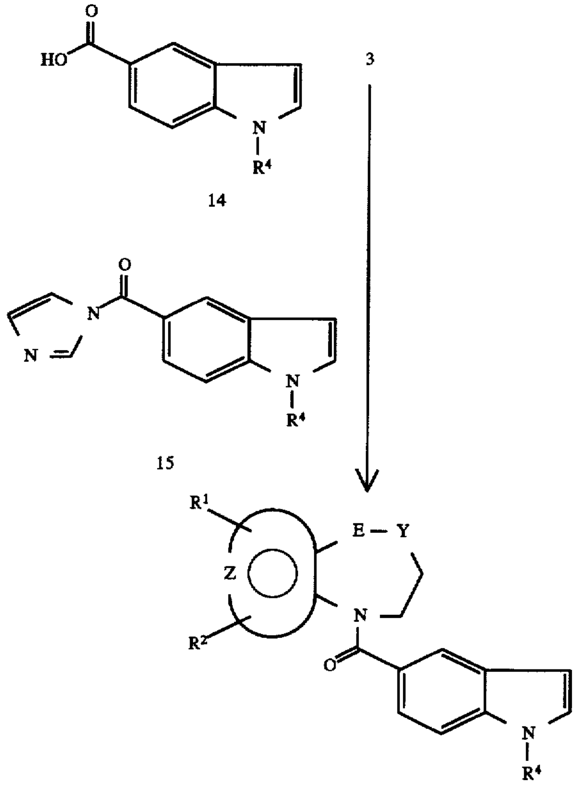

3
14
15
16

The compounds of Formula I wherein E, Y, $R^1$, $R^2$, $R^3$, $R^5$, and $R^7$ are as defined and the $R^3$ (—COAr) aryl group is

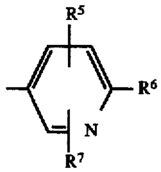

wherein $R^6$ is —M—$R_a$ wherein M is O, S, NH, N—$CH_3$ and $R_a$ is as previously defined may be prepared as shown in Scheme 5 by first converting the azepine derivatives 3 into the intermediate 17 and then reacting these nicotinolyl intermediates with derivatives of the formulae: HM—$R_a$ in the presence of a non-nucleophilic base such as N,N-diisopropylethylamine to give products 18. The best results are obtained in the displacement of the halogen in the nicotinolyl intermediates 17, when the halogen atom is a fluoro group. With nucleophilic amines (M=NH, $NCH_3$) the reaction can be carried out with the 6-chloro, bromo or fluoro derivatives 17 in (1) the absence of a non-nucleophilic base; (2) in a non-nucleophilic solvent; or (3) with excess amine and no solvent. With derivatives $HOR_d$ the 6-fluoro derivative 17 is required for satisfactory conversion of 17 to 18.

Scheme 5

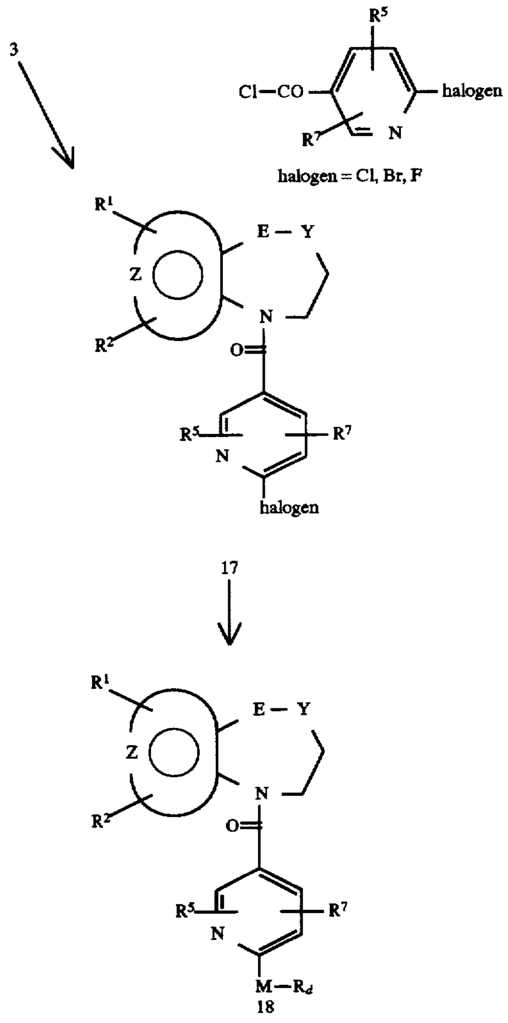

Alternatively, the products 18 may be prepared by first forming derivatives of the Formula 19 and then coupling these derivatives with the azepine compounds 3 (Scheme 6). The carboxylic acid intermediates are activated for coupling to the azepine compounds 3 by reaction with peptide coupling reagents, by conversion to the acid chlorides, anhydrides or mixed anhydrides.

Scheme 6

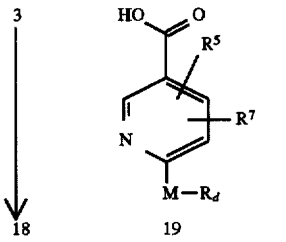

As an alternative method for synthesis of compounds of this invention as depicted in Formula I wherein $R_a$, $R_b$, $R^1$, $R^2$, $R^5$, $R^7$, A, E and Y are as previously defined and $R^3$ is

is the coupling of aryl carboxylic acids 20 with the azepine derivative 3. (Scheme 7)

The aryl carboxylic acids are activated for coupling by conversion to an acid chloride, bromide or anhydride or by first reacting with an activating reagent such as N,N-dicyclocarbodiimide, diethyl cyanophosphonate and related "peptide type" activating reagents. The method of activating the acids 20 for coupling to the azepine derivative 3 is chosen on the basis of compatibility with other substituent groups in the molecule. The method of choice is the conversion of the aryl carboxylic acid 20 to the corresponding aroyl chloride. The aryl acid chlorides 21 may be prepared by standard procedures known in the art, such as reaction with thionyl chloride, oxalyl chloride and the like. The coupling reaction is carried out in solvents such as halogenated hydrocarbons, toluene, xylene, tetrahydrofuran, dioxane in the presence of pyridine or tertiary bases such as triethylamine and the like (Scheme 7). Alternatively, the aroyl chlorides, prepared from the aryl carboxylic acids 20 may be reacted with derivatives 3 in pyridine with or without 4-(dimethylamino)pyridine to give derivatives 22.

In general, when the aryl carboxylic acids are activated with N,N-carbonyldiimidazole and other "peptide type" activating reagents, higher temperatures are required than when the aroyl chlorides are used. The reaction may be carried out in a higher boiling solvent xylene or without a solvent (100° C. to 150° C.).

The activation of aryl carboxylic by conversion to the acid chlorides with thionyl chloride or oxalyl chloride is preferred since the more reactive aroyl chlorides give better yields of product. The synthesis of selected examples is illustrated in Scheme 7.

Scheme 7

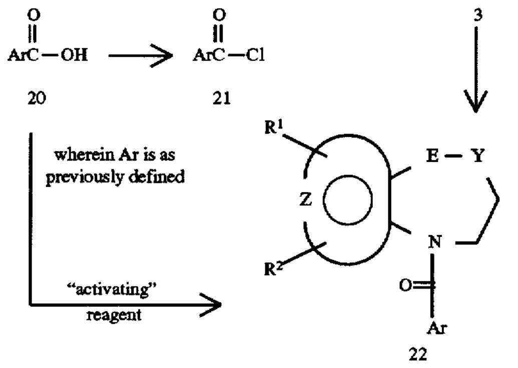

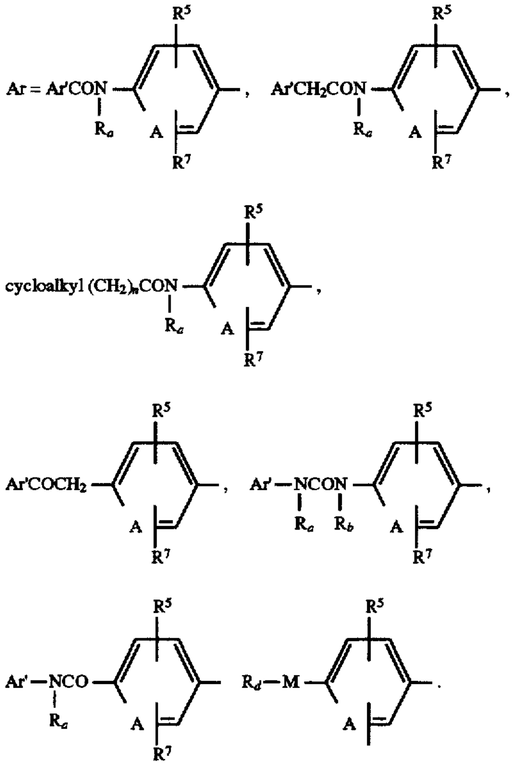

The synthesis of compounds of Formula I wherein $R^3$ is

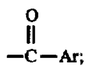

the Ar group is

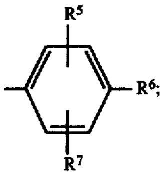

$R^6$ is

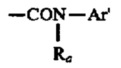

and where Ar' is as previously defined is carried out according to Scheme 8. The azepine compounds are reacted with mono-methyl terephythalyl chloride 23 (prepared from mono-methyl terephthalate and thionyl chloride) in the presence of a tertiary base such as triethylamine in solvents such as dichloromethane, tetrahydrofuran, dioxane, toluene and the like to give derivatives 24. These ester intermediates 24 are hydrolyzed with two to ten equivalents of an alkaline hydroxide such as potassium or sodium hydroxide in aqueous methanol or ethanol to give the corresponding acids after acidification and workup. The free acids are converted to the acid chlorides with thionyl chloride and these acid chloride intermediates 25, reacted with aminoaryl derivatives of formula:

$Ar'-NHR_a$ 26 wherein Ar' and $R_a$ are as previously defined to give compounds 27.

Scheme 8

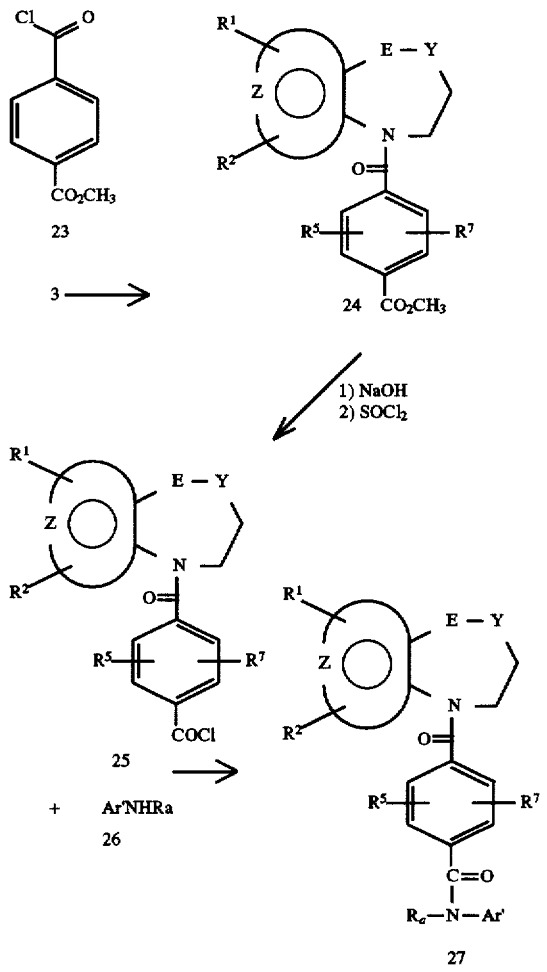

Certain azepines such as compounds 34 and 35 useful for the preparation of compounds of this invention wherein E is a heteroatom, oxygen, sulfur or nitrogen may be synthesized according to Scheme 9. A halogenated heterocycle containing an adjacent nitro group, as exemplified in formuale 28, is reacted with an α-substituted propionic acid or ester in the presence of a suitable base to give an intermediate 30. Reduction of the nitro group and ring closure gives the azepines 32. Reduction of the lactam 32 gives the azepines 33 which contain a fused heterocyclic ring. These intermediates 33 are then acylated with the appropriate aroyl chlorides or an activated aryl carboxylic acids to give directly compounds of this invention or intermediates convertible to find products as hereinbefore described. Representative examples, which may be synthesized according to Scheme 9, are illustrated by structural formulae 34 and35.

Intermediate azepines with a fused heterocyclic ring such as structures of formula 45, 46 and 47, noted as illustrative examples, may be prepared as shown in Scheme 10.

Scheme 9

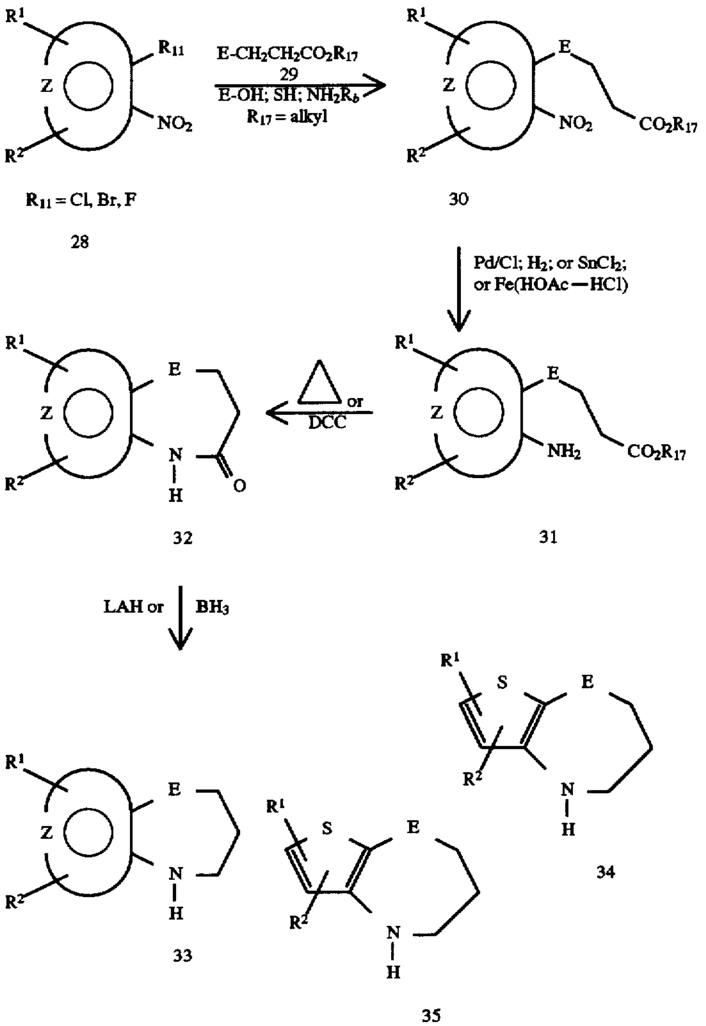

28, 30, 31, 32, 33, 34, 35

As shown in Scheme 10, expansion of a six-membered ring into a seven-membered lactam is carried out by reaction of the ketone derivative 36 with hydroxyl amine to give the oxime derivative which in most cases exists as a mixture of syn and anti forms (structures 37 and 38). The mixture of oximes on reaction with 4-methylbenzenesulfonyl chloride gives either a mixture of oxime O-tosylates or in some cases a single O-tosylate 39. Heating the oxime O-tosylates with potassium acetate in a alcohol-water mixture (such as ethanol-water or n-butanol-water) gives the 7-membered lactam derivatives 41. Reduction of the lactam with diborane, or lithium aluminium hydride (LAH) affords the fused heterocyclic azepines 42. The azepines 42 may be converted to intermediates 43 and 44, which are useful in the preparation of the novel compound of this invention. As hereinbefore stated, the heterocyclic azepines of structural types illustrated by formulae 45–55 may be prepared by the methods exemplified in Scheme 10 or literature methods for ring closures to azepines.

Scheme 10
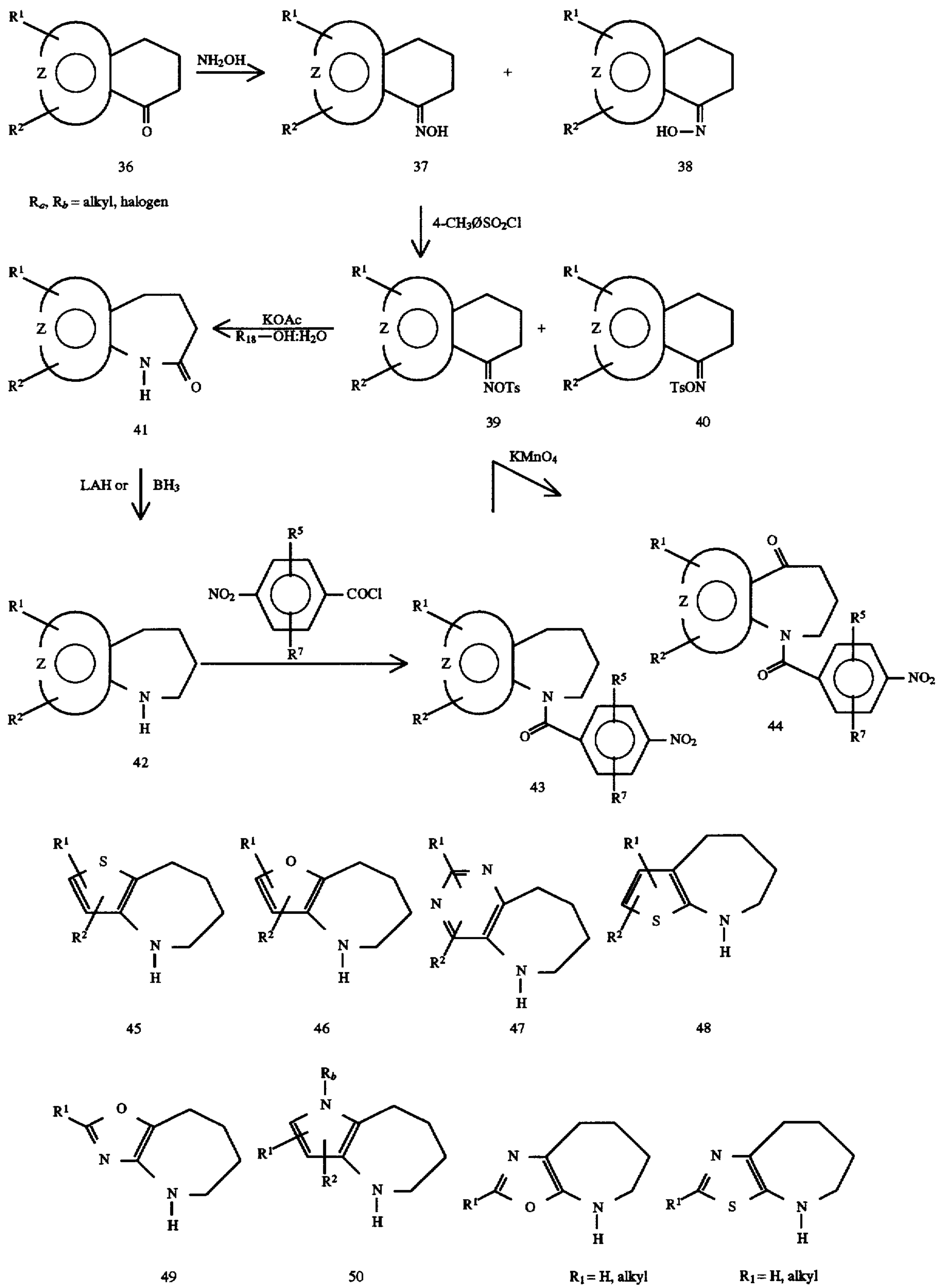
36 37 38
$R_a$, $R_b$ = alkyl, halogen
41 39 40
42 43 44
45 46 47 48
49 50 51 52
$R_1$ = H, alkyl (49)
$R_1$ = H, alkyl (51)
$R_1$ = H, alkyl (52)

-continued
Scheme 10

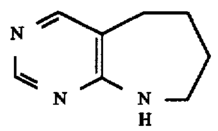
53

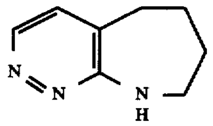
54

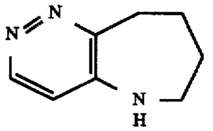
55

Certain of the compounds of this invention wherein $R_a$ is as previously defined are prepared by introduction of the $R_a$ either in a final step or in the penultimate step as shown in Scheme 11. In the derivatives 56 introduction of the $R_a$ substituent ($R_a$ not H) may be carried out in the final step by first forming the anion of the amide function of derivative 56 followed by the appropriate alkylation of the nitrogen atom to give products 57. In derivatives where protection-deprotection is needed the derivatives 56 are converted to the protected intermediates 57a and 57b which on deprotection afford compounds 57. The $R^{21}$ group may be a tertiary butoxy carbonyl group, an acetyl group or other known amine protecting moieties. The $R^{22}$ group may be a tertiary butylcarbonyl group, an acetyl group or other known hydroxy protecting moieties.

Scheme 11

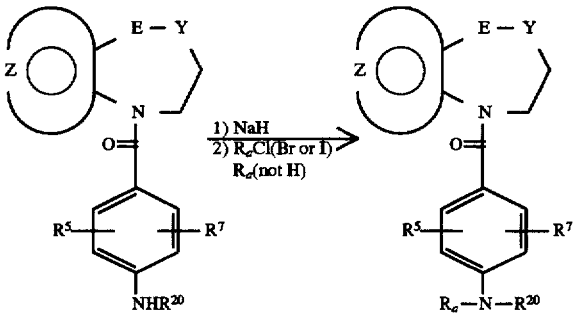

56 57

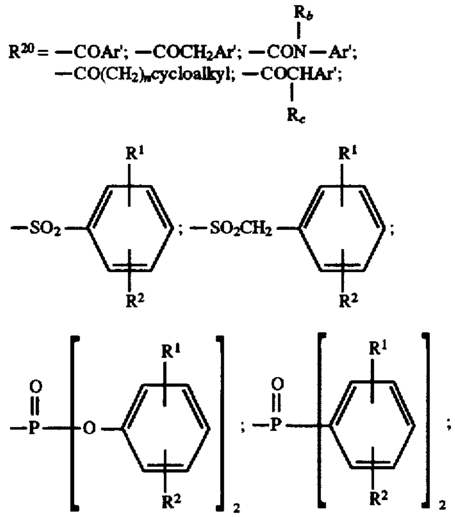

-continued
Scheme 11

$-CO_2$lower alkyl($C_3$-$C_8$); $-CO$lower alkyl($C_3$-$C_8$);

$-SO_2$lower alkyl($C_3$-$C_8$); $-CO_2$-lower alkenyl($C_3$-$C_8$);

COlower alkenyl($C_3$-$C_8$); $-SO_2$lower alkenyl($C_3$-$C_8$)

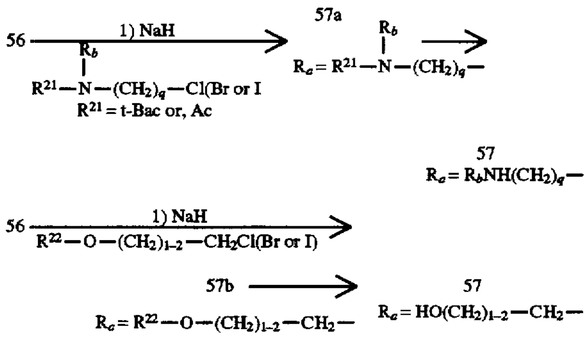

Compounds of this invention represented by the formula 60 may be prepared from the compounds represented by those of formula 59 as shown in Scheme 12. The 6-chloro, bromo or fluoro intermediate 17 is reacted with an amino derivative of the formula $R_aNH_2$ wherein $R_a$ is as hereinbefore defined to give compounds of the formula 59. Reaction of the 6-aminonicotinoyl derivative 59 with an $R^{20}$-chloride wherein $R^{23}$ is defined as shown in Scheme 12 affords compounds of this invention as exemplified by formula 60.

Scheme 12

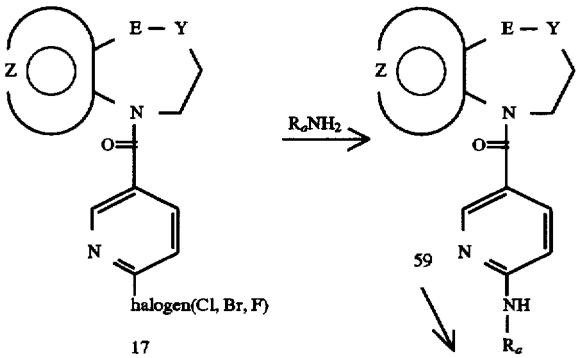

17 59

-continued

Scheme 12

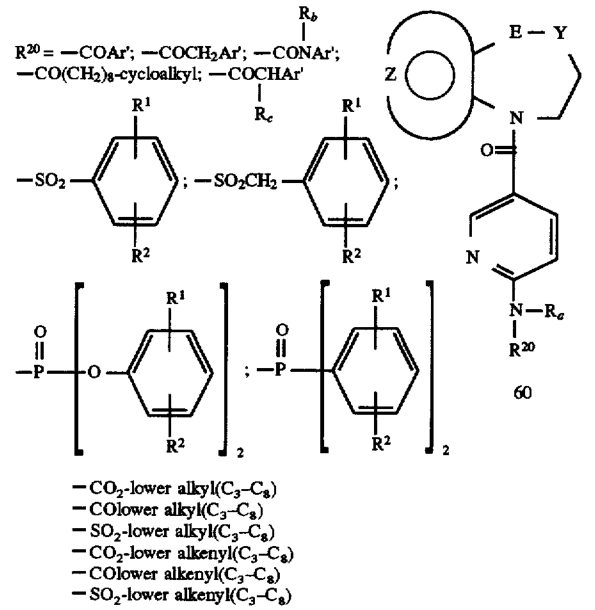

REFERENCE EXAMPLE 1

6,7-Dihydrobenzo[b]thiophen-4(5H)-one, Oxime

To a solution of 4-keto-4,5,6,7-tetrahydrothionaphthene in 260 ml of ethanol is added 27.4 g of hydroxylamine hydrochloride. To the mixture is added 16.5 g of sodium acetate and 66 ml of water and then the mixture is refluxed for 3.5 hours; chilled in an ice bath and filtered. The solid is washed with water and ethanol to give 13 g of solid which is dried at 65° C. under vacuum to give 11.7 g of crystals, m.p. 124°–126° C. (mainly one isomer syn or anti). The filtrate is concentrated under vacuum and extracted with 250 ml of dichloromethane. The extract is washed with 100 ml each of water, brine and then dried ($Na_2SO_4$). The solvent is removed and the solid dried at 65° C. under vacuum to give 32 g of crystals, m.p. 106°–109° C. (mainly one isomer syn or anti).

EXAMPLE 2

6,7-Dihydrobenzo[b]thiophen-4(5H), Oxime-O-tosylate

To a stirred solution of 12.2 g of 6,7-dihydrobenzo[b]thiophen-4(5H)-one, oxime (mixture of isomers) in 26 ml of dry pyridine is cooled to 0° C. is added 15.3 g of p-toluenesulfonyl chloride (all at once). After 5 minutes, a solid separates and the mixture is stirred at 0° C. for 1 hour. To the cold mixture is added 195 ml or 2N HCl and the mixture filtered to give a solid which is washed with water and dried (under vacuum) to give 21.5 g of product as crystals, m.p. 117°–120° C.

REFERENCE EXAMPLE 3

5,6,7,8-Tetrahydro-4H-thieno[3,2-b]azepin-5-one

A mixture of 21.45 g of 6,7-dihydrobenzo[b]thiophen-4(5H)-one, oxime-O-tosylate, 136.1 g of potassium acetate, 528 ml of ethanol and 904 ml of water is refluxed for 22 hours. The mixture is concentrated under vacuum (to remove ethanol), chilled and filtered to give a solid. The solid is washed with water, dried (in air) and recrystallized by dissolving in hot ethyl acetate and diluting the solution with hexane. Chilling and filtering gives 7.1 g of crystals, m.p. 128°–132° C.

REFERENCE EXAMPLE 4

5,6,7,8-tetrahydro-4H-thieno[3,4-b]azepine (1) To a mixture of 4.54 g of lithium aluminum hydride in 400 ml of dry tetrahydrofuran under argon is added dropwise a solution of 10.0 g of 5,6,7,8-tetrahydro-4H-thieno[3,2-b]azepin-5-one in 200 ml of tetrahydrofuran. After the addition, the mixture is heated at 45°–50° C. (exothermic reaction), and cooled to room temperature. The mixture is chilled in an ice bath (0° C.) and 4.5 ml of water added dropwise over 1 hour, followed by the dropwise addition of 4.5 ml of 2N sodium hydroxide and the dropwise addition of 14 ml of water. The mixture is filtered through diatomaceous earth and the filter cake washed with tetrahydrofuran. The filtrate is concentrated to give a solid. The solid is crystallized from hexane to give 5.5 g of off-white crystals, m.p. 66°–68° C.

(2) To a mixture of 21.2 g of 5,6,7,8-tetrahydro-4H-thieno[3,2-b]azepin-5-one in 100 ml of tetrahydrofuran under argon, chilled to 0° C. is added 25.2 ml of a 10.0 molar solution of borane-dimethylsulfide in tetrahydrofuran. The solution is stirred at room temperature for 16 hours and is refluxed for 5 hours. The mixture is cooled to room temperature and 85 ml of methanol added dropwise (exotherm). The solvent is removed and 100 ml of methanol is added (2 times) and after each addition the solvent is removed. To the residual solid (dried under vacuum) is added 126 ml of 2N NaOH and the mixture refluxed 3 hours. The mixture is chilled (2 hours) and extracted with dichloromethane. The extract is dried ($Na_2SO_4$) and the solvent removed to give 15.4 g of brown solid, m.p. 55°–57° C. A sample (3 g) is sublimed to give 2.6 g of crystals, m.p. 64°–65° C.

REFERENCE EXAMPLE 5

4-(4-Nitrobenzoyl)-5,6,7,8-tetrahydo-4H-thieno[3,2-b]azepine

To a solution of 10.71 g of 5,6,7,8-tetrahydro-4H-thieno[3,2-b]azepine and 19.4 ml of triethylamine amine in 150 ml of dichloromethane under argon is added in small portions 4-nitrobenzoyl chloride (exothermic). The mixture is stirred for 3 hours at 25° C. and then washed with water, sodium bicarbonate solution, brine and dried ($Na_2SO_4$). The solvent is removed, the residue dried under vacuum and recrystallized by dissolving in hot ethyl acetate and diluting with hexane. Chilling overnight and filtering gives 16 g of light brown crystals, m.p. 141°–142° C.

REFERENCE EXAMPLE 6

4-(4-Nitrobenzoyl)-4,5,6,7-tetrahydro-8H-thieno[3,2-b]azepin-8-one

To a solution of 9.0 g of 4-(4-nitrobenzoyl)-5,6,7,8-tetrahydro-4H-thieno[3,2-b]azepine in 713 ml of acetone is added 6.74 g of $MgSO_4$ and 351 ml of water followed by 8.2 g of $KMnO_4$ and heating at 70° C. for 18 hours. Another 6.24 g of $MgSO_4$ and 8.2 g of $KMnO_4$ is added and heating continued at 70° C. for 8 hours. An additional 6.24 g of $MgSO_4$ and 8.2 g of $KMnO_4$ is added and heating continued at 70° C. for 18 hours. The reaction mixture is filtered through diatomaceous earth and the cake washed with acetone and 500 ml of methylene chloride. The combined filtrates are evaporated in vacuo to a residue which is washed with water and air dried to give 5.7 g of a solid. The solid is crystallized from ethyl acetate to give 5.1 g of off white solid, m.p. 184°–186° C.

REFERENCE EXAMPLE 7

4-(4-Aminobenzoyl)-4,5,6,7-tetrahydro-8H-thieno[3,2-b]azepin-8-one

To a mixture of 2.0 g of 4-(4-nitrobenzoyl)-4,5,6,7-tetrahydro-8H-thieno-[3,2-b]azepin-8-one in 40 ml of glacial acetic acid is added 20 ml of 6N-hydrochloric acid. The mixture is cooled and 3.53 g of iron powder added in portions. The mixture is allowed to warm to room temperature and is heated at 70°–80° C. for 1 hour and then cooled to 0° C. To mixture is basified with 10N NaOH (pH 14) and extracted with 200 ml of ethyl acetate. The aqueous layer is again extracted with 200 ml of ethyl acetate and the extracts combined. The combined extract is washed with 100 ml each of $H_2O$ and brine and dried ($Na_2SO_4$). The extract is filtered through a thin pad of hydrous magnesium silicate and the filtrate concentrated to give a solid which is crystallized from ethyl acetate-hexane to give 1.24 g of crystals, m.p. 216°–218° C.

REFERENCE EXAMPLE 8

2-Chloro-4-(4-nitrobenzoyl)-5,6,7,8-tetrahydro-4H-thieno[3,2-b]azepine

A solution of 6.04 g of 4-(4-nitrobenzoyl)-5,6,7,8-tetrahydro-4H-thieno[3,2-b]azepine in 40 ml of tetrahydrofuran is cooled to 0° C. and 5.34 g of N-chlorosuccinimide added in portions. After the addition, the mixture is heated at 70° C. overnight. The mixture is concentrated, diluted with 300 ml of dichloromethane and the mixture washed with 100 ml each of saturated $K_2CO_3$ solution, $H_2O$, 1N HCl and brine. The organic layer is dried ($Na_2SO_4$) and filtered through a thin pad of hydrous magnesium silicate. The filtrate is concentrated and the residue chromatographed by HPLC on silica gel (2-columns) with a Waters-Prep-500 instrument and the solvent system ethyl acetate-dichloromethane (1:1) containing 2% diethylether. The middle cuts are combined and concentrated to give 0.135 g of 2,3-dichloro-4-(4-nitrobenzoyl)-5,6,7,8-tetrahydro-4H-thieno-[3,2-b]azepine, m.p. 140°–142° C. The latter cuts are combined, concentrated and the residue crystallized from ethyl acetate-hexane to give 2.8 g of crystals, 119°–120° C.

REFERENCE EXAMPLE 9

2-Chloro-4-(4-aminobenzoyl)-5,6,7,8-tetrahydro-4H-thieno[3,2-b]azepine

To a solution of 2.6 g of 2-chloro-4-(4-aminobenzoyl)-5,6,7,8-tetrahydro-4H-thieno[3,2-b]azepine in a mixture of 52 ml of acetic acid and 26 ml of 6N HCl, cooled to 0° C., is added 4.32 g of iron powder in small portions. After the addition, the mixture is heated at 70°–80° C. for 2 hours. The mixture is cooled in an ice bath (0° C.) and made basic with 10N NaOH (pH 14). The mixture is extracted with 250 ml of ethyl acetate and then 150 ml of ethyl acetate. The combined extract is washed with 100 ml each of $H_2O$ and brine. The extract is dried ($Na_2SO_4$) and filtered through a thin pad of hydrous magnesium silicate. The filtrate is concentrated to dryness and the residue crystallized from ethyl acetate-hexane to give 1.7 g of off-white crystals, m.p. 146°–149° C.

REFERENCE EXAMPLE 10

2-Chloro-4-(4-nitrobenzoyl)-4,5,6,7-tetrahydro-8H-thieno[3,2-b]azepin-8-one

To a stirred solution of 0.336 g of 4-(4-nitrobenzoyl)-4,5,6,7-tetrahydro-8H-thieno[3,2-b]azepin-8-one in 36 ml of acetone-water (2:1) is added 0.21 g of anhydrous magnesium sulfate and 0.275 g of potassium permanganate. The mixture is heated at 70° C. overnight. An additional 0.275 g of potassium permanganate and 0.21 g of magnesium sulfate is added and the mixture heated at 70° C. for 6 hours. An additional 0.275 g of potassium permanganate and 0.21 g of magnesium sulfate is added and the mixture stirred and heated at 70° C. for 24 hours. The hot mixture is filtered and the filtrate evaporated. The residue is heated in a few ml of ethyl acetate, cooled and filtered to give 0.20 g of product as a solid. The reaction is repeated on 10 times the scale to give 1.3 g of off-white crystals, m.p. 165°–168° C.

REFERENCE EXAMPLE 11

4-(4-Aminobenzoyl)-5,6,7,8-tetrahydro-4H-thieno[3,2-b]azepine

A solution of 9.97 g of 4-(4-nitrobenzoyl)-5,6,7,8-tetrahydro-4H-thieno[3,2-b]azepine in 110 ml of glacial acetic acid and 0.997 g of 10% palladium-on-carbon is hydrogenated in a Parr hydrogenator under 30–50 lb. of pressure for 4.5 hours. The mixture is filtered through a pad of diatomaceous earth and the filtrate concentrated to dryness under vacuum. The gummy residue (8.1 g) is purified by HPLC on a Waters-Prep-500 instrument with silica gel and ethyl acetate-hexane (1:1) as solvent. Fractions containing product are combined and the solvent removed. The residue is crystallized to give 4.0 g of crystals, m.p. 168°–172° C.

REFERENCE EXAMPLE 12

Methyl 4-[2-(2-chlorophenyl)-2-cyano-2-(4-morpholinyl)ethyl]benzoate

A 0.876 g sample of 60% sodium hydride in oil is washed with hexane followed by the addition of 60 ml of dry N,N-dimethylformamide. The reaction mixture is stirred for 1 hour under argon at room temperature after the addition of 4.73 g of α-(2-chlorophenyl)-4-morpholineacetonitrile. To the reaction mixture is added 4.58 g of methyl 4-(bromomethyl)benzoate and stirring continued for 3 hours. Several drops of acetic acid is added to ice water and the reaction quenched. The pH is 3–4 and saturated $NaHCO_3$ added to adjust the pH to 6–7. Upon cooling a solid forms which is filtered, washed with water and dried to give 5.92 g of yellow solid. Crystallization from methylene chloride-hexane gives 2.10 g of the desired product as a crystalline solid, m.p. 116°–118° C.

REFERENCE EXAMPLE 13

Methyl 4-[2-(2-chlorophenyl)-2-oxoethyl]benzoate

A mixture of 1.0 g of methyl [4-(2-chlorophenyl)-2-cyano-2-(4-morpholinyl)ethyl]benzoate and 14 ml of acetic acid and 6 ml of water is heated at reflux for 20 minutes then poured over crushed ice. After stirring for 15 minutes, the resulting solid is collected, washed with water and air dried to give 0.63 g of tan solid, m.p. 40°–42° C.

REFERENCE EXAMPLE 14

4-[2(2-Chlorophenyl)-2-oxoethyl]benzoic acid

A mixture of 18.78 g of methyl 4-[2-(2-chlorophenyl)-2-oxoethyl]benzoate in 288.8 ml of $CH_3OH$, 72.2 ml of water and 5.2 g of NaOH is refluxed for 3 hours then acidified with 2 N citric acid. The reaction mixture is evaporated in vacuo to remove the $CH_3OH$. The aqueous phase is extracted with $CH_2Cl_2$ and acidified with 1N HCl. The resulting solid is collected and dried under vacuum to give 17.27 g of the desired product, m.p. 168°–172° C.

REFERENCE EXAMPLE 15

Methyl 4,5,6,7-tetrahydro-4-oxo-3-benzofurancarboxylate

To a solution of 2.11 g of 4-oxo-4,5,6,7-tetrahydrobenzo[b]furan-3-carboxylic acid in 100 ml of methanol is added 202 mg of p-toluenesulfonic acid hydrate and the mixture heated at reflux for 24 hours. The reaction mixture is cooled to room temperature and the methanol concentrated in vacuo to a residue. The residue is dissolved in 100 ml of ethyl acetate and washed with 30 ml of saturated sodium bicarbonate and 30 ml of brine. The organic layer is dried with $Na_2SO_4$, filtered and the filtrate concentrated in vacuo to a residue which is crystallized from ethyl acetate-hexane to give 1.75 g of the desired product as a white crystalline solid, m.p. 100°–102° C.

REFERENCE EXAMPLE 16

Methyl 5,6,7,8-tetrahydro-5-oxo-4H-furo[3,2-b]azepine-3-carboxylate

To a mixture of 1.0 g of methyl 4,5,6,7-tetrahydro-4-oxo-3-benzofurancarboxylate and 502 mg of sodium azide in 5 ml of chloroform is added dropwise at 32°–36° C. under argon 1.4 ml of sulfuric acid. The reaction mixture is stirred at room temperature for 24 hours. The reaction mixture is diluted with 14 ml of water and rendered alkaline with $NH_4OH$ and extracted with chloroform. The separated organic layer is washed with water, brine and dried with $Na_2SO_4$ and concentrated in vacuo to give 1.0 g of the desired product as a white solid.

REFERENCE EXAMPLE 17

(E) 4,5,6,7-Tetrahydro-4-[[[(4-methylphenyl)sulfonyl]oxy]imino]-3-benzofurancarboxylic acid To a partial solution of 2.8 g of (E)-4,5,6,7-tetrahydro-4-(hydroxyimino)-3-benzofurancarboxylic acid in 7 ml of pyridine is added portionwise at 0° C., 3.01 g of p-toluene sulfonyl chloride under argon. The mixture is stirred for 1 hour then diluted with 40 ml of cold 1N HCl, filtered, washed with water and dried with $Na_2SO_4$. The filtrate is concentrated in vacuo to give 4.78 g of the desired product as an off-white solid, m.p. 155°–165° C.

REFERENCE EXAMPLE 18

5,6,7,8-Tetrahydro-5-oxo-4H-furo[3,2-b]azepine-3-carboxylic acid

A mixture of 1.0 g of (E)-4,5,6,7-tetrahydro-4-[[[(4-methylphenyl)sulfonyl]oxy]imino]-3-benzofurancarboxylic acid, 5.9 g of potassium acetate, 23 ml of ethanol and 39 ml of water is heated at reflux for 48 hours. The reaction mixture is concentrated in vacuo, 80 ml of methylene chloride added and the separated organic layer washed with water, brine and dried with $Na_2SO_4$. The organic layer is concen-trated in vacuo to a solid which is purified by chroma-tography on a preparative silica gel plate by elution with 0.5% acetic acid in ethyl acetate. The eluted band is washed with 1% acetic acid in ethyl acetate. The organic layer is dried with $Na_2SO_{04}$ and concentrated in vacuo to give 200 mg of off-white solid which is crystallized from ethyl acetate-hexane to give 165 mg of the desired product as a white solid.

REFERENCE EXAMPLE 19

(E) and (Z)-4,5,6,7-Tetrahydro-4-(hydroxyimino)-3-benzofurancarboxylic acid

To a solution of 30.0 g of 4,5,6,7-tetrahydro-4-oxo-3-benzofurancarboxylic acid in 225 ml of ethanol is added 22.97 g of hydroxylamine hydrochloride, followed by 18.10 g of sodium acetate and 55 ml of water. The reaction mixture is heated at reflux for 2.5 hours and concentrated in vacuo to a residue which is diluted with 600 ml of ethyl acetate, washed with 2×200 ml of water, brine and dried over $Na_2SO_4$. The organic layer is concentrated in vacuo to a residue which is dried under vacuum to give 31.0 g of the desired product as a solid.

REFERENCE EXAMPLE 20

(E) and (Z)-6,7-Dihydro-4-(5H)benzofuranone, O-[(4-methylphenyl)sulfonyl]oxime

To a partial solution of 28.0 g of (E) and (Z)-4,5,6,7-tetrahydro-4-(hydroxyimino)benzofuran in 54 ml of pyridine is added portionwise at 0° C., 38.8 g of p-toluene sulfonyl chloride under argon. The mixture is stirred for 1 hour then diluted with 600 ml of ethyl acetate and 400 ml of cold 2N HCl. The organic layer is washed with 200 ml of water and 200 ml of brine, and dried with $Na_2SO_4$. The filtrate is concentrated in vacuo to give 50 g of the desired product as a solid. Crystallization from ethyl alcohol by allowing to stand at room temperature gives 19.9 g of off-white needles, m.p. 123°–125° C. The filtrate is allowed to stand and the crystals collected and dried to give 10.0 g of the desired product as an off-white solid, 83°–85° C.

REFERENCE EXAMPLE 21

4-(2-Chloro-4-nitrobenzoyl)-5,6,7,8-tetrahydro-4H-thieno[3,2-b]azepine

To a solution of 15.0 g of 5,6,7,8-tetrahydro-4H-thieno[3,2-b]azepine in 150 ml of dichloromethane cooled to 0° C. is added 27.2 ml of triethylamine. After stirring 5 minutes, a solution of 28.0 g of 2-chloro-4-nitrobenzoyl chloride in 140 ml of dichloromethane is added slowly. The solution is stirred at room temperature overnight, diluted with 450 ml of dichloromethane and the solution washed with 200 ml each of water, 2N citric acid, 1M sodium bicarbonate and brine. The organic layer is dried over $N_2SO_4$, filtered through a thin pad of hydrated magnesium silicate and the filtrate concentrated under vacuum. The residue is crystallized from ethyl acetate to give 24.3 g of off-white crystals, m.p. 131°–134° C.

REFERENCE EXAMPLE 22

4-(2-Chloro-4-aminobenzoyl)-5,6,7,8-tetrahydro-4H-thieno[3,2-b]azepine

A mixture of 5.0 g of 4-(2-chloro-4-nitrobenzoyl)-5,6,7,8-tetrahydro-4H-thieno [3,2 -b]azepine, 16.8 g of stannous chloride dihydrate in 184 ml of ethanol is heated at 80° C. under argon for 1 hour. The solution is cooled in an ice bath and made basic by the slow careful addition of 1M $NaHCO_3$ (ca. 380 ml). The mixture is stirred for 1 hour at room temperature and extracted with 400 ml of ethyl acetate. The aqueous layer is extracted with an additional 250 ml of ethyl acetate. The extracts are combined and washed with 300 ml of brine, dried ($Na_2SO_4$) and filtered through a thin pad of hydrous magnesium silicate. The filtrate is concentrated under vacuum to give a white solid which is recrystallized from ethyl acetate to give 4.23 g of off-white crystals, m.p. 176°–179° C.

REFERENCE EXAMPLE 23

4-(2-Chloro-4-nitrobenzoyl)-4,5,6,7-tetrahydro-8H-thieno[3,2-b]azepine-8-one

To a solution of 2.02 g of 4-(2-chloro-4-nitrobenzoyl)-4,5,6,7,8-tetrahydro-4H-thieno[3,2-b]-azepine in 144 ml of acetone is added 1.56 g of magnesium sulfate, 72 ml of water and 1.89 g of potassium permanganate. The mixture is stirred and heated at 70°–75° C. for 4 hours. An additional amount of magnesium sulfate (1.56 g) and potassium permanganate (1.89 g) is added and the mixture stirred and heated at 75° C. for 16 hours. Magnesium sulfate (1.56 g) and potassium permanganate (1.89 g) are added and the mixture stirred and heated at 75° C. for 5 hours. The mixture is filtered through diatomaceous earth and the filter cake washed with acetone and dichloromethane. The filtrate is concentrated and the residue (1.4 g) is heated with ethyl acetate, the mixture (with insoluble solid) cooled and filtered to give 1.0 g of product as a solid. The solid is washed with water and dried to give crystals, m.p. 180°–185° C.

REFERENCE EXAMPLE 24

4-(2-Chloro-4-nitrobenzoyl)-8-hydroxy-5,6,7,8-tetrahydro-4H-thieno[3,2-b]azepine To a solution of 1.0 g of 4-(2-chloro-4-nitrobenzoyl)-4,5,6,7-tetrahydro-8H-thieno[3,2-b]azepin-8-one in 10 ml of tetrahydrofuran is added 1 ml of ethanol and the mixture cooled to 0° C. To the mixture is added 0.129 g of sodium borohydride in portions and the mixture is stirred at 0° C. for 1 hour. To the mixture is added slowly 4.2 ml of saturated ammonium chloride solution at 0° C. After stirring at room temperature for 10 minutes, the solvent is removed under vacuum and 80 ml of ethyl acetate added to the residue. The mixture is washed with 20 ml each of $H_2O$, 2N citric acid, 1M $NaHCO_3$ and brine. The organic layer is dried ($Na_2SO_4$) and filtered through a thin pad of hydrous magnesium silicate. The filtrate is concentrated under vacuum to give the product as a white glass.

REFERENCE EXAMPLE 25

4-(2-Chloro-4-nitrobenzoyl)-5,6-dihydro-4H-thieno-[3,2-b]azepine

A solution of 0.90 g of 4-(2-chloro-4-nitrobenzoyl)-8-hydroxy-5,6,7,8-tetrahydro-4H-thieno[3,2-b]azepine in 5 ml of dichloromethane cooled to −10° C. is added under argon 533 μl of triethylamine and dropwise 296 μl of methanesulfonyl chloride. After one hour the cooling bath is removed and the mixture allowed to stand at room temperature overnight. The mixture is diluted with 10 ml of dichloromethane and 5 ml of water. The organic layer is separated, dried ($Na_2SO_4$) and filtered through a thin pad of hydrous magnesium silicate. The filtrate is concentrated under vacuum to give an oil which is crystallized by adding hexane. Filtration gives light yellow crystals (0.80 g).

REFERENCE EXAMPLE 26

5-Fluoro-2-methylbenzoyl chloride

A mixture of 8.0 g of 5-fluoro-2-methylbenzoic acid and 52 ml of thionyl chloride is heated on a steam bath for 1 hour. The volatiles are removed under vacuum and two times 50 ml of toluene is added and the solvent removed under vacuum to give 8.5 g of product as a gum.

REFERENCE EXAMPLE 27

2-Chloro-5-(methylthio)benzoyl chloride

A mixture of 2.03 g of 2-chloro-5-(methylthio)benzoic acid and 10 ml of thionyl chloride is heated on a steam bath for 1 hour. The volatiles are removed under vacuum and 20 ml of toluene added and removed under vacuum (2 times) to give 2.2 g of brown needles.

REFERENCE EXAMPLE 28

2-Chloro-4-nitrobenzoyl chloride

As described for Reference Example 26, 25 g of 2-chloro-4-nitrobenzoic acid is reacted with thionyl chloride (124 ml) to give the product (27.0 g) as a brown oil.

REFERENCE EXAMPLE 29

2-Chloro-5-nitrobenzoyl chloride

As described for Reference Example 26, 5.0 g of 2-chloro-5-nitrobenzoic acid is reacted with 50 ml of thionyl chloride to give 5.6 g of the product as an off-white solid.

REFERENCE EXAMPLE 30

2,3-Dimethylbenzoyl chloride

As described for Reference Example 26, 3.0 g of 2,3-dimethylbenzoic acid is reacted with 40 ml of thionyl chloride to give 3.2 g of the product as a colorless oil.

REFERENCE EXAMPLE 31

2-Chlorobenzoyl chloride

As described for Reference Example 26, 3.13 g of 2-chlorobenzoic acid is reacted with 40 ml of thionyl chloride to give 3.32 of product as an off-white semi solid.

REFERENCE EXAMPLE 32

4-(2-Chloro-4-aminobenzoyl)-5,6-dihydro-4H-thieno-[3,2-b]azepine

To a solution of 2.36 g of $SnCl_2.2H_2O$ in 13 ml of ethanol is added 0.70 g of 4-(2-chloro-4-nitrobenzoyl)-5,6-dihydro-4H-thieno[3,2-b]azepine. The mixture is heated at 75° C. for one hour, cooled to room temperature and concentrated under vacuum to 10 ml. The mixture is chilled in an ice bath and 1M $NaHCO_3$ added slowly. The mixture is extracted with 100 ml ethyl acetate and then with 80 ml of ethyl acetate. The extracts are combined, washed with brine and dried ($Na_2SO_4$). The extract is passed through a thin pad of hydrous magnesium silicate and the pad washed with ethyl acetate. The filtrate is concentrated to give a solid which is crystallized from ethyl acetate to give white crystals, m.p. 192°–200° C.

REFERENCE EXAMPLE 33

4-[(2-Methylbenzoyl)amino]benzoic acid

A mixture of 43.42 g (0.26 mol) of ethyl 4-aminobenzoate and 40.8 g (0.26 mol) of 2-methylbenzoyl chloride in 150 ml of dichloromethane is cooled in an ice bath and 26.56 g (0.26 mol) of triethylamine is added dropwise. After the addition, the solution is stirred at room temperature overnight. The mixture is poured into water and the organic layer separated. The organic layer is washed with water, 1N HCl, 1M $NaHCO_3$ and dried ($Na_2SO_4$). The solvent is removed and the solid slurried with ethyl acetate and filtered to give 57 g of ethyl 4-[(2-methylbenzoyl)amino]benzoate as crystals, m.p. 110°–115° C.

A mixture of 50.7 g (0.20 mol) of the preceding compound, 280 ml of ethanol and 55 ml of 10N NaOH is refluxed for 5 minutes. The mixture is cooled to room temperature, diluted with 200 ml of water and acidified with concentrated hydrochloric acid (pH 1–2). The mixture is filtered and the solid washed with water and dried to give 51 g of product as white crystals, m.p. 270°–275° C.

REFERENCE EXAMPLE 34

4-[(2-Methylbenzoyl)amino]benzoyl chloride

A mixture of 10.3 g of 4-[(2-methylbenzoyl)amino] benzoic acid and 32 ml of thionyl chloride is refluxed for 1.5 hours. The solution is concentrated under vacuum. Toluene is added and the solvent removed under vacuum. Toluene is added and the mixture chilled and filtered to give a yellow solid, m.p. 135°–141° C.

REFERENCE EXAMPLE 35

4-[(2,6-Dimethoxybenzoyl)amino]benzoic acid

A mixture of 2 g (10 mmol) of 2,6-dimethoxybenzoyl chloride, 1.65 g (10 mmol) of ethyl 4-aminobenzoate, 1.11 g of triethylamine and 61 mg of 4-dimethylaminopyridine in 10 ml of dichloromethane is refluxed for 20 hours. The mixture is diluted with water and the organic layer separated. The organic layer is washed with water, 1N HCl, 1N $Na_2CO_3$, brine and dried ($Na_2SO_4$). The solvent is removed to give a solid which is crystallized from ethyl acetate to give 1.22 g of ethyl 4-[(2,6-dimethoxybenzoyl)amino] benzoate as crystals, m.p. 183°–185° C.

A mixture of 3.88 g (11.79 mmol) of the preceding compound, 17.3 ml of 2N NaOH and 20 ml of methanol is stirred at room temperature overnight. Methanol (30 ml) and water (10 ml) are added and the solution refluxed for ½ hour. The solvents are removed under vacuum and the residual solid triturated with ether and the ether decanted. The solid is dissolved in 30 ml of water and acidified with 2N HCl (pH 3). The mixture is filtered, the solid washed with water and dried at 60° C. under vacuum to give 3.0 g of solid, m.p. 236°–240° C.

REFERENCE EXAMPLE 36

4-[(4-Pyridinylcarbonyl)amino]benzoic acid

To a cooled mixture of 1.78 g (0.01 mol) of isoniconinoyl chloride hydrochloride in 5 ml of dichloromethane is added 2.52 g (0.025 mol) of triethylamine. To the solution is added a solution of 1.65 g of ethyl 4-aminobenzoate in 5 ml of dichloromethane. After stirring at room temperature overnight, 50 mg of 4-dimethylaminopyridine is added and the mixture is refluxed for 24 hours. The mixture is poured into water and filtered to give 3.4 g of brown solid. A 0.50 g sample is triturated with ethyl acetate to give 0.37 g of ethyl 4-[(4-pyridinylcarbonyl)amino]benzoate as yellow crystals, m.p. 143°–145° C.

REFERENCE EXAMPLE 37

2-Methylfurane-3-carbonyl chloride

A mixture of 4.0 g of methyl-2-methylfurane-3-carboxylate, 30 ml of 2N NaOH and 15 ml methanol is refluxed for 1.5 hours. The solvent is removed under vacuum to give a solid. The solid is extracted with dichloromethane (discarded). The solid is dissolved in water and the solution acidified with 2N citric acid to give a solid. The solid is washed with water and dried to give crystals 1.05 g of crystals of 2-methylfuran-3-carboxylic acid. The preceding compound (0.95 g) and 3 ml of thionyl chloride is refluxed for 1 hour. The solvent is removed, toluene added (20 ml, three times) and the solvent removed to give the product as an oil.

REFERENCE EXAMPLE 38

4-[N-Methyl-N-(2-methylbenzoyl)amino]benzoic acid

A sample of 1.51 g of sodium hydride (60% in oil) is washed with hexane under argon to remove the oil. To the washed sodium hydride is added 5 ml of N,N-dimethylformamide. To this mixture is added dropwise a solution of 8.69 g of ethyl 4-[(2-methylbenzoyl)amino] benzoate in 20 ml of dimethylformamide. The mixture is stirred at room temperature for 0.5 hour and then 5.23 g of methyl iodide is added. The mixture is stirred at room temperature for 16 hours. The mixture is diluted with water and extracted with dichloromethane. The extract is dried ($Na_2SO_4$), concentrated to reduce the volume and the solution filtered through a thin pad of hydrous magnesium silicate. The filtrate is concentrated in vacuo to give 11 g of an oil (1:1 mixture of product and N,N-dimethylformamide). The preceding product, ethyl 4-[N-methyl-N-(2-methylbenzoyl)amino]benzoate, (11 g) is dissolved in 30 ml of methanol and 25 ml of 2N NaOH added. The mixture is refluxed for 2 hours and the solvent removed. The residue is extracted with ether (discard) and the remaining residue dissolved in 50 ml of water. The basic solution is acidified with 2N citric acid and the solid filtered off and washed with water. The product is air dried to give 6.72 g of crystals, m.p. 187°–190° C.

REFERENCE EXAMPLE 39

4-[N-Methyl-N-(2-methylbenzoylamino]benzoyl chloride

A solution of 6.72 g of 4-[N-methyl-N-(2-methylbenzoyl) amino]benzoic acid in 20 ml of thionyl chloride is refluxed for one hour. The volatiles are removed in vacuo. Toluene is added to the residue and then the toluene removed in vacuo (repeated several times) to give the 7.3 g of product as a brown oil.

As described for Reference Example 38, but substituting the appropriate ethyl 4-[(N-aroyl)amino]benzoate, the following compounds are prepared.

REFERENCE EXAMPLE 40

4-[N-Methyl-N-(2-chlorobenzoyl)amino] benzoic acid

REFERENCE EXAMPLE 41

N-[N-Methyl-N-(2,5-dichlorobenzoyl)amino] benzoic acid

REFERENCE EXAMPLE 42

N-[N-Methyl-N-(2,4-dichlorobenzoyl)amino] benzoic acid

REFERENCE EXAMPLE 43

4-[N-Methyl-N-(2-chloro-4-methylbenzoyl) amino]benzoic acid

REFERENCE EXAMPLE 44

4-[N-methyl-N-(2-methyl-4-chlorobenzoyl) amino]benzoic acid

REFERENCE EXAMPLE 45

4-[N-Methyl-N-(2,4-dimethylbenzoyl)amino] benzoic acid

REFERENCE EXAMPLE 46

4-[N-Methyl-N-(2,3-dimethylbenzoyl)amino] benzoic acid

REFERENCE EXAMPLE 47

4-[N-Methyl-N-(2-methoxybenzoyl)amino] benzoic acid

REFERENCE EXAMPLE 48

4-[N-Methyl-N-(2-trifluoromethoxybenzoyl) amino]benzoic acid

REFERENCE EXAMPLE 49

4-[N-Methyl-N-(2,4-dimethoxybenzoyl)amino] benzoic acid

REFERENCE EXAMPLE 50

4-[N-Methyl-N-(2-methoxy-4-chlorobenzoyl) amino]benzoic acid

REFERENCE EXAMPLE 51

4-[N-Methyl-N-(2-methylthiobenzoyl)amino] benzoic acid

REFERENCE EXAMPLE 52

4-[N-Methyl-N-(2-methylthiophen-3-ylcarbonyl) amino]benzoic acid

REFERENCE EXAMPLE 53

4-[N-Methyl-N-(3-methylthiophene-2-ylcarbonyl) amino]benzoic acid

REFERENCE EXAMPLE 54

4-[N-Methyl-N-(2-methylfuran-3-ylcarbonyl) amino]benzoic acid

REFERENCE EXAMPLE 55

4-[N-Methyl-N-(3-methylfuran-2-ylcarbonyl] amino]benzoic acid

REFERENCE EXAMPLE 56

4-[N-Methyl-N-(phenylacetyl)amino]benzoic acid

REFERENCE EXAMPLE 57

4-[N-Methyl-N-(2-chlorophenylacetyl)amino] benzoic acid

REFERENCE EXAMPLE 58

4-[N-Methyl-N-(2-methoxyphenylacetyl)amino] benzoic acid

REFERENCE EXAMPLE 59

4-[N-Methyl-N-(2-methylphenylacetyl)amino] benzoic acid

REFERENCE EXAMPLE 60

4-[N-Methyl-N-(cyclohexylcarbonyl)amino] benzoic acid

REFERENCE EXAMPLE 61

4-[N-Methyl-N-(3-cyclohexenecarbonyl)amino] benzoic acid

REFERENCE EXAMPLE 62

4-[N-Methyl-N-(cyclohexylacetyl)amino] benzoic acid

REFERENCE EXAMPLE 63

4,5,6,7-Tetrahydro-4-(4-nitrobenzoyl)-8H-thieno[3, 2-b]azepin-8-one, 8-oxime

To a suspension of 2.0 g of 4,5,6,7-tetrahydro-4-(4-nitrobenzoyl)-8H-thieno[3,2-b]azepin-8-one in 7 ml of ethanol is added 0.681 g of hydroxylamine, hydrochloride; 0.400 g of sodium acetate and 2 ml of water. The mixture is refluxed for 2 hours, chilled, filtered and the solid washed with water. The solid is dried at room temperature under vacuum to give 2.0 g of yellow solid.

REFERENCE EXAMPLE 64

4,5,6,7-Tetrahydro-4-(4-aminobenzoyl)-8H-thieno[3, 2-b]azepin-8-one, 8-oxime

A mixture of 1.0 g of 4,5,6,7-tetrahydro-4-(4-nitrobenzoyl)-8H-thieno[3,2-b]azepin-8-one, 8-oxime, 6.8 g of $SnCl_2.2H_2O$ and 14 ml of ethanol is refluxed for 2 hours. The mixture is chilled (ice bath) and 1M NaHCO3 is added until the pH is approximately 8. The mixture is stirred for 1 hour and then extracted with ethyl acetate. The extract is washed with brine, dried ($Na_2SO_4$) and the solvent removed under vacuum. The residue is chromatographed on prep-plates of silica gel with ethyl acetate-hexane (2:1) as solvent to give a solid. Crystallization from ethyl acetate gives 0.37 g of off-white crystals, m.p. 156°–160° C.

REFERENCE EXAMPLE 65

8-Amino-4-(4-nitrobenzoyl)-5,6,7,8-tetrahydro-4H-thieno[3,2-b]azepine

The procedure from *Synthetic Communications* 18(8) 777–782(1988) is followed.

To a mixture of 0.50 g of 5,6,7,8-tetrahydro-4-(4-nitrobenzoyl)-8H-thieno[3,2-b]azepin-8-one, 8-oxime, 0.50 g of ammonium acetate and 0.283 g of sodium cyanoborohydride in 25 ml of methanol is added dropwise 2.54 ml of titanium trichloride (20% aqueous solution) while stirring. The mixture is worked-up and the process repeated several times to give the product as a solid.

REFERENCE EXAMPLE 66

N-[4-[(5,6,7,8-Tetrahydro-8-[[(2-methylbenzoyl) oxy]imino]-4H-thieno[3,2-b]azepin-4-yl)carbonyl] phenyl]-2-methylbenzamide To a cooled (0° C.) solution of 0.18 g of 4,5,6,7-tetrahydro-4-(4-aminobenzoyl)-8H-thieno[3,2-b]azepine-8- one, 8-oxime and 261 μl of triethylamine in 4 ml of dichloromethane is added 204 μl of 2-methylbenzoyl chloride. The mixture is stirred under argon for 16 hours and diluted with 40 ml of dichloromethane. The mixture is washed with 20 ml each of $H_2O$, 2N citric acid, brine and dried ($Na_2SO_4$). The solvent is removed and the residue chromatographed on silica gel with ethyl acetate-hexane as solvent to give 0.22 g of white amorphous solid

REFERENCE EXAMPLE 67

N-[4-[(5,6,7,8-Tetrahydro-8-oxo-4H-thieno[3,2-b]azepin-4-yl)carbonyl]phenyl]-2-methylbenzamide, 8-oxime To a stirred solution of Reference Example 66 (0.20 g) in 4 ml of methanol is added 0.93 ml of 1N NaOH. The mixture is stirred overnight and concentrated under vacuum. The residue is partitioned between water and ethyl acetate. The organic layer is washed with brine and concentrated under vacuum. Chilling gives the product as crystals (0.10 g).

REFERENCE EXAMPLE 68

5-(2-Pyridinyl)thiophene-2-carbonyl chloride

A mixture of 1.0 g of 5-(2-pyridinyl)thiophene-2-carboxylic acid and 5 ml of thionyl chloride is refluxed for 2.5 hours. The mixture is concentrated to dryness under vacuum. Toluene is added (2 times) and the solvent removed under vacuum to give the product as a glass.

REFERENCE EXAMPLE 69

6-[(Cyclohexylcarbonyl)amino]pyridine-3-carboxylic acid

To a chilled (0° C.) solution of 5.0 g of methyl 6-aminopyridine-3-carboxylate and 12.6 ml of diisopropylethylamine in 50 ml of dichloromethane under argon is added a solution of 9.7 ml of cyclohexylcarbonyl chloride in 10 ml of dichloromethane. The mixture is stirred at room temperature overnight and diluted with 200 ml of dichloromethane and 60 ml of water. The organic layer is separated, washed with 60 ml of brine and dried ($Na_2SO_4$). The solution is filtered through a thin pad of hydrous magnesium silicate and the filtrate concentrated under vacuum to give 12.8 g of a solid.

The above solid (12.0 g) in a mixture of 150 ml of tetrahydrofuran-methanol (1:1) is chilled (0° C.) and 62 ml of 2N sodium hydroxide added. The mixture is stirred at room temperature for 3 hours, neutralized with 10 ml of glacial acetic acid and concentrated under vacuum. The mixture (containing solid) is acidified to pH 1 with 1N HCl and extracted with 250 ml of ethyl acetate and twice with 100 ml of ethyl acetate. The combined extract is washed with 100 ml of brine, dried ($Na_2SO_4$) and concentrated to a white solid. Trituration with hexane gives 6.5 g of product as a white solid.

REFERENCE EXAMPLE 70

Methyl 6-aminopyridine-3-carboxylate

Dry methanol (400 ml) is cooled in an ice bath and HCl gas is bubbled into the mixture for 25 minutes. To the MeOH-HCl is added 30 g of 6-aminopyridine-3-carboxylic acid and then the mixture is stirred and heated at 90° C. for 2 hours (all the solid dissolved). The solvent is removed under vacuum and the residual solid dissolved in 100 ml of water. The acidic solution is neutralized with saturated sodium bicarbonate (solid separated) and the mixture chilled and filtered to give 30 g of white crystals, m.p. 150°–154° C.

REFERENCE EXAMPLE 71

6-[(5-fluoro-2-methylbenzoyl)amino]pyridine-3-carboxylic acid

To a mixture of 4.5 g of methyl 6-aminopyridine-3-carboxylate and 5.53 ml of triethylamine in 40 ml of dichloromethane (cooled in an ice bath) is added 6.38 g of 5-fluoro-2-methylbenzoyl chloride in 10 ml of dichloromethane. The mixture is stirred at room temperature under argon for 18 hours and an additional 3.4 g of 5-fluoro-2-methylbenzoyl chloride added. After stirring at room temperature for 3 hours, the mixture is filtered to give 3.0 g of methyl 6-[[bis(5-fluoro-2-methylbenzoyl)]amino]pyridine-3-carboxylate. The filtrate is concentrated to dryness and the residue triturated with hexane and ethyl acetate to give an additional 9.0 g of bis acylated compound.

A mixture of 12.0 g of methyl 6-[[bis(5-fluoro-2-methylbenzoyl)]amino]pyridine-3-carboxylate, 60 ml of methanol-tetrahydrofuran (1:1) and 23 ml of 5 N NaOH is stirred at room temperature for 16 hours. The mixture is concentrated under vacuum, diluted with 25 ml of water, cooled and acidified with 1N HCl. The mixture is filtered and the solid washed with water to give 6.3 g of the product as a white solid.

As described for Reference Example 71, but substituting the appropriate aroyl chloride, heteroaroyl chloride, cycloalkanoyl chlorides, phenylacetylchlorides and related appropriate acid chlorides, the following 6-[(aroylamino]pyridine-3-carboxylic acids, 6-[(heteroaroyl)amino]pyridine-3-carboxylic acids and related 6-[(acylated)amino]pyridine-3-carboxylic acids are prepared.

REFERENCE EXAMPLE 72

6-[(3-Methyl-2-thienylcarbonyl)amino]pyridine-3-carboxylic acid

REFERENCE EXAMPLE 73

6-[(2-Methyl-3-thienylcarbonyl)amino]pyridine-3-carboxylic acid

REFERENCE EXAMPLE 74

6-[(3-Methyl-2-furanylcarbonyl)amino]pyridine-3-carboxylic acid

REFERENCE EXAMPLE 75

6-[(2-Methyl-3-furanylcarbonyl)amino]pyridine-3-carboxylic acid

REFERENCE EXAMPLE 76

6-[(3-fluoro-2-methylbenzyl)amino]pyridine-3-carboxylic acid

REFERENCE EXAMPLE 77

6-[(2-Methlbenzoyl)amino]pyridine-3-carboxylic acid

REFERENCE EXAMPLE 78

6-[(2-chlorobenzoyl)amino]pyridine-3-carboxylic acid

REFERENCE EXAMPLE 79

6-[(2-Fluorobenzoyl)amino]pyridine-3-carboxylic acid

REFERENCE EXAMPLE 80

6-[(2-Chloro-4-fluorobenzoyl)amino]pyridine-3-carboxylic acid

REFERENCE EXAMPLE 81

6-[(2,4-Dichlorobenzoyl)amino]pyridine-3-carboxylic acid

REFERENCE EXAMPLE 82

6-[(4-Chloro-2-fluorobenzoyl)amino]pyridine-3-carboxylic acid

REFERENCE EXAMPLE 83

6-[(3,4,5-Trimethoxybenzoyl)amino]pyridine-3-carboxylic acid

REFERENCE EXAMPLE 84

6-[(2,4-Difluorobenzoyl)amino]pyridine-3-carboxylic acid

REFERENCE EXAMPLE 85

6-[(2-Bromobenzoyl)amino]pyridine-3-carboxylic acid

REFERENCE EXAMPLE 86

6-[(2-Chloro-4-nitrobenzoyl)amino]pyridine-3-carboxylic acid

REFERENCE EXAMPLE 87

6-[(Tetrahydrofuranyl-2-carbonyl)amino]pyridine-3-carboxylic acid

REFERENCE EXAMPLE 88

6-[(Tetrahydrothienyl-2-carbonyl)amino]pyridine-3-carboxylic acid

REFERENCE EXAMPLE 89

6-[(Cyclohexylcarbonyl)amino]pyridine-3-carboxylic acid

REFERENCE EXAMPLE 90

6-[(cyclohex-3-enecarbonyl)amino]pyridine-3-carboxylic acid

REFERENCE EXAMPLE 91

6-[(5-Fluoro-2-methylbenzeneacetyl)amino]pyridine-3-carboxylic acid

REFERENCE EXAMPLE 92

6-[(2-Chlorobenzeneacetyl)amino]pyridine-3-carboxylic acid

REFERENCE EXAMPLE 93

6-[(cyclopentylcarbonyl)amino]pyridine-3-carboxylic acid

REFERENCE EXAMPLE 94

6-[(cyclohexylacetyl)amino]pyridine-3-carboxylic acid

REFERENCE EXAMPLE 95

6-[(3-Methyl-2-thienylacetyl]amino]pyridine-3-carboxylic acid

REFERENCE EXAMPLE 96

6-[(2-Methyl-3-thienylacetyl)amino]pyridine-3-carboxylic acid

REFERENCE EXAMPLE 97

6-[(3-Methyl-2-furanylacetyl)amino]pyridine-3-carboxylic acid

REFERENCE EXAMPLE 98

6-[(2-Methyl-3-furanylacetyl)amino]pyridine-3-carboxylic acid

REFERENCE EXAMPLE 99

6-[(3-Methyl-2-tetrahydrothienylacetyl)amino]pyridine-3-carboxylic acid

REFERENCE EXAMPLE 100

6-[(2-Methyl-3-tetrahydrothienylacetyl)amino]pyridine-3-carboxylic acid

REFERENCE EXAMPLE 101

6-[(2,5-Dichlorobenzoyl)amino]pyridine-3-carboxylic acid

REFERENCE EXAMPLE 102

6-[(3,5-Dichlorobenzoyl)amino]pyridine-3-carboxylic acid

REFERENCE EXAMPLE 103

6-[(2-Methyl-4-chlorobenzoyl)amino]pyridine-3-carboxylic acid

REFERENCE EXAMPLE 104

6-[(2,3-Dimethylbenzoyl)amino]pyridine-3-carboxylic acid

REFERENCE EXAMPLE 105

6-[(2-Methoxybenzoyl)amino]pyridine-3-carboxylic acid

REFERENCE EXAMPLE 106

6-[(2-Trifluoromethoxybenzoyl)amino]pyridine-3-carboxylic acid

REFERENCE EXAMPLE 107

6-[(4-Chloro-2-methoxybenzoyl)amino]pyridine-3-carboxylic acid

REFERENCE EXAMPLE 108

6-[[2-(Trifluoromethyl)benzoyl]amino]pyridine-3-carboxylic acid

REFERENCE EXAMPLE 109

6-[(2,6-Dichlorobenzoyl)amino]pyridine-3-carboxylic acid

REFERENCE EXAMPLE 110

6-[(2,6,Dimethylbenzoyl)amino]pyridine-3-carboxylic acid

REFERENCE EXAMPLE 111

6-[(2-Methylthiobenzoyl)amino]pyridine-3-carboxylic acid

REFERENCE EXAMPLE 112

6-[(4-Fluoro-2-(trifluoromethyl)benzoyl)amino]pyridine-3-carboxylic acid

REFERENCE EXAMPLE 113

6-[(2,3-Dichlorobenzoylamino]pyridine-3-carboxylic acid

REFERENCE EXAMPLE 114

6-[(4-Fluoro-2-methylbenzoyl)amino]pyridine-3-carboxylic acid

REFERENCE EXAMPLE 115

6-[(2,3,5-Trichlorobenzoyl)amino]pyridine-3-carboxylic acid

REFERENCE EXAMPLE 116

6-[(5-Fluoro-2-chlorobenzoyl)amino]pyridine-3-carboxylic acid

REFERENCE EXAMPLE 117

6-[(2-Fluoro-5-(trifluoromethylbenzoyl)amino]pyridine-3-carboxylic acid

REFERENCE EXAMPLE 118

6-[(5-Fluoro-2-methylbenzoyl)amino]pyridine-3-carbonyl chloride

A mixture of 6.2 g of 6-[(5-fluoro-2-methylbenzoyl)amino]pyridine-3-carboxylic acid and 23 ml of thionyl chloride is refluxed for 1 hour. An additional 12 ml of thionyl chloride is added and the mixture refluxed for 0.5 hour. The mixture is concentrated to dryness under vacuum and 30 ml of toluene added to the residue. The toluene is removed under vacuum and the process (add toluene and remove) is repeated to give 7.7 g of crude product as a solid.

As described for Reference Example 118, the following 6-(acyl)amino)pyridine-3-carbonyl chlorides are prepared.

REFERENCE EXAMPLE 119

6-[(3-Methyl-2-thienylcarbonyl)amino]pyridine-3-carbonyl chloride

REFERENCE EXAMPLE 120

6-[(2-Methyl-3-thienylcarbonyl)amino]pyridine-3-carbonyl chloride

REFERENCE EXAMPLE 121

6-[(3-Methyl-2-furanylcarbonyl)amino]pyridine-3-carbonyl chloride

REFERENCE EXAMPLE 122

6-[(2-Methyl-3-furanylcarbonyl)amino]pyridine-3-carbonyl chloride

REFERENCE EXAMPLE 123

6-[(3-Fluoro-2-methylbenzoyl)amino]pyridine-3-carbonyl chloride

REFERENCE EXAMPLE 124

6-[(2-Methylbenzoyl)amino]pyridine-3-carbonyl chloride

REFERENCE EXAMPLE 125

6-[(2-Chlorobenzoyl)amino]pyridine-3-carbonyl chloride, white crystals

REFERENCE EXAMPLE 126

6-[(2-Fluorobenzoyl)amino]pyridine-3-carbonyl chloride

REFERENCE EXAMPLE 127

6-[(2-Chloro-4-fluorobenzoyl)amino]pyridine-3-carbonyl chloride

REFERENCE EXAMPLE 128

6-[(2,4-Dichlorobenzoyl)amino]pyridine-3-carbonyl chloride

REFERENCE EXAMPLE 129

6-[(4-Chloro-2-fluorobenzoyl)amino]pyridine-3-carbonyl chloride

REFERENCE EXAMPLE 130

6-[(3,4,5-Trimethoxybenzoyl)amino]pyridine-3-carbonyl chloride

REFERENCE EXAMPLE 131

6-[(2,4-Difluorobenzoyl)amino]pyridine-3-carbonyl chloride

REFERENCE EXAMPLE 132

6-[(2-Bromobenzoyl)amino]pyridine-3-carbonyl chloride

REFERENCE EXAMPLE 133

6-[(2-Chloro-4-nitrobenzoyl)amino]pyridine-3-carbonyl chloride

REFERENCE EXAMPLE 134

6-[(Tetrahydrofuranyl-2-carbonyl)amino]pyridine-3-carbonyl chloride

REFERENCE EXAMPLE 135

6-[(Tetrahydrothienyl-2-carbonyl)amino]pyridine-3-carbonyl chloride

REFERENCE EXAMPLE 136

6-[(Cyclohexylcarbonyl)amino]pyridine-3-carbonyl chloride

REFERENCE EXAMPLE 137

6-[(Cyclohex-3-enecarbonyl)amino]pyridine-3-carbonyl chloride

REFERENCE EXAMPLE 138

6-[(2-Methylbenzeneacetyl)amino]pyridine-3-carbonyl chloride

REFERENCE EXAMPLE 139

6-[(2-Chlorobenzeneacetyl)amino]pyridine-3-carbonyl chloride

REFERENCE EXAMPLE 140

6-[(Cyclopentylcarbonyl)amino]pyridine-3-carbonyl chloride

REFERENCE EXAMPLE 141

6-[(Cyclohexylacetyl)amino]pyridine-3-carbonyl chloride

REFERENCE EXAMPLE 142

6-[(3-Methyl-2-thienylacetyl)amino]pyridine-3-carbonyl chloride

REFERENCE EXAMPLE 143

6-[(2-Methyl-3-thienylacetyl)amino]pyridine-3-carbonyl chloride

REFERENCE EXAMPLE 144

6-[(3-Methyl-2-furanylacetyl)amino]pyridine-3-carbonyl chloride

REFERENCE EXAMPLE 145

6-[(2-Methyl-3-furanylacetyl)amino]pyridine-3-carbonyl chloride

REFERENCE EXAMPLE 146

6-[(2-Methyl-5-fluorobenzeneacetyl)amino]pyridine-3-carbonyl chloride

REFERENCE EXAMPLE 147

6-[(3-Methyl-2-tetrahydrothienylacetyl)amino] pyridine-3-carbonyl chloride

REFERENCE EXAMPLE 148

6-[(2-Methyl-3-tetrahydrothienylacetyl)amino] pyridine-3-carbonyl chloride

REFERENCE EXAMPLE 149

6-[(2,5-Dichlorobenzoyl)amino]pyridine-3-carbonyl chloride

REFERENCE EXAMPLE 150

6-[(3,5-Dichlorobenzoyl)amino]pyridine-3-carbonyl chloride

REFERENCE EXAMPLE 151

6-[(2-Methyl-4-chlorobenzoyl)amino]pyridine-3-carbonyl chloride

REFERENCE EXAMPLE 152

6-[(2,3-Dimethylbenzoyl)amino]pyridine-3-carbonyl chloride

REFERENCE EXAMPLE 153

6-[(2-Methoxybenzoyl)amino]pyridine-3-carbonyl chloride

REFERENCE EXAMPLE 154

6-[(2-Trifluoromethyoxybenzoyl)amino]pyridine-3-carbonyl chloride

REFERENCE EXAMPLE 155

6-[(4-Chloro-2-methoxybenzoyl)amino] pyridine-3-carbonyl chloride

REFERENCE EXAMPLE 156

6-[[2-(Trifluoromethyl)benzoyl]amino] pyridine-3-carbonyl chloride

REFERENCE EXAMPLE 157

6-[(2,6-Dichlorobenzoyl)amino]pyridine-3-carbonyl chloride

REFERENCE EXAMPLE 158

6-[(2,6-Dimethylbenzoyl)amino]pyridine-3-carbonyl chloride

REFERENCE EXAMPLE 159

6-[(2-Methylthiobenzoyl)amino]pyridine-3-carbonyl chloride

REFERENCE EXAMPLE 160

6-[(4-Fluoro-2-(trifluoromethyl)benzoyl)amino] pyridine-3-carbonyl chloride

REFERENCE EXAMPLE 161

6-[(2,3-Dichlorobenzoyl)amino]pyridine-3-carbonyl chloride

REFERENCE EXAMPLE 162

6-[(4-Fluoro-2-methylbenzoyl)amino]pyridine-3-carbonyl chloride

REFERENCE EXAMPLE 163

6-[(2,3,5-Trichlorobenzoyl)amino]pyridine-3-carbonyl chloride

REFERENCE EXAMPLE 164

6-[(5-Fluoro-2-chlorobenzoyl)amino]pyridine-3-carbonyl chloride

REFERENCE EXAMPLE 165

6-[(2-Fluoro-5-(trifluoromethyl)benzoyl)amino] pyridine-3-carbonyl chloride

As described for Reference Example 71, the following bis acylated products (Table A) are prepared and purified by silica gel chromatography. These compounds are then hydrolysed to the acids as described in Example 71 (Table B).

TABLE A

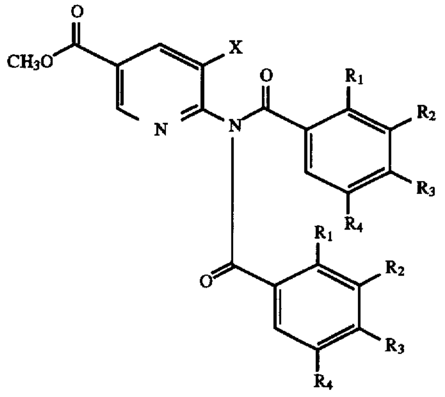

| Ref. Ex No. | $R_1$ | $R_2$ | $R_3$ | $R_4$ | X | $M^+$ |
|---|---|---|---|---|---|---|
| 166 | $CH_3$ | H | H | H | H | 388 |
| 167 | $CH_3$ | H | H | F | H | 424 |
| 168 | $CH_3$ | F | H | H | H | 426 |
| 169 | H | $OCH_3$ | $OCH_3$ | $OCH_3$ | H | 540 |
| 170 | Cl | H | H | H | H | 430 |
| 171 | F | H | F | H | H | 396 |
| 172 | Br | H | H | H | H | 520 |
| 173 | Cl | H | F | H | H | 412 |
| 174 | Ph | H | Ph | H | H | 512 |
| 175 | Cl | H | H | Br | H | 474 |
| 176 | $CH_3$ | H | H | F | Br | |
| 177 | $CH_3$ | H | H | H | Br | 468 |

$M^+$ is molecular ion found from FAB mass spectrum

TABLE B

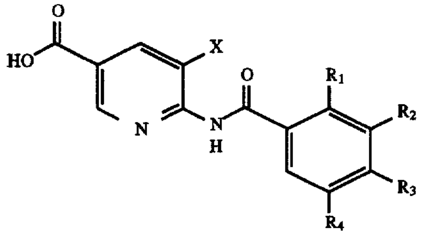

| Ref. Ex No. | $R_1$ | $R_2$ | $R_3$ | $R_4$ | X | $M^+$ |
|---|---|---|---|---|---|---|
| 178 | $CH_3$ | H | H | H | H | 256 |
| 179 | $CH_3$ | H | H | F | H | 274 |
| 180 | $CH_3$ | F | H | H | H | 274 |
| 181 | H | $OCH_3$ | $OCH_3$ | $OCH_3$ | H | 332 |
| 182 | Cl | H | H | H | H | 276 |
| 183 | F | H | F | H | H | 278 |
| 184 | Br | H | H | H | H | 322 |
| 185 | Cl | H | F | H | H | 294 |
| 186 | Ph | H | H | H | H | 318 |
| 187 | Cl | H | H | Br | H | 356 |
| 188 | $CH_3$ | H | H | F | Cl | |
| 189 | $CH_3$ | H | H | H | Br | 336 |

$M^+$ is molecular ion found from FAB mass spectrum.

REFERENCE EXAMPLE 190

6-Amino-5-bromopyridine-3-carboxylic acid

To a stirred solution of 6-aminonicotinic acid (13.8 g, 0.1 mole) in glacial acetic acid (100 ml), bromine (16 g, 5 ml, 0.1 mole) in acetic acid (20 ml) is added slowly. The reaction mixture is stirred for 8 hours at room temperature and the acetic acid is removed under reduced pressure. The yellow solid residue is dissolved in water and carefully neutralized with 30% $NH_4OH$. The separated solid is filtered and washed with water to give 18 g of solid; mass spectrum: 218 ($M^+$).

REFERENCE EXAMPLE 191

Methyl 6-amino-5-bromopyridine-3-carboxylate

6-Amino-5-bromopyridine-3-carboxylic acid (10 g, 50 mmol) is dissolved in saturated methanolic HCl (100 ml) and refluxed for 24 hours. The solvent, methanol, is re-moved under reduced pressure and the residue is dissolved in ice cold water. The aqueous solution is neutralized with 0.1N NaOH and the solid which separates is filtered; washed well with water and air dried to yield 10 g of product as a solid: mass spectrum 231 ($M^+$).

REFERENCE EXAMPLE 192

6-[(2-Methylbenzeneacetyl)amino]pyridine-3-carboxylic acid

To a cooled (0° C.) mixture of 5.0 g methyl 6-aminopyridine-3-carboxylate, 12.6 ml of N,N-diisopropylethylamine in 40 ml of dichloromethane is added a solution of 12.2 g of 2-methylbenzeneacetyl chloride in 10 ml of dichloromethane. The mixture is stirred under argon at room temperature overnight. The mixture is diluted with 200 ml of dichloromethane and 50 ml of water and the organic layer separated. The organic layer is washed with 50 ml each of 1M $NaHCO_3$, brine and dried ($Na_2SO_4$). The solution is filtered through a thin pad of hydrous magnesium silicate and the filtrate concentrated to dryness. The residue (9.0 g) is chromatographed on a silica gel column with hexane-ethyl acetate (3:1) as eluent to give 8.6 g of solid. This solid, mainly methyl 6-[[bis(2-methylbenzeneacetyl)]amino]pyridine-3-carboxylate, is dissolved in 60 ml of tetrahydrofuran-methanol (1:1) and 23 ml of 5N NaOH added to the solution. The mixture is stirred at room temperature overnight and the mixture concentrated under vacuum. Water (25 ml) is added and the mixture is stirred and acidified with cold 1N HCl. The mixture is chilled and the solid filtered and washed with water to give 5.9 g of off-white solid.

REFERENCE EXAMPLE 193

6-[(2-Methylbenzeneacetyl)amino]pyridine-3-carbonyl chloride

A mixture of 4.5 g of 6-[(2-methylbenzeneacetyl)amino]pyridine-3-carboxylic acid and 25 ml of thionyl chloride is refluxed for 1 hour and then concentrated to dryness under vacuum. To the residue is added 20 ml of toluene and the solvent removed under vacuum. The addition and removal of toluene is repeated and the residual solid dried at room temperature under vacuum to give 5.3 g of dark brown solid.

REFERENCE EXAMPLE 194

2-(2-Pyridinyl)benzoic acid

A mixture of methyl 2-iodobenzoate (12 g, 47 mmol), 2-pyridinyl-tri-n-butyl stannous (20 g, 55 mmol) and tetrakis (triphenyl phosphine) palladium (O) (2 g), is refluxed in toluene (degassed) for 48 hours. The reaction mixture is concentrated under vacuum and the residue is chromatographed on a column of silica gel with 50% ethylacetate-:hexane as eluent. The initial fractions (2 lits) are discarded and finally the product methyl 2-(2-pyridinyl)benzoate, is eluted and isolated as an oil. (Yield: 5.5 g): mass spectrum, 213 ($M^+$)

A mixture of the preceding compound (3.0 g, 14 mmol) and NaOH (600 mg, 15 mmol) is refluxed in MeOH:water (9:1) (50 ml) for 4 hours. When the reaction is complete, it is concentrated under vacuum and the residue dissolved in 50 ml of cold water. Neutralization with glacial acetic acid affords a solid which is filtered off and washed with water to give 2.5 g of brown solid; slightly soluble in water; mass spectrum (CI) 200 ($M^+1$).

EXAMPLE 1

N-[4-[(5,6,7,8-Tetrahydro-4H-thieno[3,2-b]azepin-4-yl)carbonyl]phenyl]-3,4-dichlorobenzamide To a solution of 0.30 g of 4-(4-aminobenzoyl)-5,6,7,8-tetrahydro-4H-thieno[3,2-b]azepine and 0.208 ml of triethylamine in 10 ml of dichloromethane is added, under argon, 0.251 g of 3,4-dichlorobenzoyl chloride. The mixture is stirred overnight and concentrated to dryness under vacuum. The residue is dissolved in ethyl acetate and the solution washed with $H_2O$, 2N citric acid, $NaHCO_3$ solution, brine and dried ($Na_2SO_4$). The solvent is removed and the residual yellow solid crystallized from ethyl acetate-hexane to give 0.254 g of crystals, m.p. 154°–160° C.

EXAMPLE 2

N-[4-[(5,6,7,8-Tetrahydro-4H-thieno[3,2-b]azepin-4-yl)carbonyl]phenyl]-2-chlorobenzeneacetamide A solution of 0.307 g of 2-chlorophenylacetic acid in 3 ml of thionyl chloride is stirred 2 hours at room temperature. The excess thionyl chloride is removed under vacuum and 5 ml of toluene added and removed (under vacuum) three times. The residue is dissolved in 5 ml of dichloromethane and 0.3 ml of triethylamine. To the solution is added (under argon) 0.49 g of 4-(4-aminobenzoyl)-5,6,7,8-tetrahydro-4H-thieno[3,2-b]azepine and the mixture stirred overnight. The volatiles are removed under vacuum and the residue dissolved in ethyl acetate. The solution is washed with 1N HCl, $Na_2CO_3$ solution, brine and dried ($Na_2SO_4$). The solvent is removed and the residual solid is crystallized from ethyl acetate-hexane to give 0.36 g of tan crystals, m.p. 178°–180° C.

EXAMPLE 3

N-[4-[(5,6,7,8-Tetrahydro-4H-thieno[3,2-b]azepin-4-yl)carbonyl]phenyl]-2-methylbenzamide As described for Example 1, 4-(4-aminobenzoyl)-5,6,7,8-tetrahydro-4H-thieno[3,2-b]azepine (0.001 ml) is reacted with 2-methylbenzoyl chloride in dichloromethane to give the product. Crystallization from ethyl acetate-hexane gives crystals, m.p. 181°–182° C.

The following compounds are prepared as described in Example 1.

| Ex. No. | |
|---|---|
| 4 | N-[4-[(5,6,7,8-Tetrahydro-4H-thieno[3,2-b]azepin-4-yl)carbonyl]phenyl] 2-furanecarboxamide, beige solid. |
| 5 | N-[4-[(5,6,7,8-Tetrahydro-4H-thieno[3,2-b]azepin-4-yl)carbonyl]phenyl] 4-tert-butylbenzamide, m.p. 182–184° C. |
| 6 | N-[4-[(5,6,7,8-Tetrahydro-4H-thieno[3,2-b]azepin-4-yl)carbonyl]phenyl]-4-(n-butyl)benzamide, m.p. 152–154° C. |
| 7 | N-[4-[(5,6,7,8-Tetrahydro-4H-thieno[3,2-b]azepin-4-yl)carbonyl]phenyl]-3-methyl-2-thiophenecarboxamide, m.p. 185–187° C. |
| 8 | N-[4-[(5,6,7,8-Tetrahydro-4H-thieno[3,2-b]azepin-4-yl)carbonyl]phenyl]-2,5-dimethylbenzamide, m.p. 170–172° C. |
| 9 | N-[4-[(5,6,7,8-Tetrahydro-4H-thieno[3,2-b]azepin-4-yl)carbonyl]phenyl]-2,5-dichlorobenzamide, m.p. 166–168° C. |
| 10 | N-[4-[(5,6,7,8-Tetrahydro-4H-thieno[3,2-b]azepin-4-yl)carbonyl]phenyl]-2,3-dimethylbenzamide, m.p. 216–220° C. |
| 11 | N-[4-[(5,6,7,8-Tetrahydro-4H-thieno[3,2-b]azepin-4-yl)carbonyl]phenyl]-2,4-dimethylbenzamide, m.p. 202–204° C. |
| 12 | N-[4-[(5,6,7,8-tetrahydro-4H-thieno[3,2-b]azepin-4-yl)carbonyl]phenyl] benzeneacetamide, m.p. 148–150° C. |
| 13 | N-[4-[(5,6,7,8-Tetrahydro-4H-thieno[3,2-b]azepin-4-yl)carbonyl]phenyl]-2-methylbenzeneacetamide, m.p. 60–63° C. (white foam) |
| 14 | N-[4-[(5,6,7,8-Tetrahydro-4H-thieno[3,2-b]azepin-4-yl)carbonyl]phenyl]-2,4-dichlorobenzamide, m.p. 198–200° C. |
| 15 | N-[4-[(5,6,7,8-Tetrahydro-4H-thieno[3,2-b]azepin-4-yl)carbonyl]phenyl]-3-cyclohexenecarboxamide, m.p. 194–196° C. |
| 16 | N-[4-[(5,6,7,8-Tetrahydro-4H-thieno[3,2-b]azepin-4-yl)carbonyl]phenyl]-2-chlorobenzamide |
| 17 | N-[4-[(5,6,7,8-Tetrahydro-4H-thieno[3,2-b]azepin-4-yl)carbonyl]phenyl]-2,5-dichlorobenzamide |
| 18 | N-[4-[(5,6,7,8-Tetrahydro-4H-thieno[3,2-b]azepin-4-yl)carbonyl]phenyl]-3,5-dichlorobenzamide |
| 19 | N-[4-[(5,6,7,8-Tetrahydro-4H-thieno[3,2-b]azepin-4-yl)carbonyl]phenyl]-2-fluorobenzamide |
| 20 | N-[4-[(5,6,7,8-Tetrahydro-4H-thieno[3,2-b]azepin-4-yl)carbonyl]phenyl]-3-fluorobenzamide |
| 21 | N-[4-[(5,6,7,8-Tetrahydro-4H-thieno[3,2-b]azepin-4-yl)carbonyl]phenyl]-2-chloro-4-methylbenzamide |
| 22 | N-[4-[(5,6,7,8-Tetrahydro-4H-thieno[3,2-b]azepin-4-yl)carbonyl]phenyl]-2-methyl-4-chlorobenzamide |
| 23 | N-[4-[(5,6,7,8-Tetrahydro-4H-thieno[3,2-b]azepin-4-yl)carbonyl]phenyl]-2-methoxybenzamide |
| 24 | N-[4-[(5,6,7,8-Tetrahydro-4H-thieno[3,2-b]azepin-4-yl)carbonyl]phenyl]-2-(trifluoromethoxy)benzamide |
| 25 | N-[4-[(5,6,7,8-Tetrahydro-4H-thieno[3,2-b]azepin-4-yl)carbonyl]phenyl]-2,4-dimethoxybenzamide |
| 26 | N-[4-[(5,6,7,8-Tetrahydro-4H-thieno[3,2-b]azepin-4-yl)carbonyl]phenyl]-2-methoxy-4-chlorobenzamide |
| 27 | N-[4-[(5,6,7,8-Tetrahydro-4H-thieno[3,2-b]azepin-4-yl)carbonyl]phenyl]-2,6-dimethoxybenzamide |

-continued

| Ex. No. | |
|---|---|
| 28 | N-[4-[(5,6,7,8-Tetrahydro-4H-thieno [3,2-b]azepin-4-yl)carbonyl]phenyl] -2-(trifluoromethyl)benzamide |
| 29 | N-[4-[(5,6,7,8-Tetrahydro-4H-thieno [3,2-b]azepin-4-yl)carbonyl]phenyl] -2,6-dimethylbenzamide |
| 30 | N-[4-[(5,6,7,8-Tetrahydro-4H-thieno [3,2-b]azepin-4-yl)carbonyl]phenyl] -2-(methylthio)benzamide |
| 31 | N-[4-[(5,6,7,8-Tetrahydro-4H-thieno [3,2-b]azepin-4-yl)carbonyl]phenyl] -3-(trifluoromethyl)benzamide |
| 32 | N-[4-[(5,6,7,8-Tetrahydro-4H-thieno [3,2-b]azepin-4-yl)carbonyl]phenyl] -4-fluoro-2-(trifluoromethyl) benzamide |
| 33 | N-[4-[(5,6,7,8-Tetrahydro-4H-thieno [3,2-b]azepin-4-yl)carbonyl]phenyl] -2,3-dichlorobenzamide |
| 34 | N-[4-[(5,6,7,8-Tetrahydro-4H-thieno [3,2-b]azepin-4-yl)carbonyl]phenyl] -4-fluoro-3-(trifluoromethyl) benzamide |
| 35 | N-[4-[(5,6,7,8-Tetrahydro-4H-thieno [3,2-b)azepin-4-yl)carbonyl]phenyl] -2-fluoro-3-(trifluoromethyl) benzamide |
| 36 | N-[4-[(5,6,7,8-Tetrahydro-4H-thieno [3,2-b)azepin-4-yl)carbonyl]phenyl] -3,5-dimethylbenzamide |
| 37 | N-[4-[(5,6,7,8-Tetrahydro-4H-thieno [3,2-b]azepin-4-yl)carbonyl]phenyl] -2,5-dimethylbenzamide |
| 38 | N-[4-[(5,6,7,8-Tetrahydro-4H-thieno [3,2-b]azepin-4-yl)carbonyl]phenyl] -3,4-dimethylbenzamide |
| 39 | N-[4-[(5,6,7,8-Tetrahydro-4H-thieno [3,2-b]azepin-4-yl)carbonyl]phenyl] -2,4,6-trichlorobenzamide |
| 40 | N-[4-[(5,6,7,8-Tetrahydro-4H-thieno [3,2-b]azepin-4-yl)carbonyl]phenyl] -2,4-difluorobenzamide |
| 41 | N-[4-[(5,6,7,8-Tetrahydro-4H-thieno [3,2-b]azepin-4-yl)carbonyl]phenyl] -2,5-difluorobenzamide |
| 42 | N-[4-[(5,6,7,8-Tetrahydro-4H-thieno [3,2-b]azepin-4-yl)carbonyl]phenyl] -3,5-difluorobenzamide |
| 43 | N-[4-[(5,6,7,8-Tetrahydro-4H-thieno [3,2-b]azepin-4-yl)carbonyl]phenyl] -3-fluoro-2-methylbenzamide |
| 44 | N-[4-[(5,6,7,8-Tetrahydro-4H-thieno [3,2-b]azepin-4-yl)carbonyl]phenyl] -2,3-dichlorobenzamide |
| 45 | N-[4-[(5,6,7,8-Tetrahydro-4H-thieno [3,2-b]azepin-4-yl)carbonyl]phenyl] -2,3-difluorobenzamide |
| 46 | N-[4-[(5,6,7,8-Tetrahydro-4H-thieno [3,2-b]azepin-4-yl)carbonyl]phenyl] -4-fluoro-2-methylbenzamide |
| 47 | N-[4-[(5,6,7,8-Tetrahydro-4H-thieno [3,2-b]azepin-4-yl)carbonyl]phenyl] -5-fluoro-2-methylbenzamide |
| 48 | N-[4-[(5,6,7,8-Tetrahydro-4H-thieno [3,2-b]azepin-4-yl)carbonyl]phenyl] -2,3,5-trichlorobenzamide |
| 49 | N-[4-[(5,6,7,8-Tetrahydro-4H-thieno [3,2-b]azepin-4-yl)carbonyl]phenyl] -2-fluoro-4-(trifluoromethyl) benzamide |
| 50 | N-[4-[(5,6,7,8-Tetrahydro-4H-thieno [3,2-b]azepin-4-yl)carbonyl]phenyl] -2-fluoro-5-(trifluoromethyl) benzamide |
| 51 | N-[4-[(5,6,7,8-Tetrahydro-4H-thieno [3,2-b]azepin-4-yl)carbonyl]phenyl] -2-fluoro-6-(trifluoromethyl) benzamide |

-continued

| Ex. No. | |
|---|---|
| 52 | N-[4-[(5,6,7,8-Tetrahydro-4H-thieno [3,2-b]azepin-4-yl)carbonyl]phenyl] -3-fluoro-5-(trifluoromethyl) benzamide |
| 53 | N-[4-[(5,6,7,8-Tetrahydro-4H-thieno [3,2-b]azepin-4-yl)carbonyl]-2-chlorophenyl]-2-methyl-3-fluoro-benzamide |
| 54 | N-[4-[(5,6,7,8-Tetrahydro-4H-thieno [3,2-b]azepin-4-yl)carbonyl]-2-chlorophenyl]-2-methyl-5-fluoro-benzamide |
| 55 | N-[4-[(5,6,7,8-Tetrahydro-4H-thieno [3,2-b]azepin-4-yl)carbonyl]-2-chlorophenyl]-2-methylbenzamide |
| 56 | N-[4-[(5,6,7,8-Tetrahydro-4H-thieno [3,2-b]azepin-4-yl)carbonyl]-2-chlorophenyl]benzamide |
| 57 | N-[4-[(5,6,7,8-Tetrahydro-4H-thieno [3,2-b]azepin-4-yl)carbonyl]-2-methoxyphenyl]-2,4-dichloro-benzamide |
| 58 | N-[4-[(5,6,7,8-Tetrahydro-4H-thieno [3,2-b]azepin-4-yl)carbonyl]-2-methoxyphenyl]-3-fluoro-2-methyl-benzamide |
| 59 | N-[4-[(5,6,7,8-Tetrahydro-4H-thieno [3,2-b]azepin-4-yl)carbonyl]-2-methylphenyl]-3-fluoro-2-methyl-benzamide |
| 60 | N-[4-[(5,6,7,8-Tetrahydro-4H-thieno [3,2-b]azepin-4-yl)carbonyl]-2-methoxyphenyl]-2 -methylbenzamide |
| 61 | N-[4-[(5,6,7,8-Tetrahydro-4H-thieno [3,2-b]azepin-4-yl)carbonyl]-2-methoxyphenyl]-2,3-dimethylbenz-amide |
| 62 | N-[4-[(5,6,7,8-Tetrahydro-4H-thieno [3,2-b]azepin-4-yl)carbonyl]-2-methylphenyl]-2,4-dichlorobenz-amide |
| 63 | N-[4-[(5,6,7,8-Tetrahydro-4H-thieno [3,2-b]azepin-4-yl)carbonyl]-2-methylphenyl]-5-fluoro-2-methyl-benzamide |
| 64 | N-[4-[(5,6,7,8-Tetrahydro-4H-thieno [3,2-b]azepin-4-yl)carbonyl]phenyl] -2-methylphenyl]-2-(trifluoro-methyl)benzamide |
| 65 | N-[4-[(5,6,7,8-Tetrahydro-4H-thieno [3,2-b]azepin-4-yl)carbonyl]phenyl] -2-methylphenyl]-3-(trifluoro-methyl)benzamide |
| 66 | N-[4-[(5,6,7,8-Tetrahydro-4H-thieno [3,2-b]azepin-4-yl)carbonyl]-3-chlorophenyl]-2-methylbenzamide |
| 67 | N-[4-[(5,6,7,8-Tetrahydro-4H-thieno [3,2-b]azepin-4-yl)carbonyl]-3-chlorophenyl]-2-chlorobenzamide |
| 68 | N-[4-[(5,6,7,8-Tetrahydro-4H-thieno [3,2-b]azepin-4-yl)carbonyl]-3-chlorophenyl]-2,4-dichlorobenzamide m.p. 256–260° C. |
| 69 | N-[4-[(5,6,7,8-Tetrahydro-4H-thieno [3,2-b]azepin-4-yl)carbonyl]-3-chlorophenyl]-2,3-dimethylbenzamide |
| 70 | N-[4-[(5,6,7,8-Tetrahydro-4H-thieno [3,2-b]azepin-4-yl)carbonyl]-3-chlorophenyl]-5-fluoro-2-methyl-benzamide, m.p. 188–191° C. |
| 71 | N-[4-[(5,6,7,8-Tetrahydro-4H-thieno [3,2-b]azepin-4-yl)carbonyl]-3-chlorophenyl]-2,3,5-trichloro-benzamide |
| 72 | N-[4-[(5,6,7,8-Tetrahydro-4H-thieno [3,2-b]azepin-4-yl)carbonyl]-3-chlorophenyl]-2-methoxybenzamide |
| 73 | N-[4-[(5,6,7,8-Tetrahydro-4H-thieno |

-continued

| Ex. No. | |
|---|---|
| | [3,2-b]azepin-4-yl)carbonyl]-3-chlorophenyl]-3,5-dichlorobenzamide |
| 74 | N-[4-[(5,6,7,8-Tetrahydro-4H-thieno[3,2-b]azepin-4-yl)carbonyl]-3-chlorophenyl]-2-(trifluoromethyl)-benzamide |
| 75 | N-[4-[(5,6,7,8-Tetrahydro-4H-thieno[3,2-b]azepin-4-yl)carbonyl]-3-chlorophenyl]-2-methylbenzamide |
| 76 | N-[4-[(5,6,7,8-Tetrahydro-4H-thieno[3,2-b]azepin-4-yl)carbonyl]-3-chlorophenyl]-2-methyl-3-thiophenecarboxamide |
| 77 | N-[4-[(5,6,7,8-Tetrahydro-4H-thieno[3,2-b]azepin-4-yl)carbonyl]-3-chlorophenyl]-2-methyl-3-furanecarboxamide |
| 78 | N-[4-[(5,6,7,8-Tetrahydro-4H-thieno[3,2-b]azepin-4-yl)carbonyl]-3,5-dichlorophenyl]-3-fluoro-2-methyl-benzamide |
| 79 | N-[4-[(5,6,7,8-Tetrahydro-4H-thieno[3,2-b]azepin-4-yl)carbonyl]-3,5-dichlorophenyl]-2,3-dimethyl-benzamide |
| 80 | N-[4-[(5,6,7,8-Tetrahydro-4H-thieno[3,2-b]azepin-4-yl)carbonyl]-3,5-dichlorophenyl]-5-fluoro-2-methyl-benzamide |
| 81 | N-[4-[(5,6,7,8-Tetrahydro-4H-thieno[3,2-b]azepin-4-yl)carbonyl]-3-chlorophenyl]-2,6-dichloro-benzamide |
| 82 | N-[4-[(5,6,7,8-Tetrahydro-4H-thieno[3,2-b]azepin-4-yl)carbonyl]-3-chlorophenyl]-2-chlorobenzene-acetamide |
| 83 | N-[4-[(5,6,7,8-Tetrahydro-4H-thieno[3,2-b]azepin-4-yl)carbonyl]-3-chlorophenyl]-2-(methylthio)-benzamide |
| 84 | N-[4-[(5,6,7,8-Tetrahydro-4H-thieno[3,2-b]azepin-4-yl)carbonyl]-3-chlorophenyl]-2-(trifluoromethoxy)-benzamide |
| 85 | N-[4-[(5,6,7,8-Tetrahydro-4H-thieno[3,2-b]azepin-4-yl)carbonyl]-3-chlorophenyl]-2-fluoro-3-(tri-fluoromethyl)benzamide |
| 86 | N-[4-[(5,6,7,8-Tetrahydro-4H-thieno[3,2-b]azepin-4-yl)carbonyl]-3-chlorophenyl]-4-fluoro-2-(tri-fluoromethyl)benzamide |
| 87 | N-[4-[(5,6,7,8-Tetrahydro-4H-thieno[3,2-b]azepin-4-yl)carbonyl]-3-chlorophenyl]-2,5-dimethylbenz-amide |
| 88 | N-[4-[(5,6,7,8-Tetrahydro-4H-thieno[3,2-b]azepin-4-yl)carbonyl]-3-chlorophenyl]-3,5-dimethylbenz-amide |
| 89 | N-[4-[(5,6,7,8-Tetrahydro-4H-thieno[3,2-b]azepin-4-yl)carbonyl]-3-chlorophenyl]-2,3-dichlorobenz-amide |
| | N-[4-[(5,6,7,8-Tetrahydro-4H-thieno[3,2-b]azepin-4-yl)carbonyl]-3-chloro-2,3,5-trichlorobenzamide |
| 90 | N-[4-[(5,6,7,8-Tetrahydro-4H-thieno[3,2-b]azepin-4-yl)carbonyl]-3-chlorophenyl]-2-fluoro-5-(tri-fluromethyl)benzamide |
| 91 | N-[4-[(5,6,7,8,-Tetrahydro-4H-thieno[3,2-b]azepin-4-yl)carbonyl]-3-chlorophenyl]-2-fluoro-6-(tri-fluoromethyl)benzamide |
| 92 | N-[4-[(5,6,7,8,-Tetrahydro-4H-thieno[3,2-b]azepin-4-yl)carbonyl]-3-chlorophenyl]-3-fluoro-5-(tri-fluoromethyl)benzamide |

EXAMPLE 93

2,4-Dichloro-N-[4-[(2-chloro-5,6,7,8-tetrahydro-4H-thieno[3,2-b]azepin-4-yl)carbonyl]phenyl]benzamide To a cooled (ice bath) solution of 0.245 g 15 (0.8 mmol) of 2-chloro-4-(4-aminobenzoyl)-5,6,7,8-tetrahydro-4H-thieno[3,2-b]azepine and 167 μl (1.2 mmol) of triethylamine in 5 ml of dichloromethane is added 140 μl (1 mmol) of 2,4-dichlorobenzoyl chloride. The solution is stirred under argon at room temperature overnight and diluted with 60 ml of dichloromethane. The mixture is washed with 20 ml each of 2N-citric acid, $H_2O$, 1M $NaHCO_3$, brine and dried ($Na_2SO_4$). The solvent is removed and the residue crystallized from ethyl acetate-hexane to give 0.315 g of white crystals, m.p. 187°–189° C.

The following compounds are prepared as described in Example 93.

| Ex. No. | |
|---|---|
| 94 | N-[4-[(2-Chloro-5,6,7,8-tetrahydro-4H-thieno[3,2-b]azepin-4-yl)carbonyl]phenyl]-3-fluoro-2-methyl-benzamide, m.p. 186–188° C. |
| 95 | N-[4-[(2-Chloro-5,6,7,8-tetrahydro-4H-thieno[3,2-b]azepin-4-yl)carbonyl]phenyl]-2,6-dichlorobenzamide m.p. 245–248° C. |
| 96 | N-[4-[(2-Chloro-5,6,7,8-tetrahydro-4H-thieno[3,2-b]azepin-4-yl)carbonyl]phenyl]-2-methylbenzamide m.p. 169–170° C. |
| 97 | N-[4-[(2-Chloro-5,6,7,8-tetrahydro-4H-thieno[3,2-b]azepin-4-yl)carbonyl]phenyl]-2,5-dichlorobenzamide |
| 98 | N-[4-[(2-Chloro-5,6,7,8-tetrahydro-4H-thieno[3,2-b]azepin-4-yl)carbonyl]phenyl]-3,5-dichlorobenzamide |
| 99 | N-[4-[(2-Chloro-5,6,7,8-tetrahydro-4H-thieno[3,2-b]azepin-4-yl)carbonyl]phenyl]-2-chlorobenzeneacet-amide |
| 100 | N-[4-[(2-Chloro-5,6,7,8-tetrahydro-4H-thieno[3,2-b]azepin-4-yl)carbonyl]phenyl]-3-fluorobenzamide |
| 101 | N-[4-[(2-Chloro-5,6,7,8-tetrahydro-4H-thieno[3,2-b]azepin-4-yl)carbonyl]phenyl]-2-chloro-4-methyl-benzamide |
| 102 | N-[4-[(2-Chloro-5,6,7,8-tetrahydro-4H-thieno[3,2-b]azepin-4-yl)carbonyl]phenyl]-2-methyl-4-chloro-benzamide |
| 103 | N-[4-[(2-Chloro-5,6,7,8-tetrahydro-4H-thieno[3,2-b]azepin-4-yl)carbonyl]phenyl]-2,4-dimethylbenzamide |
| 104 | N-[4-[(2-Chloro-5,6,7,8-tetrahydro-4H-thieno[3,2-b]azepin-4-yl)carbonyl]phenyl]-2,3-dimethylbenzamide |
| 105 | N-[4-[(2-Chloro-5,6,7,8-tetrahydro-4H-thieno[3,2-b]azepin-4-yl)carbonyl]phenyl]-2-methoxybenzamide |
| 106 | N-[4-[(2-Chloro-5,6,7,8-tetrahydro-4H-thieno[3,2-b]azepin-4-yl)carbonyl]phenyl]-2-(trifluoromethoxy)- |

-continued

| Ex. No. | |
|---|---|
| | benzamide |
| 107 | N-[4-[(2-Chloro-5,6,7,8-tetrahydro-4H-thieno[3,2-b]azepin-4-yl)carbonyl]phenyl]-2,4-dimethoxybenzamide |
| 108 | N-[4-[(2-Chloro-5,6,7,8-tetrahydro-4H-thieno[3,2-b]azepin-4-yl)carbonyl)phenyl]-2,6-dimethoxybenzamide |
| 109 | N-[4-[(2-Chloro-5,6,7,8-tetrahydro-4H-thieno[3,2-b]azepin-4-yl)carbonyl)phenyl]-2-methoxy-4-chlorobenzamide |
| 110 | N-[4-[(2-Chloro-5,6,7,8-tetrahydro-4H-thieno[3,2-b]azepin-4-yl)carbonyl]phenyl]-2-(trifluoromethyl) benzamide |
| 111 | N-[4-[(2-Chloro-5,6,7,8-tetrahydro-4H-thieno[3,2-b]azepin-4-yl)carbonyl]phenyl]-3-(trifluoromethyl) benzamide |
| 112 | N-[4-[(2-Chloro-5,6,7,8-tetrahydro-4H-thieno[3,2-b]azepin-4-yl)carbonyl]phenyl]-2,6-dichlorobenzamide |
| 113 | N-[4-[(2-Chloro-5,6,7,8-tetrahydro-4H-thieno[3,2-b]azepin-4-yl)carbonyl]phenyl]-2,6-dimethylbenzamide |
| 114 | N-[4-[(2-Chloro-5,6,7,8-tetrahydro-4H-thieno[3,2-b]azepin-4-yl)carbonyl]phenyl]-2-(methylthio)benzamide |
| 115 | N-[4-[(2-Chloro-5,6,7,8-tetrahydro-4H-thieno[3,2-b]azepin-4-yl)carbonyl]phenyl]-2-methyl-3-thiophenecarboxamide |
| 116 | N-[4-[(2-Chloro-5,6,7,8-tetrahydro-4H-thieno[3,2-b]azepin-4-yl)carbonyl]phenyl]-3-methyl-2-thiophenecarboxamide |
| 117 | N-[4-[(2-Chloro-5,6,7,8-tetrahydro-4H-thieno[3,2-b]azepin-4-yl)carbonyl]phenyl]-2-methyl-3-furanecarboxamide |
| 118 | N-[4-[(2-Chloro-5,6,7,8-tetrahydro-4H-thieno[3,2-b]azepin-4-yl)carbonyl]phenyl]-3-methyl-2-furanecarboxamide |
| 119 | N-[4-[(2-Chloro-5,6,7,8-tetrahydro-4H-thieno[3,2-b]azepin-4-yl)carbonyl]phenyl]-2-chlorobenzeneacetamide |
| 120 | N-[4-[(2-Chloro-5,6,7,8-tetrahydro-4H-thieno[3,2-b]azepin-4-yl)carbonyl]phenyl]-2-methylbenzeneacetamide |
| 121 | N-[4-[(2-Chloro-5,6,7,8-tetrahydro-4H-thieno[3,2-b]azepin-4-yl)carbonyl]phenyl]-2-methyl-3-thiopheneacetamide |
| 122 | N-[4-[(2-Chloro-5,6,7,8-tetrahydro-4H-thieno[3,2-b]azepin-4-yl)carbonyl]phenyl]-4-fluoro-2-(trifluoromethyl)benzamide |
| 123 | N-[4-[(2-Chloro-5,6,7,8-tetrahydro-4H-thieno[3,2-b]azepin-4-yl)carbonyl]phenyl]-4-fluoro-3-(trifluoromethyl)benzamide |
| 124 | N-[4-[(2-Chloro-5,6,7,8-tetrahydro-4H-thieno[3,2-b]azepin-4-yl)carbonyl]phenyl]-2-fluoro-3-(trifluoromethyl)benzamide |
| 125 | N-[4-[(2-Chloro-5,6,7,8-tetrahydro-4H-thieno[3,2-b]azepin-4-yl)carbonyl]phenyl]-3,5-dimethylbenzamide |
| 126 | N-[4-[(2-Chloro-5,6,7,8-tetrahydro-4H-thieno[3,2-b]azepin-4-yl)carbonyl]phenyl]-2,5-dimethylbenzamide |
| 127 | N-[4-[(2-Chloro-5,6,7,8-tetrahydro- |

-continued

| Ex. No. | |
|---|---|
| | 4H-thieno[3,2-b]azepin-4-yl)carbonyl]phenyl]-3.4-dimethylbenzamide |
| 128 | N-[4-[(2-Chloro-5,6,7,8-tetrahydro-4H-thieno[3,2-b]azepin-4-yl)carbonyl]phenyl]-2,4,6-trichlorobenzamide |
| 129 | N-[4-[(2-Chloro-5,6,7,8-tetrahydro-4H-thieno[3,2-b]azepin-4-yl)carbonyl]phenyl]-2,4-difluorobenzamide |
| 130 | N-[4-[(2-Chloro-5,6,7,8-tetrahydro-4H-thieno[3,2-b]azepin-4-yl)carbonyl]phenyl]-2,5-difluorobenzamide |
| 131 | N-[4-[(2-Chloro-5,6,7,8-tetrahydro-4H-thieno[3,2-b]azepin-4-yl)carbonyl]phenyl]-3,5-difluorobenzamide |
| 132 | N-[4-[(2-Chloro-5,6,7,8-tetrahydro-4H-thieno[3,2-b]azepin-4-yl)carbonyl]phenyl]-3-fluoro-2-methylbenzamide |
| 133 | N-[4-[(2-Chloro-5,6,7,8-tetrahydro-4H-thieno[3,2-b]azepin-4-yl)carbonyl]phenyl]-2,3-dichlorobenzamide |
| 134 | N-[4-[(2-Chloro-5,6,7,8-tetrahydro-4H-thieno[3,2-b]azepin-4-yl)carbonyl]phenyl]-2,3-difluorobenzamide |
| 135 | N-[4-[(2-Chloro-5,6,7,8-tetrahydro-4H-thieno[3,2-b]azepin-4-yl)carbonyl]phenyl]-4-fluoro-2-methylbenzamide |
| 136 | N-[4-[(2-Chloro-5,6,7,8-tetrahydro-4H-thieno[3,2-b]azepin-4-yl)carbonyl]phenyl]-5-fluoro-2-methylbenzamide |
| 137 | N-[4-[(2-Chloro-5,6,7,8-tetrahydro-4H-thieno[3,2-b]azepin-4-yl)carbonyl]phenyl]-2,3,5-trichlorobenzamide |
| 138 | N-[4-[(2-Chloro-5,6,7,8-tetrahydro-4H-thieno[3,2-b]azepin-4-yl)carbonyl]phenyl]-2-fluoro-4-(trifluoromethyl)benzamide |
| 139 | N-[4-[(2-Chloro-5,6,7,8-tetrahydro-4H-thieno[3,2-b]azepin-4-yl)carbonyl]phenyl]-2-fluoro-5-(trifluoromethyl)benzamide |
| 140 | N-[4-[(2-Chloro-5,6,7,8-tetrahydro-4H-thieno[3,2-b]azepin-4-yl)carbonyl]phenyl]-2-fluoro-6-(trifluoromethyl)benzamide |
| 141 | N-[4-[(2-Chloro-5,6,7,8-tetrahydro-4H-thieno[3,2-b]azepin-4-yl)carbonyl]phenyl]-3-fluoro-5-(trifluoromethyl)benzamide |
| 142 | N-[4-[(2-Chloro-5,6,7,8-tetrahydro-4H-thieno[3,2-b]azepin-4-yl)carbonyl]-3-chlorophenyl]-3-fluoro-2-methylbenzamide |
| 143 | N-[4-[(2-Chloro-5,6,7,8-tetrahydro-4H-thieno[3,2-b]azepin-4-yl)carbonyl]-3-chlorophenyl]-2,3-dichlorobenzamide |
| 144 | N-[4-[(2-Chloro-5,6,7,8-tetrahydro-4H-thieno[3,2-b]azepin-4-yl)carbonyl]-3-chlorophenyl]-2,4-dichlorobenzamide |
| 145 | N-[4-[(2-Chloro-5,6,7,8-tetrahydro-4H-thieno[3,2-b]azepin-4-yl)carbonyl]-3-chlorophenyl]-2-dimethylbenzamide |
| 146 | N-[4-[(2-Chloro-5,6,7,8-tetrahydro-4H-thieno[3,2-b]azepin-4-yl)carbonyl]-3-chlorophenyl]-4-fluoro-2-methylbenzamide |
| 147 | N-[4-[(2-Chloro-5,6,7,8-tetrahydro-4H-thieno[3,2-b]azepin-4-yl)carbonyl]-3-chlorophenyl]-5-fluoro-2-methylbenzamide |
| 148 | N-[4-[(2-Chloro-5,6,7,8-tetrahydro- |

-continued

| Ex. No. | |
|---|---|
| | 4H-thieno[3,2-b]azepin-4-yl)carbonyl]-3-chlorophenyl]-2,3-dimethylbenzamide |
| 149 | N-[4-[(2-Chloro-5,6,7,8-tetrahydro-4H-thieno[3,2-b]azepin-4-yl)carbonyl]-3-chlorophenyl]-2-methyl-3-chlorobenzamide |
| 150 | N-[4-[(2-Chloro-5,6,7,8-tetrahydro-4H-thieno[3,2-b]azepin-4-yl)carbonyl]-3-chlorophenyl]-2-fluoro-4-(trifluoromethyl)benzamide |
| 151 | N-[4-[(2-Chloro-5,6,7,8-tetrahydro-4H-thieno[3,2-b]azepin-4-yl)carbonyl]-3-chlorophenyl]-2-(trifluoromethyl)benzamide |
| 152 | N-[4-[(2-Chloro-5,6,7,8-tetrahydro-4H-thieno[3,2-b]azepin-4-yl)carbonyl]-3-chlorophenyl]-2-(methylthio)benzamide |
| 153 | N-[4-[(2-Chloro-5,6,7,8-tetrahydro-4H-thieno[3,2-b]azepin-4-yl)carbonyl]-3-methoxyphenyl]-5-fluoro-2-methylbenzamide |
| 154 | N-[4-[(2-Chloro-5,6,7,8-tetrahydro-4H-thieno[3,2-b]azepin-4-yl)carbonyl]-3-methoxyphenyl]-3-fluoro-2-methylbenzamide |

EXAMPLE 155

N-[4-[(5,6,7,8-Tetrahydro-8-oxo-4H-thieno[3,2-b]azepine-4-yl)carbonyl]phenyl]-3-fluoro-2-methylbenzamide To a mixture of 287 mg of 4,5,6,7-tetrahydro-4-(4-aminobenzoyl)-8H-thieno[3,2b-]azepin-8-one in 3 ml of methylene chloride is added 209 μl of triethylamine which is cooled to 0° C. is added 207.1 mg of 2-methyl-3-fluorobenzoyl chloride. The cooling bath is removed and he reaction mixture stirred at room temperature under argon for 18 hours. An additional 50 ml of methylene chloride and 20 ml of water is added and the separated organic layer washed with 2N citric acid, 1M $NaHCO_3$ and brine. The organic layer is dried with $Na_2SO_4$ and passed through a short pad of hydrous magnesium silicate and the filtrate evaporated in vacuo to a white foam which is crystallized from ethyl acetate-hexane to give 305 mg of the desired product as a white solid, m.p. 200°–202° C.

The following compounds are prepared as described in Example 155.

| Example NO. | |
|---|---|
| 156 | N-[4-[(5,6,7,8-Tetrahydro-8-oxo-4H-thieno[3,2-b]azepin-4-yl)carbonyl]-phenyl]-2,4-dichlorobenzamide, m.p. 233–235° C. |
| 157 | N-[4-[(5,6,7,8-Tetrahydro-8-oxo-4H-thieno[3,2-b]azepin-4-yl)carbonyl]-phenyl]-2-methylbenzamide |
| 158 | N-[4-[(5,6,7,8-Tetrahydro-8-oxo-4H-thieno[3,2-b]azepin-4-yl)carbonyl]-phenyl]-2-(trifluoromethyl)-4-fluorobenzamide |
| 159 | N-[4-[(5,6,7,8-Tetrahydro-8-oxo-4H-thieno[3,2-b]azepin-4-yl)carbonyl]-phenyl]-4-fluoro-2-methylbenzamide |
| 160 | N-[4-[(5,6,7,8-Tetrahydro-8-oxo-4H-thieno[3,2-b]azepin-4-yl)carbonyl]-phenyl]-5-fluoro-2-methylbenzamide |
| 161 | N-[4-[(5,6,7,8-Tetrahydro-8-oxo-4H-thieno[3,2-b]azepin-4-yl]carbonyl]-3-chlorophenyl]-3-fluoro-2-methylbenzamide |
| 162 | N-[4-[(5,6,7,8-Tetrahydro-8-oxo-4H-thieno[3,2-b]azepin-4-yl]carbonyl]-3-chlorophenyl]-2,3-dimethylbenzamide |
| 163 | N-[4-[(5,6,7,8-Tetrahydro-8-oxo-4H-thieno[3,2-b]azepin-4-yl]carbonyl]-3-chlorophenyl]-2,3-dichlorobenzamide |
| 164 | N-[4-[(5,6,7,8-Tetrahydro-8-oxo-4H-thieno[3,2-b]azepin-4-yl]carbonyl]-3-chlorophenyl]-2-(trifluoromethoxy)-benzamide |
| 165 | N-[4-[(5,6,7,8-Tetrahydro-8-oxo-4H-thieno[3,2-b]azepin-4-yl]carbonyl]-3-chlorophenyl]-2,6-dichlorobenzamide |
| 166 | N-[4-[(5,6,7,8-Tetrahydro-8-oxo-4H-thieno[3,2-b]azepin-4-yl]carbonyl]-3-chlorophenyl]-2-(methylthio)benzamide |
| 167 | N-[4-[(5,6,7,8-Tetrahydro-8-oxo-4H-thieno[3,2-b]azepin-4-yl]carbonyl]-3-chlorophenyl]-3-methyl-2-thiophene-carboxamide |
| 168 | N-[4-[(5,6,7,8-Tetrahydro-8-oxo-4H-thieno[3,2-b]azepin-4-yl]carbonyl]-3-chlorophenyl]-3-methyl-2-furane-carboxamide |
| 169 | N-[4-[(5,6,7,8-Tetrahydro-8-oxo-4H-thieno[3,2-b]azepin-4-yl]carbonyl]-3-chlorophenyl]-2-methyl-3-chloro-benzamide |
| 170 | N-[4-[(5,6,7,8-Tetrahydro-8-oxo-4H-thieno[3,2-b]azepin-4-yl]carbonyl]-3-methoxyphenyl]-3-fluoro-2-methyl-benzamide |
| 171 | N-[4-[(5,6,7,8-Tetrahydro-8-oxo-4H-thieno[3,2-b]azepin-4-yl]carbonyl]-3-methoxyphenyl]-5-fluoro-2-methyl-benzamide |
| 172 | N-[4-[(5,6,7,8-Tetrahydro-8-oxo-4H-thieno[3,2-b]azepin-4-yl]carbonyl]-2-chlorophenyl]-2,4-dichlorobenzamide |
| 173 | N-[4-[(5,6,7,8-Tetrahydro-8-oxo-4H-thieno[3,2-b]azepin-4-yl]carbonyl]-2-chlorophenyl]-2-methylbenzamide |
| 174 | N-[4-[(5,6,7,8-Tetrahydro-8-oxo-4H-thieno[3,2-b]azepin-4-yl]carbonyl]-2-chlorophenyl]-3-fluoro-2-methylbenzamide |
| 175 | N-[4-[(5,6,7,8-Tetrahydro-8-oxo-4H-thieno[3,2-b]azepin-4-yl]carbonyl]-2-chlorophenyl]-5-fluoro-2-methylbenzamide |
| 176 | N-[4-[(5,6,7,8-Tetrahydro-8-oxo-4H-thieno[3,2-b]azepin-4-yl]carbonyl]-2-chlorophenyl]-2-(trifluoromethyl)-benzamide |
| 177 | N-[4-[(5,6,7,8-Tetrahydro-8-oxo-4H-thieno[3,2-b]azepin-4-yl]carbonyl]-2-chlorophenyl]-2-methyl-4-fluorobenzamide |

EXAMPLE 178

4-[(2-(3-Pyridinyl)thiazol-4-ylcarbonyl]5,6,7,8-tetrahydro-4H-thieno[3,2-b]azepine To a cooled (0° C.) solution of 2 mmol of 5,6,7,8-tetrahydro-4H-thieno[3,2-b]azepine, 6 mmol of N,N-diisopropylethylamine in 8 ml of dichloromethane added 2.2 mmol of 2-(3-pyridinyl)thiazole-4-carbonyl chloride. The mixture is stirred at room temperature for 16 hours and diluted with 50 ml of dichloromethane and 25 ml of water. The organic layer is separated, washed with $H_2O$, 1N $NaHCO_3$, brine and dried ($Na_2SO_4$). The solvent is removed under vacuum and the residue chromatographed on silica gel with ethyl acetate-hexane as solvent to give the product as a solid.

EXAMPLE 179

N-[4-[5,6,7,8-Tetrahydro-4H-thieno[3,2-b]-4-yl)carbonyl]phenyl]-4-oxo-4,5,6,7-tetrahydrohdrobenzo[b]furan-3-carboxamide A solution of 240 mg of 4-oxo-4,5,6,7-tetrahydrobenzo[b]furan-3-carbonyl chloride in 3 ml of methylene chloride is cooled to 0° C. and while stirring 209 μl of triethylamine is added followed by 273 mg of 4-(4-aminobenzoyl)-5,6,7,8-tetrahydro-4H-thieno[3,2-b]azepine. Stirring is continued at room temperature under argon for 18 hours. An additional 240 mg of acid chloride and 209 μl of triethylamine in 1 ml of methylene chloride is added. Stirring is continued for 2 hours, heating at reflux for 3 hours and stirring at room temperature for 18 hours. The reaction mixture is concentrated in vacuo, diluted with 30 ml of ethyl acetate and washed with 12 ml each of water, 2N citric acid, 1M sodium bicarbonate, brine and dried over $Na_2SO_4$. The organic layer is concentrated in vacuo to a foam which is purified by chromatography on a silica gel preparative plate using 1:1 ethyl acetate-hexane to give 60 mg of the desired product as a white solid, m.p. 188°–192° C.

EXAMPLE 180

N-[4-[5,6,7,8-Tetrahydro-4H-thieno[3,2-b]-4-yl)carbonyl]phenyl]-indole-5-carboxamide To a solution of 250 mg of indole-5-carboxylic acid in 5 ml of tetrahydrofuran at 0° C. is added 327 mg of N,N-carbonyldiimidazole followed by stirring for 2 hours. The volatiles are evaporated to a residue in vacuo. To the residue is added 352 mg of 4-(4-aminobenzoyl)-5,6,7,8-tetrahydro-4H-thieno[3,2-b]azepine followed by heating at 100° C. for 18 hours. The temperature is increased to 120° C. and heating continued for an additional 4 hours. The reaction mixture is cooled to room temperature and diluted with 40 ml of ethyl acetate which is washed with water. The organic layer is dried with $Na_2SO_4$ and concentrated in vacuo to a residue which is purified by chromatography on preparative plates by elution with 1:1 ethyl acetate-hexane to give 175 mg of the desired product as a white solid (from ethyl acetate).

EXAMPLE 181

N-[5-[(5,6,7,8-Tetrahydro-4H-thieno[3,2-b]azepin-4-yl)carbonyl]-2-pyridinyl]-2-methylfurane-3-carboxamide A solution of 2 mmol of 5,6,7,8-tetrahydro-4H-thieno[3,2-b]azepine, 5 mmol of N,N-diisopropylethylamine and 2.2 mmol of 6-[(3-methyl-2-furanylacetyl)amino]pyridine-3-carbonyl chloride in 10 ml of $CH_2Cl_2$ is stirred at room temperature for 16 hours. The mixture is diluted with 50 ml of $CH_2Cl_2$ and 25 ml of water and the organic layer separated. The organic layer is washed with $H_2O$, 1N $NaHCO_3$, brine and dried ($Na_2SO_4$). The solvent is removed and the residue is chromatographed on silica gel with ethyl acetate-hexane as solvent to give the product as a solid.

EXAMPLE 182

N-[4-[(5,6,7,8-Tetrahydro-4H-thieno[3,2-b]azepin-4-yl)carbonyl]phenyl]-2-dimethylamino)-pyridine-3-carboxamide A mixture of 1.0 g of N-[4-(5,6,7,8-tetrahydro-4H-thieno[3,2-b]azepin-4-yl)carbonyl]phenyl]-2-chloropyridine-3-carboxamide, 1 g of $K_2CO_3$, 10 ml of aqueous dimethylamine (40 wt % solution in water) in 25 ml of dimethylsulfoxide is heated at 100° C. for 8 hours. The mixture is poured into ice-water and filtered. The solid is washed with water, dried and chromatographed on silica gel with ethyl acetate-methanol as solvent to give the product as a solid.

EXAMPLE 183

N-[4-[5,6,7,8-Tetrahydro-4H-thieno[3,2-b]azepin-4-yl)carbonyl]-3-chlorophenyl]-2-chloro-4-fluorobenzamide To a solution of 0.50 g of 4-(2-chloro-4-aminobenzoyl)-5,6,7,8-tetrahydro-4H-thieno[3,2-b]azepine and 342 μl of triethylamine in 3.5 ml of dichloromethane cooled to 0° C. is added a solution of 0.394 g of 2-chloro-4-fluorobenzoyl chloride in 1.5 ml of dichloromethane. The mixture is stirred at room temperature overnight under argon and added 50 ml of dichloromethane and 20 ml of $H_2O$. The $CH_2Cl_2$ is separated and washed with 20 ml each of 2N citric acid, 1M $NaHCO_3$ and brine. From the $CH_2C_{12}$ is obtained 0.59 g of white crystals, m.p. 219°–221° C.

EXAMPLE 184

N-[4-[(5,6-Dihydro-4H-thieno[3,2-b]azepin-4-yl)carbonyl]-3-chlorophenyl]-5-fluoro-2-methylbenzamide To a cooled solution of 0.20 g of 4-(2-chloro-4-aminobenzoyl)-5,6-dihydro-4H-thieno [3,2-b]azepine and 137 μl of triethylamine in 3 ml of dichloromethane is added a solution of 0.142 g of 5-fluoro-2-methylbenzoyl chloride in 1 ml of dichloromethane. The mixture is stirred under argon for 2 days and diluted with 30 ml of dichloromethane and 15 ml of $H_2O$. The organic layer is separated and washed with 15 ml each of 2N citric acid, 1M $NaHCO_3$, brine and dried ($Na_2SO_4$). The solution is filtered through a thin pad of hydrous magnesium silicate, the filter pad washed with dichloromethane and the filtrate evaporated. The residue is crystallized from ethyl acetate to give 0.215 g of white crystals, m.p. 125°–132° C.

The following compounds are prepared as described in Example 184.

| Example No. | Compound |
|---|---|
| 185 | N-[4-[5,6-Tetrahydro-4H-thieno[3,2-b]-azepin-4-yl)carbonyl]-3-chlorophenyl]-3-fluoro-2-methylbenzamide |
| 186 | N-[4-[5,6-Tetrahydro-4H-thieno[3,2-b]-azepin-4-yl)carbonyl]-3 -chlorophenyl]-2 -chloro-4-fluorobenzamide |
| 187 | N-[4-[5,6-Tetrahydro-4H-thieno[3,2-b]-azepin-4-yl)carbonyl]-3-chlorophenyl]-2, 3 -dimethylbenzamide |
| 188 | N-[4-[5,6-Tetrahydro-4H-thieno[3,2-b]-azepin-4-yl)carbonyl]-3-chiorophenyl]-2, 5-dimethylbenzamide |
| 189 | N-[4-[5,6-Tetrahydro-4H-thieno[3,2-b]-azepin-4-yl)carbonyl]-3-chlorophenyl]-2, 4-dichlorobenzamide |
| 190 | N-[4-[5,6-Tetrahydro-4H-thieno[3,2-b]-azepin-4-yl)carbonyl]-3-chiorophenyl]-2- (trifluoromethyl )benzamide |
| 191 | N-[4-[5,6-Tetrahydro-4H-thieno[3,2-b]-azepin-4-yl)carbonyl]-3-chlorophenyl]-2-(methylthio)benzamide |

-continued

| Example No. | Compound |
|---|---|
| 192 | N-[4-[5,6-Tetrahydro-4H-thieno[3,2-b]-azepin-4-yl)carbonyl]-3-chlorophenyl]-2-methoxybenzamide |
| 193 | N-[4-[5,6-Tetrahydro-4H-thieno[3,2-b]-azepin-4-yl)carbonyl]-3-chlorophenyl]-2-chlorobenzamide |
| 194 | N-[4-[5,6-Tetrahydro-4H-thieno[3,2-b]-azepin-4-yl)carbonyl]-3-chlorophenyl]-2-(trifluoromethoxy)benzamide |
| 195 | N-[4-[5,6-Tetrahydro-4H-thieno[3,2-b]-azepin-4-yl)carbonyl]-3-chlorophenyl]-2-chloro-6-fluorobenzamide |
| 196 | N-[4-[5,6-Tetrahydro-4H-thieno[3,2-b]-azepin-4-yl)carbonyl]-3-chlorophenyl]-2-chloro-5-fluorobenzamide |
| 197 | N-[4-[5,6-Tetrahydro-4H-thieno[3,2-b]-azepin-4-yl)carbonyl]-3-chlorophenyl]-4-fluoro-2-(trifluoromethyl)benzamide |
| 198 | N-[4-[5,6-Tetrahydro-4H-thieno[3,2-b]-azepin-4-yl)carbonyl]-3-chlorophenyl]-4-fluoro-2-methylbenzamide |
| 199 | N-[4-[5,6-Tetrahydro-4H-thieno[3,2-b]-azepin-4-yl)carbonyl]-3-chlorophenyl]-2-methyl-3-thiophenecarboxamide |
| 200 | N-[4-[5,6-Tetrahydro-4H-thieno[3,2-b]-azepin-4-yl)carbonyl]-3-chlorophenyl]-3 -methyl-2-thiophenecarboxamide |
| 201 | N-[4-[5,6-Tetrahydro-4H-thieno[3,2-b]-azepin-4-yl)carbonyl]-3-chlorophenyl]-2-methylbenzeneacetamide |
| 202 | N-[4-[5,6-Tetrahydro-4H-thieno[3,2-b]-azepin-4-yl)carbonyl]-3-chlorophenyl]-2-chlorobenzeneacetamide |
| 203 | N-[4-[2-Chloro-5, 6-tetrahydro-4H-thieno-[3,2-b]azepin-4-yl)carbonyl]-3-chloro-phenyl]-5-fluoro-2 -methylbenzamide |
| 204 | N-[4-[2-Chloro-5,6-tetrahydro-4H-thieno-[3,2-b]azepin-4-yl)carbonyl]-3-chloro-phenyl]-3-fluoro-2-methylbenzamide |
| 205 | N-[4-[2-Chloro-5, 6-tetrahydro-4H-thieno-[3,2-b]azepin-4-yl)carbonyl]-3-chloro-phenyl]-2-chloro-4-fluorobenzamide |
| 206 | N-[4-[2-Chloro-5,6-tetrahydro-4H-thieno-[3,2-b]azepin-4-yl)carbonyl]-3 -chloro-phenyl]-2,4-dichiorobenzamide |
| 207 | N-[4-[2-Chloro-5,6-tetrahydro-4H-thieno-[3,2-b]azepin-4-yl)carbonyl]phenyl]-5-fluoro-2 -methylbenzamide |
| 208 | N-[4-[2-Chioro-5,6-tetrahydro-4H-thieno-[3,2-b]azepin-4-yl)carbonyl]phenyl]-3-fluoro-2-methylbenzamide |
| 209 | N-[4-[2-Chioro-5,6-tetrahydro-4H-thieno-[3,2-biazepin-4-yl)carbonyl]phenyl]-2-chloro-4-fluorobenzamide |
| 210 | N-[4-[2-Chloro-5,6-tetrahydro-4H-thieno-[3,2-b]azepin-4-yl)carbonyl]phenyl]-2,3- |
| 211 | N-[4-[2-Chloro-5,6-tetrahydro-4H-thieno-[312-b]azepin-4-yl)carbonyl]phenyl]-2,4-dichlorobenzamide |
| 212 | N-[4-[2-Chloro-5,6-tetrahydro-4H-thieno-[3,2-b]azepin-4-yl)carbonyl]phenyl]-2,5-dimethylbenzamide |
| 213 | N-[4-[2-Chloro-5,6-tetrahydro-4H-thieno-[3 ,2-b]azepin-4-yl)carbonyl]phenyl]-2-(trifluoromethyl) benzamide |
| 214 | N-[4-[2-Chloro-5,6-tetrahydro-4H-thieno-[3,2-b]azepin-4-yl) carbonyl]phenyl]-2-(methylthio)benzamide |
| 215 | N-[4-[2-Chloro-5,6-tetrahydro-4H-thieno-[3 12-b]azepin-4-yl) carbonyl]phenyl]-2-chlorobenzamide |
| 216 | N-[4-[2-Chloro-5,6-tetrahydro-4H-thieno-[3 12-b]azepin-4-yl)carbonyl]phenyl]-2-chloro-5-fluorobenzamide |
| 217 | N-[4-[2-Chloro-5,6-tetrahydro-4H-thieno-[3,2-b]azepin-4-yl)carbonyl]phenyl]-2-chloro-6-fluorobenzamide |
| 218 | N-[4-[2-Chloro-5,6-tetrahydro-4H-thieno-[3, 2-b]azepin-4-yl)carbonyl]phenyl]-2-methyl-4-fluorobenzamide |
| 219 | N-[4-[2-Chloro-5,6-tetrahydro-4H-thieno-[3,2-b]azepin-4-yl)carbonyl]phenyl]-2-methylbenzeneacetamide |
| 220 | N-[4-[2-Chloro-5,6-tetrahydro-4H-thieno-[3 12-b]azepin-4-yl)carbonyl]phenyl]-3-methyl-2-thiophenecarboxamide |

The following compounds are prepared as described in Example 183.

| Ex. No. | |
|---|---|
| 221 | N-[4-[2-Chloro-5,6,7,8-tetrahydro-4H-thieno[3,2-b]azepin-4-yl)carbonyl]-3-methylphenyl]-3-fluoro-2-methylbenzamide |
| 222 | N-[4-[2-Chloro-5,6,7,8-tetrahydro-4H-thieno [3, 2-b]azepin-4-yl) carbonyl]-3 -methylphenyl]-5-fluoro-2 -methylbenzamide |
| 223 | N-[4-[2-Chloro-5,6,7,8-tetrahydro-4H-thieno[3,2 -b]azepin-4-yl)carbonyl]-3 -methylphenyl]-2-chloro-4 -fluorobenzamide |
| 224 | N-[4-[2-Chloro-5,6,7,8-tetrahydro-4H-thieno[3,2-b]azepin-4-yl)carbonyl]-3-methylphenyl]-2,3-dimethylbenzamide |
| 225 | N-[4-[2-Chloro-5,6,7,8-tetrahydro-4H-thieno[3,2-b]azepin-4-yl)carbonyl]-3-methylphenyl]-2,5-dichlorobenzamide |
| 226 | N-[4-[2-Chloro-5,6,7,8-tetrahydro-4H-thieno[3,2-b]azepin-4-yl)carbonyl]-3-methylphenyl]-2,4-dichiorobenzamide |
| 227 | N-[4-[2-Chloro-5,6,7,8-tetrahydro-4H-thieno[3,2-b]azepin-4-yl)carbonyl]-3-methylphenyl]-2-(trifluoromethyl)benz-amide |
| 228 | N-[4-[2-Chloro-5,6,7,8-tetrahydro-4H-thieno [3,2-b]azepin-4-yl)carbonyl]-3-methylphenyl]-2 -chlorobenzamide |
| 229 | N-[4-[2-Chloro-5,6,7,8-tetrahydro-4H-thieno[3,2-b]azepin-4-yl)carbonyl]-3-methylphenyl]-2-chloro-5-fluorobenzamide |
| 230 | N-[4-[2-Chloro-5,6,7,8-tetrahydro-4H-thieno[3,2-b]azepin-4-yl)carbonyl]-3-inethylphenyl]-2-(trifluoromethyl)benz-amide |
| 231 | N-[4-[2-Chloro-5,6,7,8-tetrahydro-4H-thieno[3,2-b]azepin-4-yl)carbonyl]-3-methylphenyl]-2-methylbenzeneacetamide |
| 232 | N-[4-[2-Chloro-5,6,7,8-tetrahydro-4H-thieno[3,2-b]azepin-4-yl)carbonyl]-3-methyl-2-thiophenecarboxamide |

EXAMPLE 233

4-[4- (n-Butyloxy)benzoyl]-5,6,7,8-tetrahydro-4H-thieno[3,2-b]azepine

To a chilled (0° C.) solution of 0.306 g of 5,6,7,8-tetrahydro-4H-thieno[3,2-b]azepine and 417 µl of triethylamine is added 474 µl of 4-(n-butoxy)benzoyl chloride. The mixture is stirred for 3 days at room temperature, diluted with 50 ml of dichloromethane and ml of water. The organic layer is separated and washed with 20 ml each of 2N citric acid, 1M $NaHCO_3$, brine and dried ($Na_2SO_4$). The solution is filtered through a thin pad of hydrous magnesium silicate, the pad washed with $CH_2Cl_2$ and the filtrate evaporated. The residue is crystallized from hexane containing a small amount of ethyl acetate. The crystals (0.585 g) are purified by chromatography on silica gel plates with hexane-ethyl acetate (2:1) as solvent to give 0.40 g of crystals (from ethyl acetate-hexane), m.p. 87° C. to 90° C.

The following compounds are prepared as described in Example 233.

| Ex. No. | |
|---|---|
| 234 | 4-[4-(2-Methylbutyloxy)benzoyl]-5,6,7,8-tetrahydro-4H-thieno[3,2-b]azepine |
| 235 | 4-[4-(3-Methylbutyloxy)benzoyl]-5,6,7,8-tetrahydro-4H-thieno [3,2-b]azepine |
| 236 | 4-[4-(Benzyloxy)benzoyl]-5,6,7,8-tetrahydro-4H-thieno[3,2-b]azepine |
| 237 | 4-[4-(2-chlorobenzyloxy)benzoyl]-5,6,7,8-tetrahydro-4H-thieno[3,2-b]azepine |
| 238 | 4-[4-[2-(cyclopentyl)ethyloxy]benzoyl]-5,6,7,8-tetrahydro-4H-thieno[3,2-b]-azepine |
| 239 | 4-[4-[2-(cyclohexyl)ethyloxy]benzoyl]-5,6,7,8-tetrahydro-4H-thieno[3,2-b]azepine |
| 240 | 4-[4-(cyclopentyl)methoxy]benzoyl]-5,6,7,8-tetrahydro-4H-thieno[3,2-b]azepine |
| 241 | 4-[4-(cyclohexyl)methoxy]benzoyl]-5,6,7,8-tetrahydro-4H-thieno[3,2-b]-azepine |
| 242 | 4- [4-(3-Dimethylbutyloxy)benzoyl]-5,6,7,8-tetrahydro-4H-thieno[3,2-b]-azepine |

EXAMPLE 243

N-[5-[(5,6,7,8-tetrahydro-4H-thieno[3,2-b]azepin-4-yl)carbonyl]-2-pyridinyl]-5-fluoro-2-methylbenzamide To a cooled (0° C.) mixture of 0.306 g of 5,6,7,8-tetrahydro-4H-thieno[3,2-b]azepine and 1.11 µl of triethylamine in 5 ml of dichloromethane is added 1.17 g of 6-[(5-fluoro-2-methylbenzoyl)amino]pyridine-3-carbonyl chloride and the mixture is stirred overnight at room temperature under argon. The mixture is diluted with 50 ml of dichloromethane and 20 ml of water and the organic layer separated. The organic layer is washed with 20 ml each of 1M $NaHCO_3$, brine and dried ($Na_2SO_4$). The solution is filtered through a thin pad of hydrous magnesium silicate and the filtrate evaporated, concentrated to dryness under vacuum to give a glass. Crystallization from ethyl acetate-hexane gives 0.35 g of white crystals, m.p. 178°–180° C.

As described for Example 243, the following compounds are prepared (Table C).

TABLE C

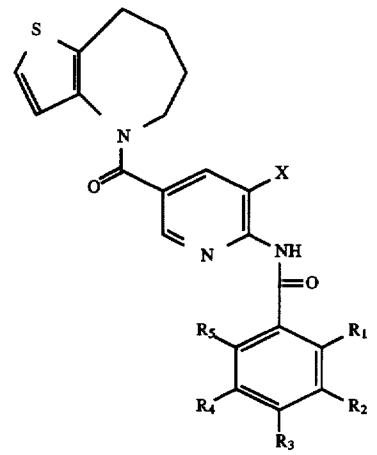

| Ex. No | $R_1$ | $R_2$ | $R_3$ | $R_4$ | $R_5$ | X |
|---|---|---|---|---|---|---|
| 244 | $CH_3$ | H | H | H | H | H |
| 245 | $CH_3$ | H | H | F | H | H |
| 246 | $CH_3$ | F | H | H | H | H |
| 247 | H | $OCH_3$ | $OCH_3$ | $OCH_3$ | H | H |
| 248 | Cl | H | H | H | H | H |
| 249 | F | H | F | H | H | H |
| 250 | Br | H | H | H | H | H |
| 251 | Cl | H | F | H | H | H |
| 252 | Ph | H | H | H | H | H |
| 253 | Cl | H | H | Br | H | H |
| 254 | $CH_3$ | H | H | H | H | Br |
| 255 | $CH_3$ | H | H | F | H | Cl |
| 256 | Cl | H | H | Cl | H | H |
| 257 | $CH_3$ | $CH_3$ | H | H | H | H |
| 258 | Cl | H | H | F | H | H |
| 259 | Cl | H | H | $CF_3$ | H | H |
| 260 | Cl | H | H | H | F | H |
| 261 | Cl | H | H | H | Cl | H |
| 262 | Cl | H | H | F | H | H |
| 263 | 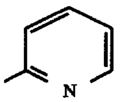 | H | H | H | H | H |
| 264 | 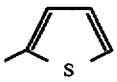 | H | H | H | H | H |
| 265 | $CH_3$ | H | H | H | $CH_3$ | H |
| 266 | Cl | H | H | F | H | Cl |
| 267 | Cl | H | F | H | H | Cl |
| 268 | Cl | Cl | H | H | H | H |
| 269 | Cl | H | H | Cl | H | H |
| 270 | $-OCH_3$ | H | H | H | H | H |
| 271 | $OCF_3$ | H | H | H | H | H |
| 272 | $-CF_3$ | H | H | H | H | H |
| 273 | Cl | Cl | H | Cl | H | H |
| 274 | $-SCH_3$ | H | H | H | H | H |
| 275 | Cl | H | $NO_2$ | H | H | H |
| 276 | $CH_3$ | H | H | $CH_3$ | H | H |
| 277 | F | H | H | Cl | H | H |
| 278 | Cl | H | H | $NH_2$ | H | H |
| 279 | F | $CF_3$ | H | H | H | H |
| 280 | $-OCH_3$ | H | H | Cl | H | H |
| 281 | Cl | H | H | $-SCH_3$ | H | H |
| 282 | F | H | H | H | $CF_3$ | H |
| 283 | F | H | $CF_3$ | H | H | H |
| 284 | $CF_3$ | H | F | H | H | H |
| 285 | $NO_2$ | H | H | H | H | H |
| 286 | F | H | H | H | H | H |
| 287 | Cl | H | $NH_2$ | H | H | H |

EXAMPLE 288

N-[5-[(5,6,7,8-Tetrahydro-4H-thieno[3,2-b]azepin-4-yl)carbonyl]-2-pyridinyl]-2-methylbenzeneacetamide To a cooled (0° C.) mixture of 0.306 g of 5,6,7,8-tetrahydro-4H-thieno[3,2-b]azepine and 1.11 μl of triethylamine in 5 ml of dichloromethane is added 1.2 g of 6-[(2-methylphenylacetyl)amino]pyridine-3-carbonyl chloride. The mixture is stirred at room temperature for 16 hours and diluted with 50 ml of dichloromethane. The mixture is washed with $H_2O$, 1N $NaHCO_3$, $H_2O$, brine and dried ($Na_2SO_4$). The solution is concentrated to dryness under vacuum and the residue chromatographed on silica gel to give the product as a solid.

As described for Example 288, the following compounds are prepared (Table D).

TABLE D

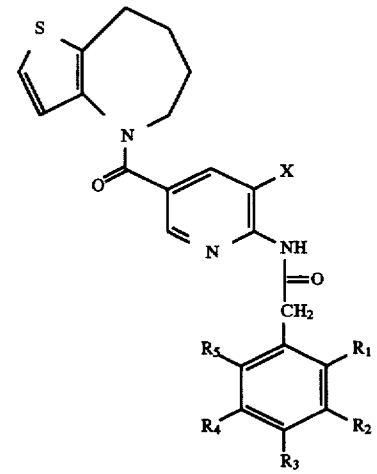

| Ex No. | $R_1$ | $R_2$ | $R_3$ | $R_4$ | $R_5$ | X |
|---|---|---|---|---|---|---|
| 289 | $CH_3$ | H | H | H | H | H |
| 290 | $CH_3$ | H | H | H | H | Br |
| 291 | $CH_3$ | H | H | H | H | Cl |
| 292 | Cl | H | H | H | H | H |
| 293 | Cl | H | H | H | H | Br |
| 294 | Cl | H | H | H | H | Cl |
| 295 | Cl | H | Cl | H | H | H |
| 296 | Cl | H | Cl | H | H | Br |
| 297 | Cl | H | Cl | H | H | Cl |
| 298 | $-OCH_3$ | H | H | H | H | H |
| 299 | $-OCH_3$ | H | H | H | H | Br |
| 300 | $-OCH_3$ | H | H | H | H | Cl |
| 301 | $-OCH_3$ | H | H | $-OCH_3$ | H | H |
| 302 | $-OCH_3$ | H | H | $-OCH_3$ | H | Br |
| 303 | $-OCH_3$ | H | H | $-OCH_3$ | H | Cl |
| 304 | H | $-OCH_3$ | $-OCH_3$ | H | H | H |
| 305 | H | $-OCH_3$ | $-OCH_3$ | H | H | Br |
| 306 | H | $-OCH_3$ | $-OCH_3$ | H | H | Cl |
| 307 | H | Cl | H | H | H | H |

TABLE D-continued

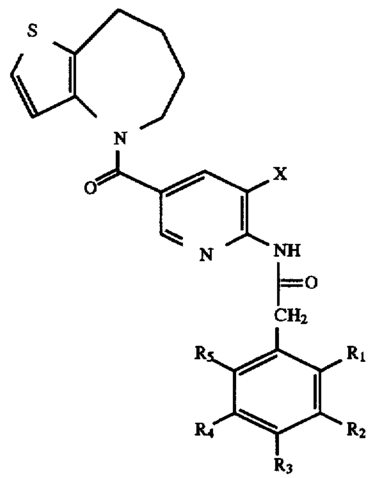

| Ex No. | $R_1$ | $R_2$ | $R_3$ | $R_4$ | $R_5$ | X |
|---|---|---|---|---|---|---|
| 308 | H | Cl | H | H | H | Br |
| 309 | H | Cl | H | H | H | Cl |
| 310 | H | H | Cl | H | H | H |
| 311 | H | H | Cl | H | H | Br |
| 312 | H | H | Cl | H | H | Cl |
| 313 | F | H | H | H | H | H |
| 314 | F | H | H | H | H | Br |
| 315 | F | H | H | H | H | Cl |
| 316 | H | F | H | H | H | H |
| 317 | H | F | H | H | H | Br |
| 318 | H | F | H | H | H | Cl |
| 319 | H | H | F | H | H | H |
| 320 | H | H | F | H | H | Br |
| 321 | H | H | F | H | H | Cl |
| 322 | H | $CH_3$ | H | H | H | H |
| 323 | H | $CH_3$ | H | H | H | Br |
| 324 | H | $CH_3$ | H | H | H | Cl |

EXAMPLE 325

5,6,7,8-Tetrahydro-4-[4-[[[(2-methylphenyl)amino]carbonyl]amino]benzoyl]-4H-thieno [3,2 -b]azepine A mixture of 0.409 g of 4-(4-aminobenzoyl)-5,6,7,8-tetrahydro-4H-thieno [3,2-b]azepine and 0.60 g of 2-methylphenylisocyanate in 2 ml of tetrahydrofuran is heated in an oil bath at 110° C. for 16 hours. The mixture is concentrated under vacuum and the residue chromatographed on preparative silica gel plates with ethyl acetate-hexane (1:1) as solvent to give a solid. Crystallization from ethyl acetate-hexane gives 0.33 g of white crystals, m.p. 179°-182° C.

The following compounds are prepared as described for Example 325 (Table E).

TABLE E

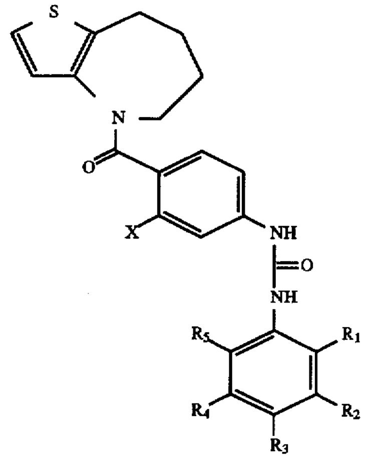

| Ex. No. | $R_1$ | $R_2$ | $R_3$ | $R_4$ | $R_5$ | X |
|---|---|---|---|---|---|---|
| 326 | $CH_3$ | $CH_3$ | H | H | H | H |
| 327 | $CH_3$ | H | H | H | H | Cl |
| 328 | $CH_3$ | H | H | H | H | $CH_3$ |
| 329 | $CH_3$ | H | Cl | H | H | H |
| 330 | $CH_3$ | H | H | $CH_3$ | H | Cl |
| 331 | $CH_3$ | H | H | F | H | Cl |
| 332 | $CH_3$ | F | H | H | H | H |
| 333 | Cl | H | H | H | H | Cl |
| 334 | Cl | H | H | F | H | Cl |
| 335 | Cl | H | H | H | H | H |
| 336 | Cl | H | F | H | H | Cl |
| 337 | Cl | Cl | H | H | H | Cl |
| 338 | $CH_3$ | H | H | H | Cl | H |
| 339 | $CF_3O$ | H | H | H | H | Cl |
| 340 | $CH_3S$ | H | H | H | H | Cl |
| 341 | Cl | Cl | H | Cl | H | $CH_3$ |
| 342 | Cl | H | H | H | F | Cl |
| 343 | H | $CF_3$ | H | H | H | Cl |
| 344 | H | $CF_3$ | H | H | H | H |
| 345 | $CF_3$ | H | Cl | H | H | Cl |
| 346 | $CH_3O$ | H | Cl | H | H | Cl |
| 347 | Cl | H | H | H | Cl | H |
| 348 | Cl | H | H | H | Cl | Cl |
| 349 | ϕ | H | H | H | H | Cl |
| 350 | ϕ | H | H | H | H | H |
| 351 | $CH_3$ | F | H | H | H | $CH_3$ |
| 352 | $CH_3$ | F | H | H | H | Cl |
| 353 | $CH_3$ | H | H | F | H | H |
| 354 | $CH_3$ | H | H | F | H | $CH_3$ |
| 355 | $CH_3$ | H | H | F | H | Cl |
| 356 | F | H | Cl | H | H | H |
| 357 | F | H | H | Cl | H | Cl |
| 358 | F | H | H | H | Cl | Cl |

EXAMPLE 359

5,6,7,8-Tetrahydro-4-[4-[[(methylphenylamino)] carbonyl]amino]benzoyl]-4H-thieno[3,2-b]azepine To a chilled (0° C.) solution of 0.409 g of 4-(4-aminobenzoyl)-5,6,7,8-tetrahydro-4H-thieno[3,2-b]azepine and 432 μl of N,N-diisopropylethylamine in 5 ml of dichloromethane is added under argon 0.336 g of N-phenyl-N-methylcarbamoyl chloride. The mixture is stirred overnight and an additional 0.672 g of N-phenyl-N-methylcarbamoyl chloride, 864 μl N,N-diisopropylethylamine and 10 ml of toluene added. The mixture refluxed 16 hours and the solvent removed under vacuum. The residue is chromatographed on silica gel with ethyl acetate-hexane (1:1) as solvent to give a solid. Crystallization from ethyl acetate-hexane gives 0.34 g of off-white crystals, m.p. 160°–162° C.

EXAMPLE 360

N-[4-[(5,6,7,8-Tetrahydro-4H-thieno[3,2-b]azepin-4-yl)carbonyl]-3-chlorophenyl][1,1'-biphenyl]-2-carboxamide As described for Example 1, a solution of 2 mmol of 4-(2-chloro-4-aminobenzoyl)-5,6,7,8-tetrahydro-4H-thieno [3,2-b]azepine and 5 mmol of triethylamine in 10 ml of dichloromethane under argon is reacted with [1,1'-biphenyl] -2-carbonyl chloride for 16 hours at room temperature to give the product as a solid.

EXAMPLE 361

4-[5-(2-Pyridinyl)thien-2-ylcarbonyl]-5,6,7,8-tetrahydro-4H-thieno[3,2-b]azepine To a cooled solution (0° C.) of 0.23 g of 5,6,7,8-tetrahydro-4H-thieno[3,2-b]azepine, 523 μl of N,N-diisopropylethylamine in 5 ml of dichloromethane is added 0.436 g of 5-(2-pyridinyl)thiophene-2-carbonyl chloride. The mixture is stirred at room temperature for 16 hours under argon and diluted with 40 ml of $CH_2Cl_2$ and 20 ml of water. The organic layer is separated and washed with 20 ml each of 1N $NaHCO_3$, brine and dried ($Na_2SO_4$). The solution is filtered through a thin pad of hydrous magnesium silicate and the filtrate concentrated to dryness. The residue is crystallized from ethyl acetate plus a small amount of hexane to give 0.485 g of tan crystals, m.p. 150°–154° C.

EXAMPLE 362

4-([1,1'-Biphenyl]-4-ylcarbonyl)-5,6,7,8-tetrahydro-4H-thieno[3,2-b]azepine

As described for Example 1, a solution of 2 mmol of 5,6,7,8-tetrahydro-4H-thieno[3,2-b]azepine, 5 mmol of triethylamine and 2.1 mmol of [1,1'-biphenyl]-4-carbonyl chloride in 10 ml of $CH_2Cl_2$ is stirred at room temperature for 16 hours to give the product as a solid.

The subject compounds of the present invention are tested for biological activity.

Binding Assay to Rat Hepatic $V_1$ Receptors

Rat liver plasma membranes expressing the vasopressin $V_1$ receptor subtypes are isolated by sucrose density gradient according to the method described by Lesko et al., (1973). These membranes are quickly suspended in 50.0 mMTris.HCl buffer, pH 7.4, containing 0.2% bovine serum albumin (BSA) and 0.1 mM phenylmethylsulfonylfluoride (PMSF) and kept frozen at −70° C. until used in subsequent binding experiments. For binding experiments, the following is added to the wells of a ninety-six well format microtiter plate: 100 μl of 100.0 mM Tris.HCl buffer containing 10.0 mM $MgCl_2$, 0.2% heat inactivated BSA and a mixture of protease inhibitors: leupeptin, 1.0 mg %; aprotinin, 1.0 mg %, 1,10-phenanthroline, 2.0 mg %; trypsin inhibitor, 10.0 mg % and 0.1 mM PMSF, 20.0 μl of [phenylalanyl-3,4,5-$^3$H]vasopressin (S.A. 45.1 Ci/mmole) at 0.8 nM, and the reaction initiated by the addition of 80 μl of tissue membranes containing 20 μg of tissue protein. The plates are kept undisturbed on the bench top at room temperature for 120 min. to reach equilibrium. Nonspecific samples are assayed in the presence of 0.1 μM of the unlabeled antagonist phenylalanylvasopressin, added in 20.0 μl volume to a final incubation volume of 200 μl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, OH).

Binding Assay to Rat Kidney Medullary $V_2$ Receptors

Medullary tissues from rat kidneys are dissected out, cut into small pieces and let soak in a 0.154 mM sodium chloride solution containing 1.0 mM EDTA with many changes of the liquid phase, until the solution is clear of blood. The tissue is homogenized in a 0.25M sucrose solution containing 1.0 mM EDTA and 0.1 mM PMSF using a Potter-Elvehjem homogenizer with a teflon pestle. The homogenate is filtered through several layers (4 layers) of cheese cloth. The filtrate is rehomogenized using a dounce homogenizer, with a tight fitting pestle. The final homogenate is contrifuged at 1500×g for 15 min. The nuclear pellet is discarded and the supernatant fluid recentrifuged at 40,000×g for 30 min. The resulting pellet formed contains a dark inner part with the exterior, slightly pink. The pink outer part is suspended in a small amount of 50.0 mMTris.HCl buffer, pH 7.4. The protein content is determined by the Lowry's method (Lowry et al, J. Biol. Chem., 1953). The membrane suspension is stored at −70° C., in 50.0 mMTris.HCl, containing 0.2% inactivated BSA and 0.1 mM PMSF in aliquots of 1.0 ml containing 10.0 mg protein per ml of suspension until use in subsequent binding experiments.

For binding experiments, the following is added in µl volume to wells of a 96 well format of a microtiter plate: 100.0 µl of 100.0 mM Tris.HCl buffer containing 0.2% heat inactivated BSA, 10.0 mM $MgCl_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 µl of [$^3$H]Arginine$^8$, vasopressin (S.A. 75.0 Ci/mmole) at 0.8 nM and the reaction initiated by the addition of 80.0 µl of tissue membranes (200.0 µg tissue protein). The plates are left undisturbed on the bench top for 120 min. to reach equilibrium. Non-specific binding is assessed in the presence of 1.0 µM of unlabeled ligand, added in 20 µl volume. For test compounds, these are solubilized in 50% dimethylsulfoxide (DMSO) and added in 20.0 µl volume to a final incubation volume of 200 µl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, OH).

Radioligand Binding Experiments with Human Platelet Membranes

Platelet Source: Hudson Valley Blood Services, Westchester Medical Center, Valhalla, N.Y.

Platelet Membrane Preparation:

Frozen platelet rich plasma (PRP), received from the Hudson Valley Blood Services are thawed to room temperature. The tubes containing the PRP are centrifuged at 16,000×g for 10 min. at 4° C. and the supernatant fluid discarded. The platelets resuspended in an equal volume of 50.0 mMTris.HCl, pH 7.5 containing 120 mM NaCl and 20.0 mM EDTA. The suspension is recentrifuged at 16,000×g for 10 min. This washing step is repeated one more time. The wash is discarded and the lysed pellets homogenized in low ionic strength buffer of Tris.HCl, 5.0 mM, pH 7.5 containing 5.0 mM EDTA. The homogenate is centrifuged at 39,000×g for 10 min. The resulting pellet is resuspended in Tris.HCl buffer, 70.0 mM, pH 7.5 and recentrifuged at 39,000×g for 10 min. The final pellet is resuspended in 50.0 mM Tris.HCl buffer pH 7.4 containing 120 mM NaCl and 5.0 mM HCl to give 1.0–2.0 mg protein per ml of suspension.

Binding to Vasopressin $V_1$Receptor Subtype in Human Platelet Membranes:

In wells of a 96 well format microtiter plate, add 100 µl of 50.0 mM Tris.HCl buffer containing 0.2% BSA and a mixture of protease inhibitors (aprotinin, leupeptin etc.). Then add 20 µl of [$^3$H]Ligand: (Manning or Arg$^8$Vasopressin), to give final concentrations ranging from 0.01 to 10.0 nM. Initiate the binding by adding 80.0 µl of platelet suspension (approx. 100 µg protein). Mix all reagents by pipetting the mixture up and down a few times. Non-specific binding is measured in the presence of 1.0 µM of unlabeled ligand (Manning or Arg$^8$Vasopressin). Let the mixture stand undisturbed at room temperature for ninety (90) min. Upon this time, rapidly filter off the incubate under vacuum suction over GF/B filters, using a Brandel® Harvester. Determine the radioactivity caught on the filter disks by the addition of liquid scintillant and counting in a liquid scintillator Binding to Membranes Of Mouse Fibroblast Cell Line (LV-2) Transfected with the cDNA expressing the Human $V_2$ Vasopressin Receptor Membrane Preparation Flasks of 175 ml capacity, containing attached cells grown to confluence are cleared of culture medium by aspiration. The flasks containing the attached cells are rinsed with 2×5 ml of phosphate buffered saline (PBS) and the liquid aspirated off each time. Finally, 5 ml of an enzyme free dissociation Hank's based solution (Specialty Media, Inc., Lafayette, N.J.) is added and the flasks are left undisturbed for 2 min. The content of all flasks is poured into a centrifuge tube and the cells pelleted at 300×g for 15 min. The Hank's based solution is aspirated off and the cells homo-genized with a polytron at setting #6 for 10 sec in 10.0 mM Tris.HCl buffer, pH 7.4 containing 0.25M sucrose and 1.0 mM EDTA. The homogenate is centrifuged at 1500×g for 10 min to remove ghost membranes. The supernatant fluid is centrifuged at 100,000×g for 60 min to pellet the receptor protein. Upon completion, the pellet is resuspended in a small volume of 50.0 mM Tris.HCl buffer, pH 7.4. The protein content is determined by the Lowry method and the receptor membranes are suspended in 50.0 mM Tris.HCl buffer containing 0.1 mM phenylmethylsulfonylfluoride (PMSF) and 0.2% bovine serum albumin (BSA) to give 2.5 mg receptor protein per ml of suspension.

Receptor Binding

For binding experiments, the following is added in µl volume to wells of a 96 well format of a microtiter plate: 100.0 µl of 100.0 mM Tris.HCl buffer containing 0.2% heat inactivated BSA, 10.0 mM $MgCl_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 µl of [$^3$H]Arginine$^8$, vasopressin (S.A. 75.0 Ci/mmole) at 0.8 nM and the reaction initiated by the addition of 80.0 µl of tissue membranes (200.0 µg tissue protein). The plates are left undisturbed on the bench top for 120 min to reach equilibrium. Non-specific binding is assessed in the presence of 1.0 μM of unlabeled ligand, added in 20 μl volume. For test compounds, these are solubilized in 50% dimethylsulfoxide (DMSO) and added in 20.0 μl volume to a final incubation volume of 200 μl . Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, OH).

Vasopressin $V_2$ Antagonist Activity in conscious Hydrated Rats

Conscious hydrated rats are treated with compounds under study from 0.1 to 100 mg/kg orally or vehicle. Two to four rats are used for each compound. One hour later, arginine vasopressin (AVP, antidiuretic hormone, ADH) dissolved in peanut oil is administered at 0.4 μg/kg intraperitoneally. Two rats in each test would not receive arginine vasopressin but only the vehicle (peanut oil) to serve as water-loading control. Twenty minutes later each rat is given 30 mL/kg of deionized water orally by gavage and is placed individually in a metabolic cage equipped with a funnel and a graduated glass cylinder to collect urine for four hours. Urine volume is measured and osmolality analyzed by use of a Fiske One-Ten osmometer (Fiske Assoc., Norwood, Mass. USA). Urinary sodium, potassium, and chloride are analyzed by use of ion-specific electrodes in a Beckman E3 (Electrolyte 3) Analyzer.

In the following results, decreased urine volume and decreased osmolality relative to AVP-control indicates activity. The results of this test on representative compounds of this invention are shown in Table 3.

Vasopressin $V_1$ Antagonist Activity in Conscious Rats

Conscious rats are restrained in a supine position with elastic tape. The area at the base of the tail is locally anesthetization by subcutaneous infiltration with 2% procaine (0.2 ml). Using aseptic technique the ventral caudal tail artery is isolated and a cannula made of PE 10 and 20 (heat-fused) tubing is passed into the lower abdominal aorta. The cannula is secured, heparinized (1000 i.u./cc), sealed and the would closed with one or two stitches of Dexon 4-0. The caudal vein is also cannulated in the same manner for intravenous drug administration. The duration of the surgery is approximately 5 minutes. Additional local anesthesia (2% procaine or lidocaine) is provided as needed.

The animals are placed in plastic restraining cages in an upright position. The cannula is attached to a Starham P23Db pressure transducer and pulsatile blood pressure is recorded. Increase of systolic blood pressure responses to arginine vasopressin 0.01 and 0.2 international unit (I.U.) (350 I.U.=1 mg) injections are recorded prior to any drug (compound) administration, after which each rat is dosed orally with compounds under study 0.1–100 mg/kg (10 cc/kg) or intravenously 0.1–30 mg/kg (1 cc/kg). The vasopressin injections are repeated 30,60,90,120,180,240 and 300 min. later. Percentage of antagonism by the compound is calculated using the pre-drug vasopressin vasopressor response as 100%.

The results of this test on representative compounds of this invention are shown in Table 4.

TABLE 1

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

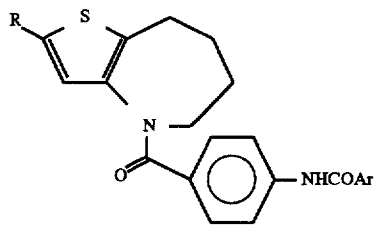

| | | | $IC_{50}$ (μM) | |
|---|---|---|---|---|
| Ex. No. | R | Ar | $V_1$ | $V_2$ |
| 3 | H | 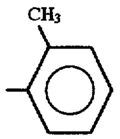 | 0.077 | 0.023 |
| 4 | H | 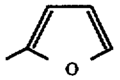 | 0.40 | 1.8 |
| 5 | H | 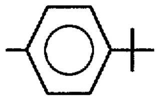 | 19% (50 μM) | 21.4 |
| 6 | H | 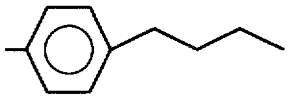 | 50 | 3.4 |
| 7 | H | 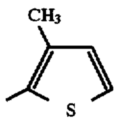 | 0.059 | 0.138 |
| 1 | H | 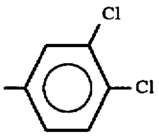 | 1.65 | 0.44 |
| 8 | H | 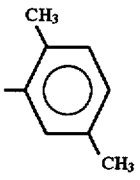 | 0.20 | 0.12 |
| 2 | H | 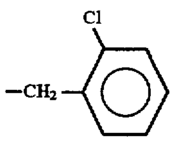 | 0.0037 | 0.0026 |

TABLE 1-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

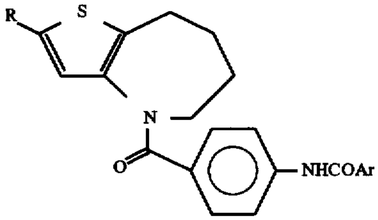

| | | | $IC_{50}$ (μM) | |
|---|---|---|---|---|
| Ex. No. | R | Ar | $V_1$ | $V_2$ |
| 9 | H | 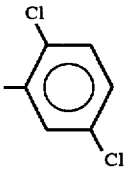 | 0.21 | 0.034 |
| 10 | H | 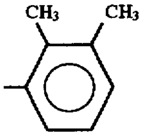 | 0.23 | 0.052 |
| 11 | H | 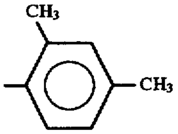 | 0.28 | 0.060 |
| 96 | Cl | 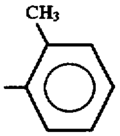 | 0.088 | 0.010 |
| 180 | H | 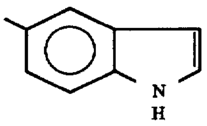 | 8.0 | 0.37 |
| 12 | H | 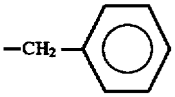 | 0.26 | 0.036 |
| 179 | H | 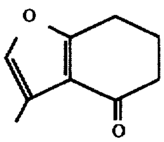 | 1.30 | 5.5 |
| 99 | Cl | 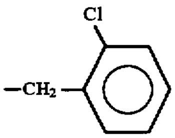 | 0.020 | 0.0033 |

TABLE 1-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

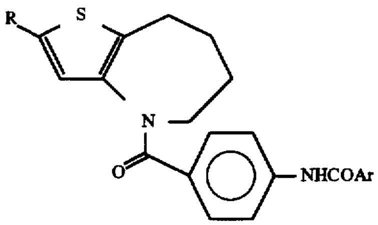

| | | | $IC_{50}$ (μM) | |
|---|---|---|---|---|
| Ex. No. | R | Ar | $V_1$ | $V_2$ |
| 13 | H | 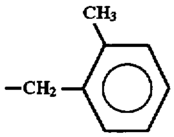 | 0.014 | 0.010 |
| 14 | H | 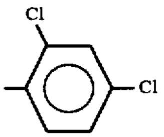 | 0.12 | 0.03 |
| 15 | H | 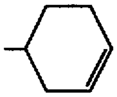 | 0.065 | 0.055 |
| 93 | Cl | 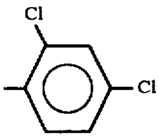 | 0.23 | 0.019 |
| 94 | Cl | 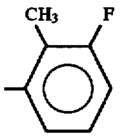 | 0.16 | 0.010 |
| 95 | Cl | 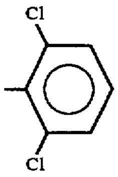 | 0.19* | 0.004** |

TABLE 2
Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor
Binding Assay to Rat Hepatic $V_1$ Receptors
| EX. NO. | STRUCTURE | $V_1$ $IC_{50}$ (μM) | $V_2$ $IC_{50}$ (μM) |
|---|---|---|---|
| 157 | 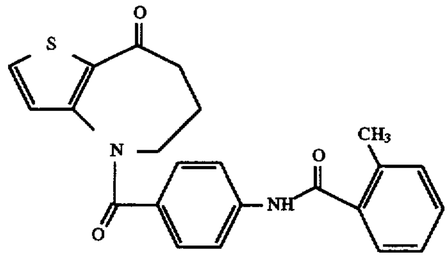 | 3.6 | 0.25 |
| 156 | 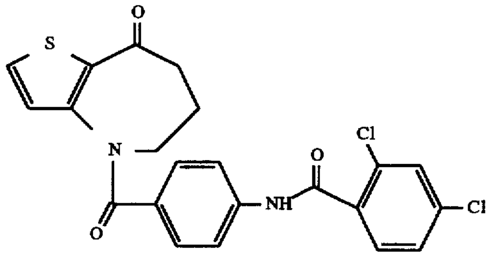 | 5.5 | 0.33 |
| 155 | 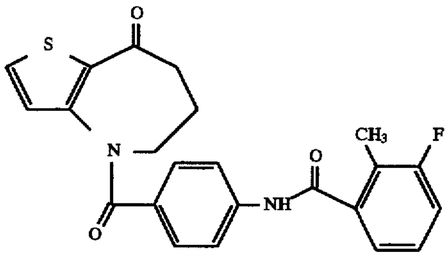 | 7.6 | 0.25 |
| 184 | 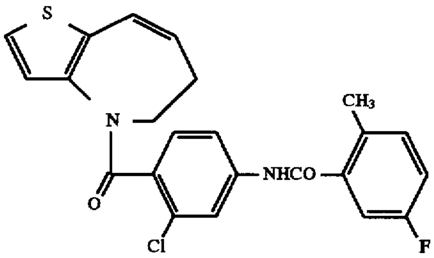 | *1.3 | 0.030 |
| 70 | 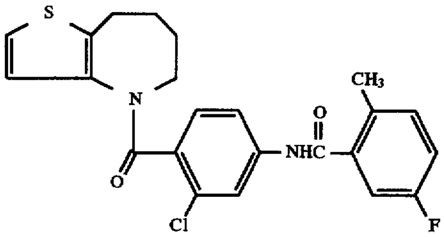 | 0.11* | 0.0034** |

TABLE 2-continued
Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor
Binding Assay to Rat Hepatic $V_1$ Receptors
| EX. NO. | STRUCTURE | $V_1$ $IC_{50}$ (μM) | $V_2$ $IC_{50}$ (μM) |
|---|---|---|---|
| 183 | 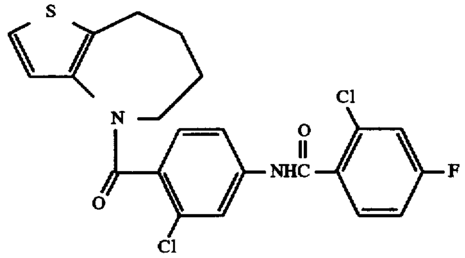 | 0.18* | 0.0022** |
| 68 | 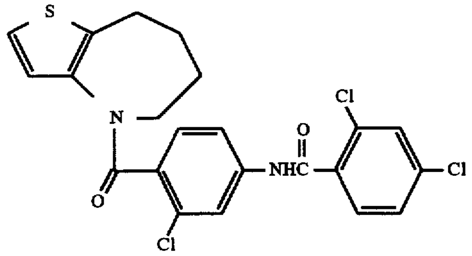 | 0.68* | 0.022** |
| 233 | 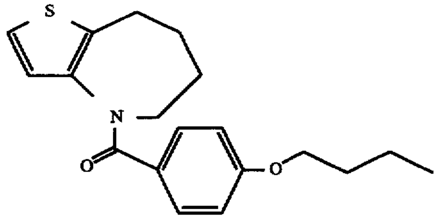 | 2% (10 μM) | 82% (10 μM) |
| 243 | 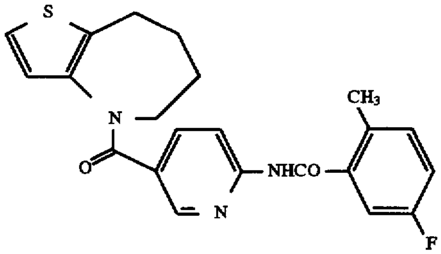 | 0.068 | 0.0061 |
| 252 | 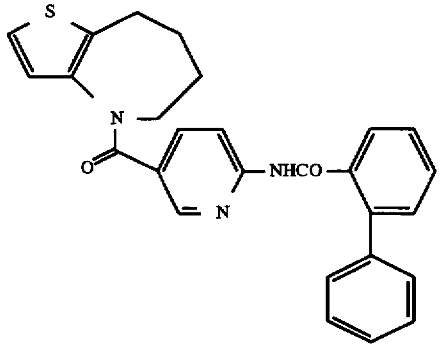 | 0.068 | 0.0061 |

TABLE 3

| Ex. No. | Dose P.O. mg/kg | N | Urine Volume ml/4 hours | Osmolality mOsm/kg |
|---|---|---|---|---|
| Vasopressin $V_2$ Antagonist Activity in Conscious Hydrated Rats | | | | |
| 3 | 100 | 2 | 10 | 1081 |
| 7 | 100 | 2 | 6.2 | |
| 2 | 10 | 4 | 2.8 | |
| 11 | 30 | 2 | 5 | 1420 |
| 96 | 30 | 2 | 16.1 | 465 |
| 99 | 30 | 2 | 10 | 1135 |
| 13 | 30 | 2 | 9.5 | 516 |
| 14 | 30 | 2 | 3.5 | 1432 |
| 15 | 30 | 2 | 4.6 | 1397 |
| 93 | 10 | 2 | 7.6 | 1056 |
| 94 | 10 | 2 | 8.8 | 910 |
| 157 | 10 | 2 | 6.5 | 1070 |
| 156 | 10 | 2 | 3.8 | 1266 |
| 155 | 10 | 2 | 4.5 | 1053 |
| 95 | 10 | 2 | 5 | 1122 |
| 70 | 10 | 2 | 4 | 1070 |
| 183 | 10 | 2 | 8.3 | 512 |
| 68 | 10 | 2 | 10.3 | 647 |

TABLE 4

| Ex. No. | Dose (mg/kg) | Max. % Inhibition | Time (Min) |
|---|---|---|---|
| Vasopressin (VAS) Vasopressor Response | | | |
| 2 | 10 iv | 7.6 | 60 |
| 9 | 30 po | 17 | 180 |
| 10 | 30 po | i | i |
| 96 | 10 iv | 65 | 90 |
| 99 | 10 iv | 58 | 90 |
| 13 | 10 iv | 80 | 60 |
| 14 | 20 iv | 61 | 120 |
| 15 | 10 iv | 69 | 30 |
| 93 | 20 iv | 77 | 90 |
| 94 | 20 iv | 74 | 90 |
| 157 | 20 iv | 66 | 60 |
| 156 | 20 iv | 63 | 240 |
| 155 | 20 iv | 62 | 60 |
| 95 | 10 iv | 61 | 30 |
| 70 | 20 iv | 67 | 120 |
| 183 | 30 iv | 78 | 120 |
| 68 | 20 iv | 50 | 120 |

Oxytocin Receptor Binding (a) Membrane Preparation

Female Sprague-Dawley rats weighing approximately 200–250 g are injected intramuscularly (i.m.) with 0.3 mg/kg of body weight of diethylstilbestrol (DES). The rats are sacrificed 18 hours later under pentobarbital anesthesia. The uteri are dissected out, cleaned of fat and connective tissues and rinsed in 50 ml of normal saline. The tissue pooled from six rats is homogenized in 50 ml of 0.01 mMTris.HCl, containing 0.5 mM dithiothreitol and 1.0 mM EDTA, adjusted to pH 7.4, using a polytron at setting 6 with three passes of 10 sec each. The homogenate is passed through two (2) layers of cheesecloth and the filtrate centrifuged at 1000×g for 10 min. The clear supernatant is removed and recentrifuged at 165,000×g for 30 min. The resulting pellet containing the oxytocin receptors is resuspended in 50.0 mM Tris.HCl containing 5.0 mM $MgCl_2$ at pH 7.4, to give a protein concentration of 2.5 mg/ml of tissue suspension. This preparation is used in subsequent binding assays with [$^3$H]Oxytocin.

(b) Radioligand Binding

Binding of 3,5-[$^3$H]Oxytocin ([$^3$H]OT) to its receptors is done in microtiter plates using [$^3$H]OT, at various concentrations, in an assay buffer of 50.0 mM Tris.HCl, pH 7.4 and containing 5.0 mM $MgCl_2$, and a mixture of protease inhibitors: BSA, 0.1 mg; aprotinin, 1.0 mg; 1,10-phenanthroline, 2.0 mg; trypsin, 10.0 mg; and PMSF, 0.3 mg per 100 ml of buffer solution. Nonspecific binding is determined in the presence of 1.0 uM unlabeled OT. The binding reaction is terminated after 60 min., at 22° C., by rapid filtration through glass fiber filters using a Brandel® cell harvester (Biomedical Research and Development Laboratories, Inc., Gaithersburg, Md.). Competition experiments are conducted at equilibrium using 1.0 nM [$^3$H]OT and varying the concentration of the displacing agents. The concentrations of agent displacing 50% of [$^3$H]OT at its sites ($IC_{50}$) are calculated by a computer assisted LUNDON-2 program (LUNDON SOFTWARE INC., Ohio, USA).

The results of this assay on representative examples are shown in Table 5.

TABLE 5

| Ex. No. | Conc. (μM) | % Inhibition | $IC_{50}$ (μM) |
|---|---|---|---|
| Oxytocin Binding Assay | | | |
| 9 | 10 | 60 | 5.2 |
| 13 | 10 | 95 | 0.68 |
| 68 | 10 | 55 | |
| 70 | 10 | 97 | 0.51 |
| 93 | 10 | 83 | 1.8 |
| 94 | 10 | 97 | 0.95 |
| 95 | 10 | 85 | 1.38 |
| 96 | 1.25 | 58 | 0.27 |
| 155 | 10 | 16 | |
| 156 | 10 | 0 | |
| 157 | 10 | 29 | |
| 183 | 10 | 86 | 0.6 |
| 184 | 10 | 76 | |
| 233 | 10 | 93 | 0.95 |
| 243 | 10 | 96 | 0.34 |
| 252 | 2.5 | 93 | 0.17 |

The compounds of the present invention can be used in the form of salts derived from pharmaceutically or physiologically acceptable acids or bases. These salts include, but are not limited to, the following: salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium or with organic bases. The compounds can also be used in the form of esters, carbamates and other conventional "pro-drug" forms, which, when administered in such form, convert to the active moiety in vivo.

When the compounds are employed for the above utilities, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The new tricyclic non-peptide vasopressin antagonists of this invention are useful in treating conditions where decreased vasopressin levels are desired, such as in congestive heart failure, in disease conditions with excess renal water reabsorption and in conditions with increased vascular resistance and coronary vasoconstriction.

In particular, the vasopressin antagonists of this invention are therapeutically useful in the treatment and/or prevention of hypertension, cardiac insufficiency, coronary vasospasm, cardiac ischemia, renal vasospasm, liver cirrhosis, congestive heart failure, nephritic syndrome, brain edema, cerebral ischemia, cerebral hemorrhage-stroke, thrombosis-bleeding and abnormal states of water retention.

In particular, the oxytocin antagonists of this invention are useful in the prevention of preterm labor and premature birth which is a significant cause of infant health problems and infant mortality.

What is claimed is:

1. A compound selected from Formula I:

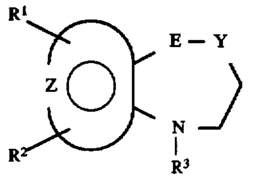

Formula I wherein:

$R^1$ and $R^2$ are selected from H, lower alkyl ($C_1$–$C_3$), lower alkoxy ($C_1$–$C_3$), or halogen;

E—Y is selected from the moieties —CH═CH—, —$CH_2CH_2$— or when Y is —$CH_2$—, E is selected from the moieties:

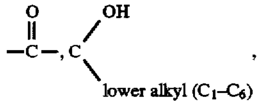

, —CHOH,

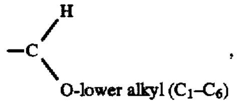

,

—CH—S-lower alkyl ($C_1$–$C_6$), —$CHNH_2$, —CHNH-lower alkyl($C_1$–$C_6$), —C[N-lower alkyl ($C_1$–$C_6$)]$_2$, —CHOCO-lower alkyl ($C_1$–$C_6$), —CHNH$(CH_2)_m$—$NH_2$, —CHNH$(CH_2)_m$—NH-lower alkyl ($C_1$–$C_6$), —CHNH$(CH_2)_m$—N[lower alkyl ($C_1$–$C_6$)]$_2$, —CHNH $(CH_2)_m$—S-lower alkyl ($C_1$–$C_6$), or —CHNH $(CH_2)_m$—O-lower alkyl ($C_1$–$C_6$);

m is an integer of 2 to 6;

the moiety

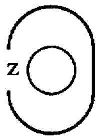

represents a fused 5-membered aromatic (unsaturated) heterocyclic ring having one heteroatom selected from O or S;

$R^3$ is —COAr, wherein Ar is a moiety selected from the group

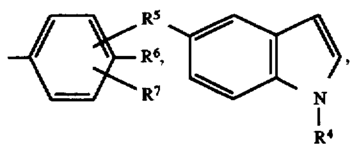

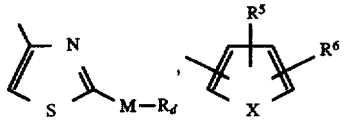

-continued and 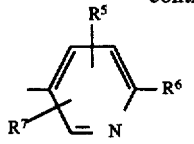

wherein:

in the moiety —M—$R_d$, when M is O, S, NH, $NCH_3$, $R_d$ is lower alkyl ($C_3$–$C_8$), lower alkenyl ($C_3$–$C_8$), or —$(CH_2)_p$-cycloalkyl($C_3$–$C_6$), and, when M is a bond or M is selected from O, S, NH or $NCH_3$, $R_d$ is selected from the moieties:

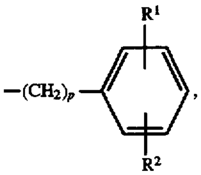, 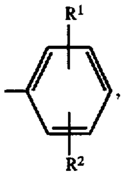,

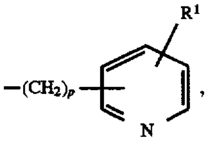,

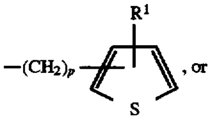, or 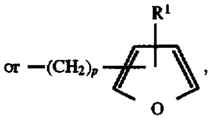, p is 0 to 4;

$R^1$ and $R^2$ are as hereinbefore defined;

X is selected from O, S, —NH, $NCH_3$ and —$NCOCH_3$;

$R^4$ is selected from H, lower alkyl ($C_1$–$C_3$), —CO-lower alkyl ($C_1$–$C_3$),

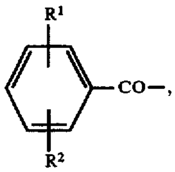, 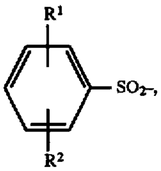, or

—$SO_2$-lower alkyl ($C_1$–$C_3$);

$R^1$ and $R^2$ are as defined above;

$R^5$ is selected from H, lower alkyl ($C_1$–$C_3$), lower alkoxy ($C_1$–$C_3$), and halogen;

$R^7$ is selected from H, lower alkyl ($C_1$–$C_3$), halogen, O-lower alkyl ($C_1$–$C_3$), and $CF_3$;

$R^6$ is selected from (a) the moieties of the formulae:

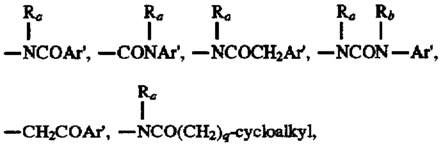

-continued

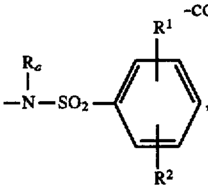, 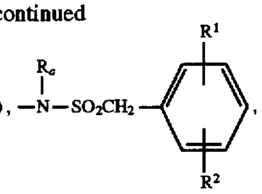,

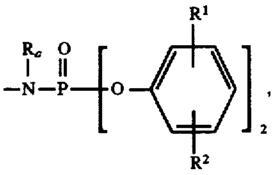, 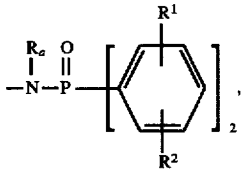,

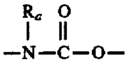

lower alkyl ($C_3$–$C_8$) straight or branched,

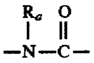

lower alkyl ($C_3$–$C_8$) straight or branched,

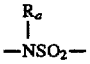

lower alkyl ($C_3$–$C_8$) straight or branched,

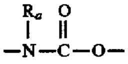

lower alkenyl ($C_3$–$C_8$) straight or branched,

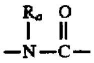

lower alkenyl ($C_3$–$C_8$) straight or branched,

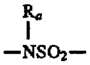

lower alkenyl ($C_3$–$C_8$) straight or branched, wherein $R^2$ is as defined hereinabove cycloalkyl is defined as $C_3$–$C_6$ cycloalkyl, cyclohexenyl or cyclopentenyl;

$R_a$ is independently selected from hydrogen, —$CH_3$, —$C_2H_5$, moieties of the formulae:

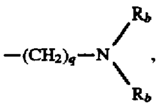, 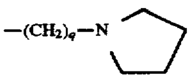,

-continued

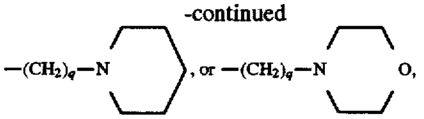

—$(CH_2)_q$—O-lower alkyl ($C_1$–$C_3$) or —$CH_2CH_2OH$;

q is one, two or three;

$R_b$ is independently selected from H, —$CH_3$, or —$C_2H_5$;

Ar' is selected from the moieties of the formula:

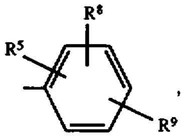
,
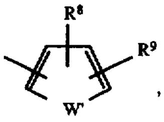
,
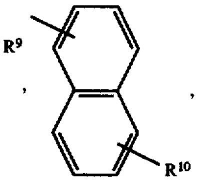
,

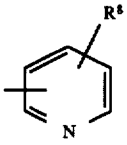
or
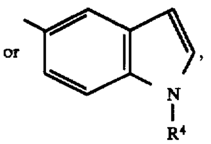
,

W' is selected from O, S, NH, N-lower alkyl ($C_1$–$C_3$),

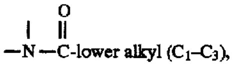

and $NSO_2$-lower alkyl ($C_1$–$C_3$);

$R^4$ and $R^5$ are as hereinbefore defined;

$R^8$ and $R^9$ are independently selected from H, lower alkyl ($C_1$–$C_3$), —S-lower alkyl ($C_1$–$C_3$), halogen, —NH-lower alkyl ($C_1$–$C_3$), —N-[lower alkyl ($C_1$–$C_3$)]$_2$, —$OCF_3$, —OH, —CN, —S—$CF_3$, —$NO_2$, —$NH_2$, —O-lower alkyl ($C_1$–$C_3$), NHCO lower alkyl ($C_1$–$C_3$), —O—CO-lower alkyl ($C_1$–$C_3$), —$N(R_b)(CH_2)_qN(R_b)_2$ and —$CF_3$; and $R^{10}$ is selected from H, halogen, lower alkyl ($C_1$–$C_3$);

(b) a moiety of the formula:

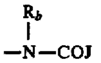

wherein

J is $R_a$, lower alkyl ($C_3$–$C_8$) branched or unbranched, lower alkenyl ($C_3$–$C_8$) branched or unbranched, —O-lower alkyl ($C_3$–$C_8$) branched or unbranched, —O-lower alkenyl($C_3$–$C_8$) branched or unbranched, tetrahydrofuran, tetrahydrothiophene, the moieties:

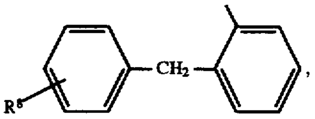
,

-continued

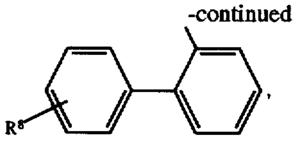
,

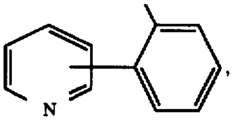
,
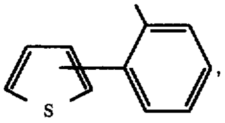
,

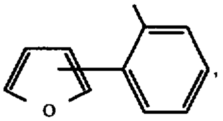
, or

—$CH_2$—K' wherein K' is ($C_1$–$C_3$) lower alkoxy, halogen, tetrahydrofuran, tetrahydrothiophene or the heterocyclic ring moiety:

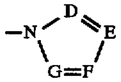

wherein

D, E, F and G are selected from carbon or nitrogen and wherein the carbon atoms may be optionally substituted with halogen, ($C_1$–$C_3$) lower alkyl, hydroxy, —CO-lower alkyl ($C_1$–$C_3$), CHO, ($C_1$–$C_3$)lower alkoxy, or —$CO_2$-lower alkyl ($C_1$–$C_3$), and $R_a$ and $R_b$ are as hereinbefore defined;

(c) a moiety of the formula:

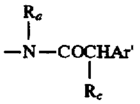

wherein $R_c$ is selected from halogen, ($C_1$–$C_3$) lower alkyl, —O-lower alkyl ($C_1$–$C_3$), OH,

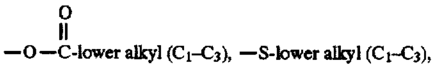

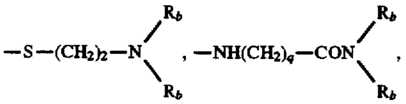

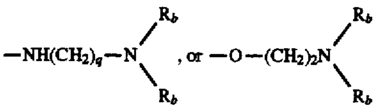

wherein $R_a$, $R_b$, Ar' and q are as hereinbefore defined;

(d) a moiety of the formula:

—M—$R_d$ wherein

M, $R_d$, p, $R_1$, and $R_2$ are as hereinbefore defined;

or a pharmaceutically acceptable salt, ester or prodrug form thereof.

2. A compound selected from Formula I:

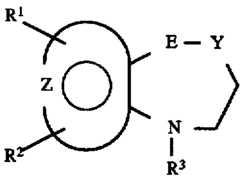

Formula I wherein:

E—Y is selected from the moieties —CH=CH— or $—CH_2CH_2—$;

the moiety

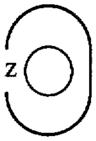

represents a fused 5-membered aromatic (unsaturated) [3,2-b]heterocyclic ring having one heteroatom selected from O or S;

$R^1$ and $R^2$ are selected from the group of H, $(C_1–C_3)$ lower alkyl, halogen, or $(C_1–C_3)$ lower alkoxy;

$R^3$ is —COAr, wherein Ar is a moiety selected from the group

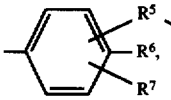

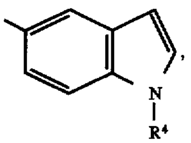

,

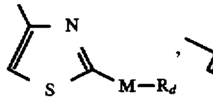

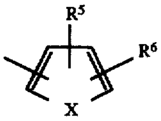

, and 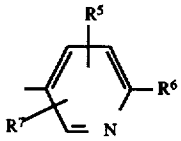

wherein in the moiety $—M—R_d$, when M is O, S, NH, or $NCH_3$, $R_d$ is lower alkyl $(C_3–C_8)$, lower alkenyl$(C_3–C_8)$, or $—(CH_2)_p$-cycloalkyl $(C_3–C_6)$, and, when M is a bond or M is selected from O, S, NH or $NCH_3$, $R_d$ is selected from the moieties:

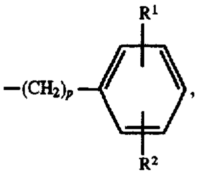

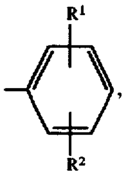

-continued

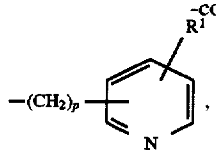

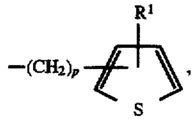

, or

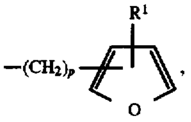

p is 0 to 4;

$R^1$ and $R^2$ are as hereinbefore defined;

X is selected from O, S, —NH, $NCH_3$ and $—NCOCH_3$;

$R^4$ is selected from H, lower alkyl $(C_1–C_3)$, —CO-lower alkyl $(C_1–C_3)$,

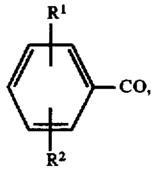

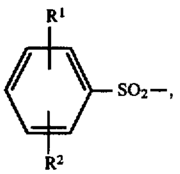

or $—SO_2$-lower alkyl $(C_1–C_3)$;

$R^1$ and $R^2$ are as defined above;

$R^5$ is selected from H, lower alkyl $(C_1–C_3)$, lower alkoxy $(C_1–C_3)$, and halogen;

$R^7$ is selected from H, lower alkyl $(C_1–C_3)$, halogen, O-lower alkyl $(C_1–C_3)$, and $CF_3$;

$R^6$ is selected from (a) the moieties of the formulae:

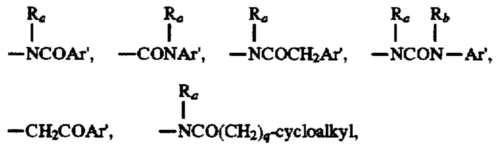

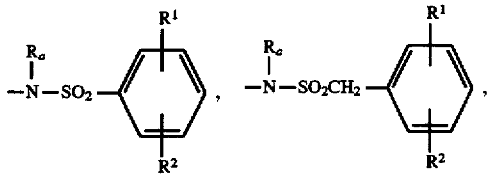

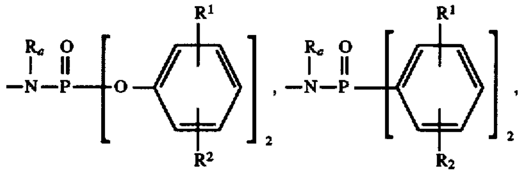

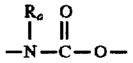

lower alkyl ($C_3$–$C_8$) straight or branched,

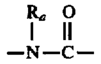

lower alkyl ($C_3$–$C_8$) straight or branched,

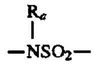

lower alkyl ($C_3$–$C_8$) straight or branched,

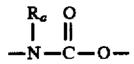

lower alkenyl ($C_3$–$C_8$) straight or branched,

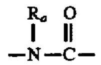

lower alkenyl ($C_3$–$C_8$) straight or branched,

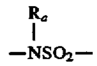

lower alkenyl ($C_3$–$C_8$) straight or branched, wherein cycloalkyl is defined as $C_3$–$C_6$ cycloalkyl, cyclohexenyl or cyclopentenyl;

$R_a$ is independently selected from hydrogen, —$CH_3$, —$C_2H_5$, moieties of the formulae:

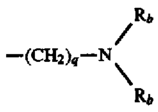

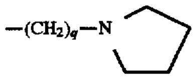,

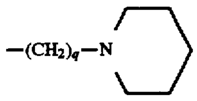, or 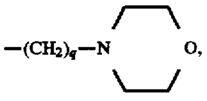

—$(CH_2)_q$—O-lower alkyl ($C_1$–$C_3$) or —$CH_2CH_2OH$;

q is one, two or three;

$R_b$ is independently selected from H, —$CH_3$, or —$C_2H_5$;

Ar' is selected from the moieties of the formula:

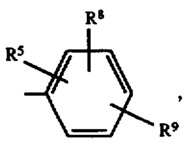, 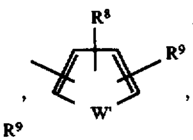, 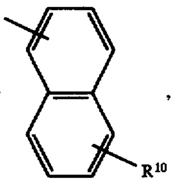,

-continued

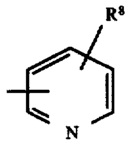 or 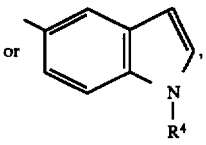,

W' is selected from O, S, NH, N-lower alkyl ($C_1$–$C_3$),

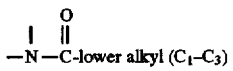

and $NSO_2$-lower alkyl ($C_1$–$C_3$);

$R^4$ and $R^5$ are as hereinbefore defined;

$R^8$ and $R^9$ are independently selected from H, lower alkyl ($C_1$–$C_3$), —S-lower alkyl ($C_1$–$C_3$), halogen, —NH-lower alkyl ($C_1$–$C_3$), —N-[lower alkyl ($C_1$–$C_3$)]$_2$, —$OCF_3$, —OH, —CN, —S—$CF_3$, —$NO_2$, —$NH_2$, —O-lower alkyl ($C_1$–$C_3$), NHCO lower alkyl ($C_1$–$C_3$), —O—CO-lower alkyl ($C_1$–$C_3$), —$N(R_b)(CH_2)_qN(R_b)_2$ and —$CF_3$; and $R^{10}$ is selected from H, halogen, lower alkyl ($C_1$–$C_3$);

(b) a moiety of the formula:

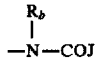

wherein

J is $R_a$, lower alkyl ($C_3$–$C_8$) branched or unbranched, lower alkenyl($C_3$–$C_8$) branched or unbranched, —O-lower alkyl ($C_3$–$C_8$) branched or unbranched, —O-lower alkenyl($C_3$–$C_8$) branched or unbranched, tetrahydrofuran, tetrahydrothiophene, the moieties:

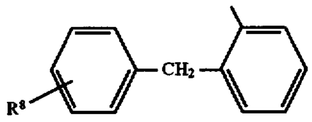,

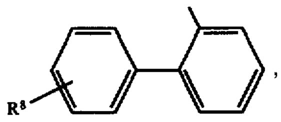,

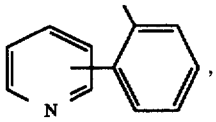,

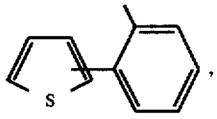,

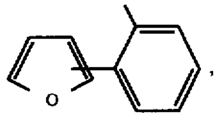, or

—$CH_2$—K' wherein K' is ($C_1$–$C_3$) lower alkoxy, halogen, tetrahydrofuran, tetrahydrothiophene or the heterocyclic ring moiety:

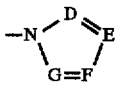

wherein

D, E, F and G are selected from carbon or nitrogen and wherein the carbon atoms may be optionally substituted with halogen, ($C_1$–$C_3$) lower alkyl, hydroxy, —CO-lower alkyl ($C_1$–$C_3$), CHO, ($C_1$–$C_3$) lower alkoxy, or —$CO_2$-lower alkyl ($C_1$–$C_3$), and $R_a$ and $R_b$ are as hereinbefore defined;

(c) a moiety of the formula:

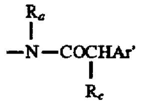

wherein $R_c$ is selected from halogen, ($C_1$–$C_3$) lower alkyl, —O-lower alkyl ($C_1$–$C_3$), OH,

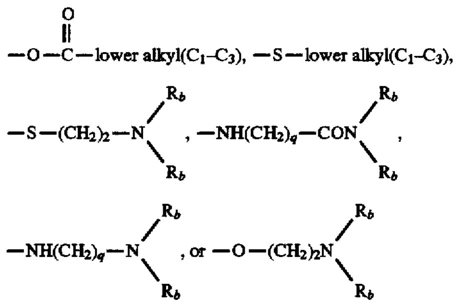

wherein $R_a$, $R_b$, Ar' and q are as hereinbefore defined;

(d) a moiety of the formula:

—M—$R_d$ wherein

M, $R_d$, p, $R_1$, and $R_2$ are as hereinbefore defined;

or a pharmaceutically acceptable salt, ester or prodrug form thereof.

3. A compound selected from Formula I:

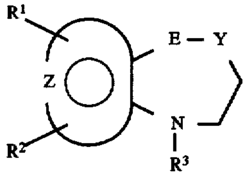

Formula I wherein:

E—Y is selected from the moieties —CH=CH— or —$CH_2CH_2$—;

the moiety

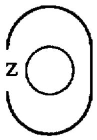

represents a fused 5-membered aromatic (unsaturated) [3,2-b]heterocyclic ring having one heteroatom selected from O or S, the fused 5-membered aromatic (unsaturated) heterocyclic ring being optionally substituted by ($C_1$–$C_3$) lower alkyl, halogen, or ($C_1$–$C_3$) lower alkoxy;

$R^3$ is —COAr, wherein Ar is a moiety selected from the group

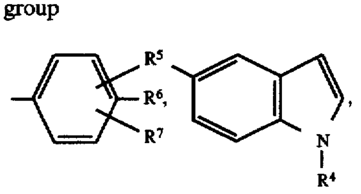

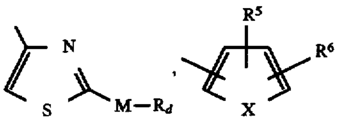

and

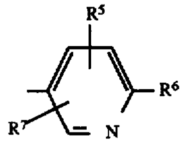

wherein:

in the moiety —M—$R_d$, when M is O, S, NH, $NCH_3$, $R_d$ is lower alkyl ($C_3$–$C_8$), lower alkenyl ($C_3$–$C_8$), or —$(CH_2)_p$-cycloalkyl($C_3$–$C_6$), and, when M is a bond or M is selected from O, S, NH or $NCH_3$, $R_d$ is selected from the moieties:

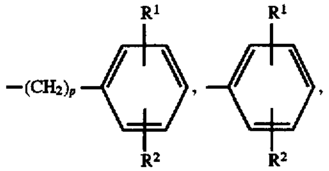

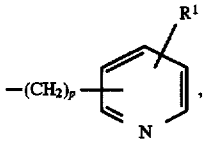

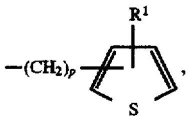

, or

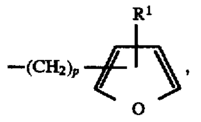

p is 0 to 4;

$R^1$ and $R^2$ are selected from ($C_1$–$C_3$) lower alkyl, halogen, or ($C_1$–$C_3$) lower alkoxy;;

X is selected from O, S, —NH, $NCH_3$ and —$NCOCH_3$;

$R^4$ is selected from H, lower alkyl ($C_1$–$C_3$), —CO-lower alkyl ($C_1$–$C_3$),

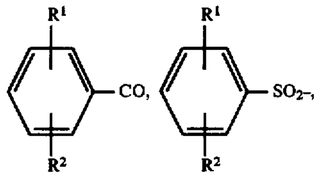

or

—$SO_2$-lower alkyl ($C_1$–$C_3$);

$R^1$ and $R^2$ are as defined above;

$R^5$ is selected from H, lower alkyl ($C_1$–$C_3$), lower alkoxy ($C_1$–$C_3$), and halogen;

$R^1$ is selected from H, lower alkyl ($C_1$–$C_3$), halogen, —O-lower alkyl ($C_1$–$C_3$), and $CF_3$;

$R^6$ is selected from (a) the moieties of the formulae:

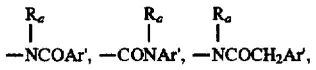

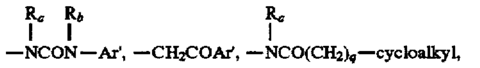

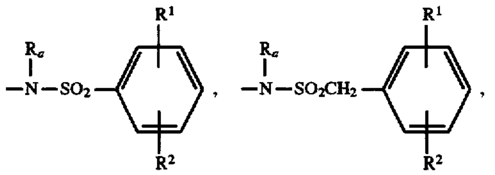

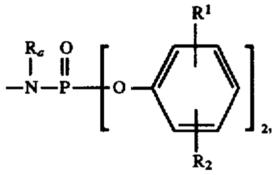

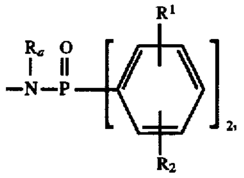

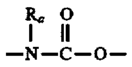

lower alkyl ($C_3$–$C_8$) straight or branched,

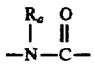

lower alkyl ($C_3$–$C_8$) straight or branched,

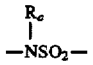

lower alkyl ($C_3$–$C_8$) straight or branched,

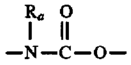

lower alkenyl ($C_3$–$C_8$) straight or branched,

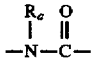

lower alkenyl ($C_3$–$C_8$) straight or branched,

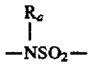

lower alkenyl ($C_3$–$C_8$) straight or branched, wherein cycloalkyl is defined as $C_3$–$C_6$ cycloalkyl, cyclohexenyl or cyclopentenyl;

$R_a$ is independently selected from hydrogen, —$CH_3$, —$C_2H_5$, moieties of the formulae:

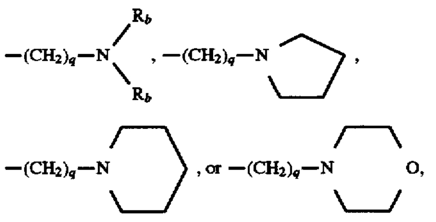

—$(CH_2)_q$—O-lower alkyl ($C_1$–$C_3$) or —$CH_2CH_2OH$;

q is one, two or three;

$R_b$ is independently selected from H, —$CH_3$, or —$C_2H_5$;

Ar' is selected from the moieties of the formula:

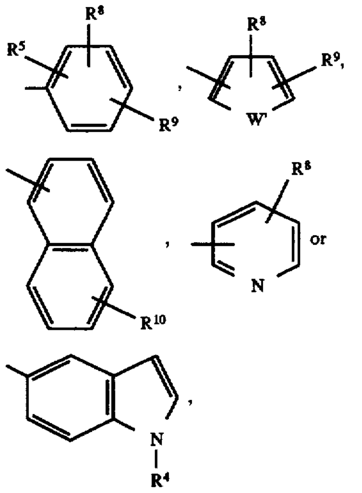

W' is selected from O, S, NH, N-lower alkyl ($C_1$–$C_3$), NCO-lower alkyl ($C_1$–$C_3$), and $NSO_2$-lower alkyl ($C_1$–$C_3$);

$R^4$ and $R^5$ are as hereinbefore defined;

$R^8$ and $R^9$ are independently selected from H, lower alkyl ($C_1$–$C_3$), —S-lower alkyl ($C_1$–$C_3$), halogen, —NH-lower alkyl ($C_1$–$C_3$), —N-[lower alkyl ($C_{1-3}$)]$_2$, —$OCF_3$, —OH, —CN, —S-$CF_3$, —$NO_2$, —$NH_2$, —O-lower alkyl ($C_1$–$C_3$), NHCO lower alkyl ($C_1$–$C_3$), —O—CO-lower alkyl ($C_1$–$C_3$), —$N(R_b)(CH_2)_qN(R_b)_2$ and —$CF_3$; and $R^{10}$ is selected from H, halogen, lower alkyl ($C_1$–$C_3$);

(b) a moiety of the formula:

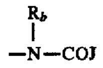

wherein

J is $R_a$, lower alkyl ($C_3$–$C_8$) branched or unbranched, lower alkenyl($C_3$–$C_8$) branched or unbranched, —O-lower alkyl ($C_3$–$C_8$) branched or unbranched, —O-lower alkenyl($C_3$–$C_8$) branched or unbranched, tetrahydrofuran, tetrahydrothiophene, the moieties:

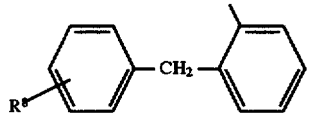
,

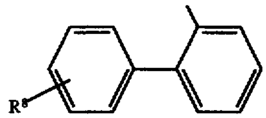
,

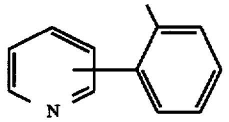
,

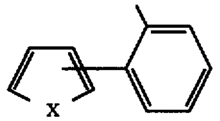
,

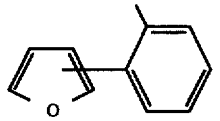
, or

—$CH_2$—K' wherein K' is ($C_1$–$C_3$) lower alkoxy, halogen, tetrahydrofuran, tetrahydrothiophene or the heterocyclic ring moiety:

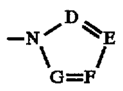

wherein

D, E, F and G are selected from carbon or nitrogen and wherein the carbon atoms may be optionally substituted with halogen, ($C_1$–$C_3$) lower alkyl, hydroxy, —CO-lower alkyl ($C_1$–$C_3$), CHO, ($C_1$–$C_3$) lower alkoxy, or —$CO_2$-lower alkyl ($C_1$–$C_3$), and $R_a$ and $R_b$ are as hereinbefore defined;

(c) a moiety of the formula:

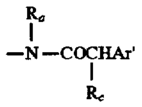

wherein $R_c$ is selected from halogen, ($C_1$–$C_3$) lower alkyl, —O-lower alkyl ($C_1$–$C_3$), OH,

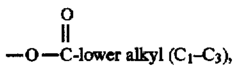
, —S-lower alkyl ($C_1$–$C_3$),

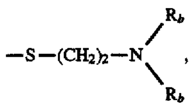
,
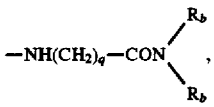
,

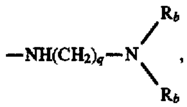
, or
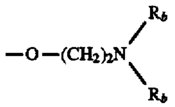

wherein $R_a$, $R_b$, Ar' and q are as hereinbefore defined;

(d) a moiety of the formula:

—M—$R_d$ wherein

M, $R_d$, p, $R_1$, and $R_2$ are as hereinbefore defined;

or a pharmaceutically acceptable salt, ester or prodrug form thereof.

4. A compound according to claim 1 wherein the moiety

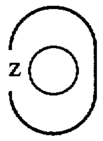

represents an unsaturated 5-membered aromatic furan ring optionally substituted by ($C_1$–$C_3$) lower alkyl, halogen, or ($C_1$–$C_3$) lower alkoxy.

5. A compound according to claim 1 wherein the moiety

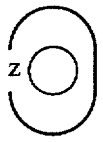

represents a [3,2-b]furan ring optionally substituted by ($C_1$–$C_3$) lower alkyl, halogen, or ($C_1$–$C_3$) lower alkoxy.

6. A compound according to claim 1 wherein the moiety

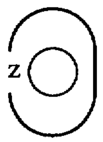

represents an unsaturated 5-membered aromatic thiophene ring optionally substituted by ($C_1$–$C_3$) lower alkyl, halogen, or ($C_1$–$C_3$) lower alkoxy.

7. A compound according to claim 1 wherein the moiety

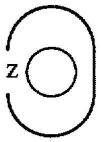

represents a [3,2-b]thiophene ring optionally substituted by ($C_1$–$C_3$) lower alkyl, halogen, or ($C_1$–$C_3$) lower alkoxy.

8. A compound according to claim 2 wherein the moiety

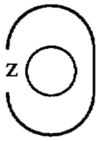

represents a [3,2-b]furan ring optionally substituted by ($C_1$–$C_3$) lower alkyl, halogen, or ($C_1$–$C_3$) lower alkoxy.

9. A compound according to claim 2 wherein the moiety

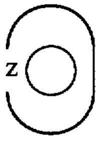

represents a [3,2-b]thiophene ring optionally substituted by ($C_1$–$C_3$) lower alkyl, halogen, or ($C_1$–$C_3$) lower alkoxy.

10. A compound according to claim 1 which is N-[4-[(5,6,7,8-tetrahydro-4H-thieno[3,2-b]azepin-4-yl)-carbonyl]phenyl]-3,4-dichlorobenzamide or a pharmaceutically acceptable salt, ester or prodrug form thereof.

11. A compound according to claim 1 which is N-[4-[(5,6,7,8-tetrahydro-4H-thieno[3,2-b]azepin-4-yl)-carbonyl]phenyl]-2-methylbenzamide or a pharmaceutically acceptable salt, ester or prodrug form thereof.

12. A compound according to claim 1 which is N-[4-[(5,6,7,8-tetrahydro-4H-thieno[3,2-b]azepin-4-yl)-carbonyl]phenyl]-2-furanecarboxamide or a pharmaceutically acceptable salt, ester or prodrug form thereof.

13. A compound according to claim 1 which is N-[4-[(5,6,7,8-tetrahydro-4H-thieno[3,2-b]azepin-4-yl)-carbonyl]phenyl]-4-(n-butyl)benzamide or a pharmaceutically acceptable salt, ester or prodrug form thereof.

14. A compound according to claim 1 which is N-[4-[(5,6,7,8-tetrahydro-4H-thieno[3,2-b]azepin-4-yl)-carbonyl]phenyl]-2,4-dimethylbenzamide or a pharmaceutically acceptable salt, ester or prodrug form thereof.

15. A compound according to claim 1 which is N-[4-[(5,6,7,8-tetrahydro-4H-thieno[3,2-b]azepin-4-yl)-carbonyl]phenyl]benzeneacetamide or a pharmaceutically acceptable salt, ester or prodrug form thereof.

16. A compound according to claim 1 which is N-[4-[(5,6,7,8-tetrahydro-4H-thieno[3,2-b]azepin-4-yl)-carbonyl]phenyl]-2,4-dichlorobenzamide or a pharmaceutically acceptable salt, ester or prodrug form thereof.

17. A compound according to claim 1 which is N-[4-[(2-chloro-5,6,7,8-tetrahydro-4H-thieno[3,2-b]azepin-4-yl)-carbonyl]phenyl]-2-methylbenzamide or a pharmaceutically acceptable salt, ester or prodrug form thereof.

18. A compound according to claim 1 which is N-[4-[(2-chloro-5,6,7,8-tetrahydro-4H-thieno[3,2-b]azepin-4-yl)-carbonyl]-3-methoxyphenyl]-5-fluoro-2-methylbenzamide or a pharmaceutically acceptable salt, ester or prodrug form thereof.

19. A compound according to claim 1 which is N-[4-[(5,6,7,8-tetrahydro-8-oxo-4H-thieno[3,2-b]azepin-4-yl)-carbonyl]phenyl]-3-fluoro-2-methylbenzamide or a pharmaceutically acceptable salt, ester or prodrug form thereof.

20. A compound according to claim 1 which is N-[4-[(5,6,7,8-tetrahydro-8-oxo-4H-thieno[3,2-b]azepin-4-yl)-carbonyl]phenyl]-2,4-dichlorobenzamide or a pharmaceutically acceptable salt, ester or prodrug form thereof.

21. A compound according to claim 1 which is N-[4-[(5,6,7,8-tetrahydro-8-oxo-4H-thieno[3,2-b]azepin-4-yl)-carbonyl]phenyl]-5-fluoro-2-methylbenzamide or a pharmaceutically acceptable salt, ester or prodrug form thereof.

22. A compound according to claim 1 which is N-[4-[(5,6,7,8-tetrahydro-8-oxo-4H-thieno[3,2-b]azepin-4-yl)-carbonyl]3-chlorophenyl]-3-fluoro-2-methylbenzamide or a pharmaceutically acceptable salt, ester or prodrug form thereof.

23. A compound according to claim 1 which is N-[4-[(5,6,7,8-tetrahydro-4H-thieno[3,2-b]azepin-4-yl)-carbonyl]-3-chlorophenyl]-2-chloro-4-fluorobenzamide or a pharmaceutically acceptable salt, ester or prodrug form thereof.

24. A compound according to claim 1 which is N-[4-[(5,6-dihydro-4H-thieno[3,2-b]azepin-4-yl)-carbonyl]-3-chlorophenyl]-5-fluoro-2-methylbenzamide or a pharmaceutically acceptable salt, ester or prodrug form thereof.

25. A compound according to claim 1 which is N-[5-[(5,6,7,8-tetrahydro-4H-thieno[3,2-b]azepin-4-yl)-carbonyl]-2-pyridinyl][1,1'-biphenyl]-2-carboxamide or a pharmaceutically acceptable salt, ester or prodrug form thereof.

26. A compound according to claim 1 which is N-[4-[(5,6,7,8-tetrahydro-4H-thieno[3,2-b]azepin-4-yl)carbonyl]-3-chlorophenyl][1,1'-biphenyl]-2-carboxamide or a pharmaceutically acceptable salt, ester or prodrug form thereof.

27. A compound according to claim 1 which is N-[4-[(5,6,7,8-tetrahydro-4H-thieno[3,2-b]azepin-4-yl)carbonyl]phenyl][1,1'-biphenyl]-2-carboxamide or a pharmaceutically acceptable salt, ester or prodrug form thereof.

28. A pharmaceutical composition useful for treating disease in a mammal characterized by excess renal reabsorption of water, the pharmaceutical composition comprising an effective amount of a compound of claim 1, or a pharmaceutically acceptable salt, ester or prodrug form thereof, and a suitable pharmaceutical carder.

29. The pharmaceutical composition of claim 28 wherein the disease in a mammal characterized by excess renal reabsorption of water is congestive heart failure, nephrotic syndrome, hyponatremia, coronary vasospasm, cardiac ischemia, renal vasospasm, liver cirrhosis, brain edema, cerebral ischemia, or cerebral hemorrhage-stroke.

30. A method for treating disease in a mammal characterized by excess renal reabsorption of water, the method comprising administering to a mammal in need thereof an effective amount of a compound of claim 1, or a pharmaceutically acceptable salt, ester or prodrug form thereof, and a suitable pharmaceutical carrier.

31. The method of claim 30 wherein the disease in a mammal characterized by excess renal reabsorption of water is congestive heart failure, nephrotic syndrome, hyponatremia, coronary vasospasm, cardiac ischemia, renal vasospasm, liver cirrhosis, brain edema, cerebral ischemia, or cerebral hemorrhage-stroke.

* * * * *